US008633331B2

(12) United States Patent
Bandosz et al.

(10) Patent No.: US 8,633,331 B2
(45) Date of Patent: Jan. 21, 2014

(54) NANOCOMPOSITE MATERIALS COMPRISING METAL-ORGANIC-FRAMEWORK UNITS AND METHODS OF USING SAME

(75) Inventors: Teresa J. Bandosz, Teaneck, NJ (US); Camille Petit, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 553 days.

(21) Appl. No.: 12/879,701

(22) Filed: Sep. 10, 2010

(65) Prior Publication Data
US 2011/0217217 A1  Sep. 8, 2011

Related U.S. Application Data

(60) Provisional application No. 61/313,913, filed on Mar. 15, 2010, provisional application No. 61/241,302, filed on Sep. 10, 2009.

(51) Int. Cl.
*C07F 1/08* (2006.01)
*C07F 3/06* (2006.01)
*C07F 15/02* (2006.01)
*C07F 15/04* (2006.01)
*C07F 15/06* (2006.01)
*C07F 11/00* (2006.01)
*C01B 31/04* (2006.01)
*B01D 53/40* (2006.01)
*B01D 53/42* (2006.01)

(52) U.S. Cl.
USPC ........... 556/115; 556/57; 556/132; 556/147; 423/448; 423/700; 423/701; 423/702; 423/703; 423/713; 252/184

(58) Field of Classification Search
USPC ........... 423/448, 700–703, 713; 556/115, 57, 556/132, 147; 252/184
See application file for complete search history.

(56) References Cited

U.S. PATENT DOCUMENTS

| 6,893,564 | B2 * | 5/2005 | Mueller et al. | 210/502.1 |
| 2006/0185388 | A1 * | 8/2006 | Muller et al. | 62/606 |
| 2012/0210872 | A1 * | 8/2012 | Duan et al. | 95/127 |

OTHER PUBLICATIONS

Prestipino et al., "Local Structure of Framework Cu(II) in HKUST-1 Metallorganic Framework: Spectroscopic Characterization upon Activation and Interaction with Adsorbates." Chem. Mater. 2006, vol. 18, pp. 1337-1346 (published on Web Feb. 1, 2006).*

* cited by examiner

*Primary Examiner* — Stuart Hendrickson
*Assistant Examiner* — Daniel Berns
(74) *Attorney, Agent, or Firm* — Hoffmann & Baron, LLP

(57) ABSTRACT

The present invention relates to nanocomposite materials comprising: graphite-based material dispersed among transition metal-organic framework (MOF) units, wherein the graphite-based material is chemically linked to MOF units; wherein the graphite-based material is present in the range of about 5 wt. % to about 60 wt. % of the composite material.

17 Claims, 9 Drawing Sheets

NANOCOMPOSITE MATERIALS COMPRISING METAL-ORGANIC-FRAMEWORK UNITS AND METHODS OF USING SAME

CROSS-REFERENCE TO RELATED APPLICATION

This application claims the benefit of U.S. Provisional Application Nos. 61/241,302 and 61/313,913, filed Sep. 10, 2009 and Mar. 15, 2010, respectively, which are incorporated herein by reference in their entireties.

This invention was made with Government support from the National Science Foundation and the Army Research Office. The Government has certain rights in this invention.

BACKGROUND OF THE INVENTION

There is a need to filter/adsorb toxic molecules from air. Toxic industrial compounds include such gases as $NH_3$, $NO_x$, $H_2S$, $SO_2$, $AsH_3$, etc. Their physical adsorption at ambient conditions is limited due to their small size. Also adsorption forces are rather weak. Therefore, many researchers focus on the development of new adsorbents which would not only adsorb those gases in significant quantities but also provide strong adsorption forces preventing desorption from the surface. However, no effective and economical solution has yet been found.

SUMMARY OF THE INVENTION

In one embodiment, the present invention relates to a nanocomposite material comprising graphite-based material dispersed among transition metal-organic framework (MOF) units. The graphite-based material is chemically linked to MOF units. The graphite-based material is present in the range of about 5 wt. % to about 80 wt. % of the composite material. The materials exhibit superior adsorptive properties for gases. Moreover, both nanocomposite components are able to provide centers for reactive adsorption thereby chemically bonding the adsorbates to the nanocomposites surfaces.

DETAILED DESCRIPTION OF THE INVENTION

Figure 1:
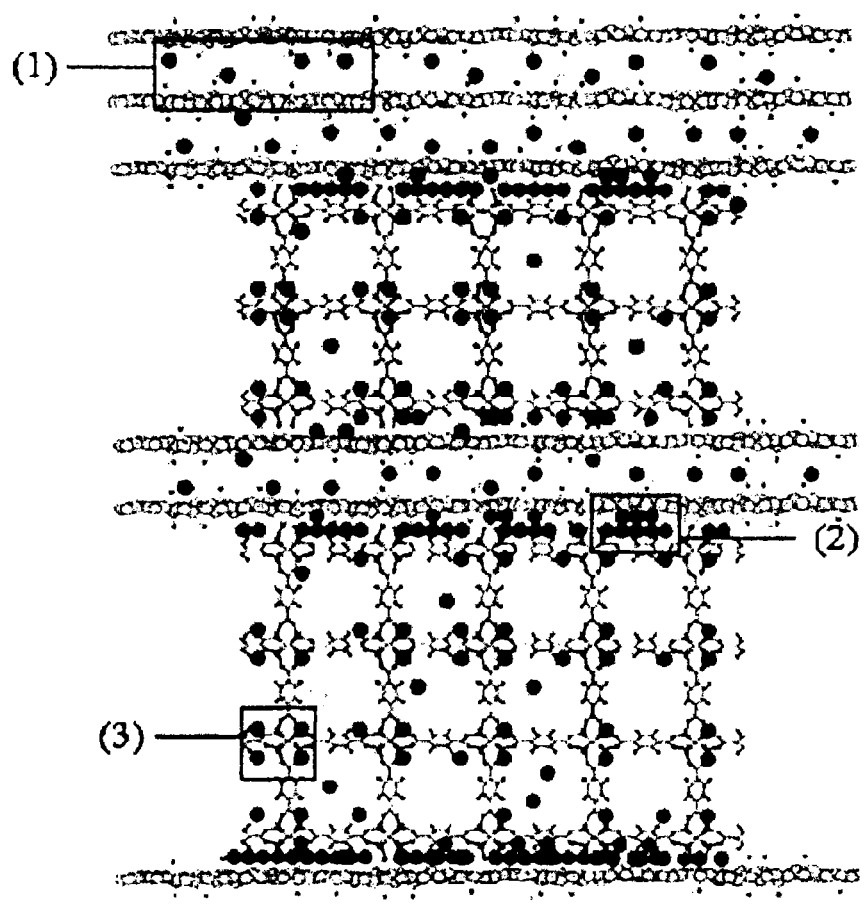
FIG. 1. Schematic representation of the mechanisms of ammonia (black circle) adsorption in the composites including: (1)—Intercalation between the graphene layers, (2)—Adsorption at the interface between the graphene layers and the MOF-5 segments, (3)—Hydrogen bonding with the oxygen atoms form the zinc oxide clusters in MOF-5.

The present invention relates to nanocomposite materials comprising graphite-based materials dispersed among transition metal-organic framework (MOF) units, and methods of making and using these materials.

Throughout this specification, quantities are defined by ranges, and by lower and upper boundaries of ranges. Each lower boundary can be combined with each upper boundary to define a range. The lower and upper boundaries should each be taken as a separate element.

Graphite-Based Material

A graphite-based material is any material that comprises substantially carbon in substantially a layered structure.

The amount of the graphite-based material typically present in a nanocomposite material is in the range of about 5 wt. % to about 80 wt. %. The lower and upper boundaries of this range can vary. Examples of other lower boundaries of this range include about 10 wt. %, about 20 wt. %, about 30 wt. %, about 40 wt. %, and about 50 wt. %. Examples of other upper boundaries of this range include about 50 wt. %, about 60 wt. %, and about 70 wt. %.

Examples of graphite-based materials include graphene, graphite, graphite oxide (GO), and mixtures thereof. Graphene is a one-atom-thick planar sheet of $sp^2$-bonded carbon atoms that are densely packed in a honeycomb crystal lattice. Graphite is a layered compound. In each layer, the carbon atoms are substantially arranged in a hexagonal lattice with separation of about 0.142 nm, and the distance between planes is about 0.335 nm. Layers of graphene and graphite are sometimes referred to as "flakes."

Graphite oxide (also called graphitic oxide or graphitic acid) is a compound of carbon, oxygen, and hydrogen in variable ratios. It can be obtained by treating graphite with strong oxidizers. The maximally oxidized bulk product is a yellow solid with C:O ratio between about 2.1 and about 2.9, that essentially retains the layer structure of graphite but with a much larger and irregular spacing.

Metal-Organic Framework Units

A metal-organic framework (MOF) unit is composed of two major components: a metal ion or cluster of metal ions and an organic molecule linker. The organic units are typically mono-, di-, tri-, or tetravalent ligands. A MOF component which is not sensitive to hydrogen bonding is preferred.

Examples of MOFs units suitable for the composite material of the present invention include transition metal-based MOF units, wherein the transition metals include elements whose atom has an incomplete d sub-shell, or which can give rise to cations with an incomplete d sub-shell. Examples of suitable transition metals include copper, zinc, iron, cobalt, nickel, and chromium.

An example of a copper-based MOF unit is a $Cu_3$(benzenetricarboxylic)$_2$ (HKUST-1; MOF-199) unit. In HKUST-1, $Cu^{2+}$ ions form dimers, where each copper atom is coordinated by four oxygens, coming from the benzene-1,3,5 tricarboxilate linkers ($[Cu_2C_4O_8]$ cage) and one water molecule. An example of a zinc-based MOF unit is a $Zn_4O$(H-1,4-benzenedicarboxylate)$_3$ (MOF-5) unit. An example of a iron-based MOF unit is MIL-100(Fe). MIL-100(Fe) is a large-pore iron (III) carboxylate with a zeotype architecture. An example of a chromium-based MOF unit is a chromium(III) terephthalate (MIL-101) unit.

Examples of other suitable MOF units include MIL-53 comprising Al, Cr or Fe; MIL-47 comprising V; MIL-100 comprising Cr; and MIL-101 comprising Cr.

Further examples of suitable MOFs include zeolitic imidazolate frameworks (ZIF). Twelve ZIFs (termed ZIF-1 to -12) have been synthesized as crystals by copolymerization of either Zn(II) (ZIF-1 to -4, -6 to -8, and -10 to -11) or Co(II) (ZIF-9 and -12) with imidazolate-type links The ZIF crystal structures are based on the nets of seven distinct aluminosilicate zeolites: tetrahedral Si(Al) and the bridging O are replaced with transition metal ion and imidazolate link, respectively. In addition, examples of mixed-coordination imidazolates based on garnet nets include Zn(II) and In(III) (ZIF-5). A typical example is ZIF-8 $Zn_2$(2-methylimidazolate).

General Structures of the Composite Materials

The composite materials are substantially crystalline. The composite materials contain a high volume of micropores having, for example, a volume of at least about 0.250 $cm^3/g$ to about 3 $cm^3/g$. Micropores are pores with diameters less than 2 nm. The surface area of the composite materials are typically at least about 500 $m^2/g$ to about 3000 $m^2/g$.

The transition MOF units are structurally linked to the graphite-based materials to form the composite materials. That is, the MOF unit material and the graphite-based material are not simply a physical mixture of the two components. Typically, the MOF units are chemically linked to the graphite-based material.

Chemical linkages include covalent linkages, polar covalent linkages, and coordinate linkages. The covalent linkage can be via a single bond, or a double bond. Polar covalent linkages (hybrid bonds) are partially ionic in nature; that is, the electrons are not shared equally.

Typically, the linkage between graphite-based material and a MOF unit is through a functional group originating from the graphite-based material and/or from the MOF unit.

For example, in the embodiment in which graphite-based material is GO, the metal sites of the MOF unit (such as, for example, the copper sites of HKUST-1) react with functional groups of GO. Functional groups of GO include, for example, epoxy, hydroxylic, sulfonic and carboxylic functionalities. The most typical groups are the epoxy and carboxylic groups.

Without wanting to be held to a mechanism, it is believed that the reaction of the MOF units with the functionalities of GO lead to the creation of additional pores in the parent MOF materials. High porosity of the composite materials is likely responsible for the enhancement in the uptake of gases by the composite materials as compared to the respective physical mixture of MOF material and graphite-based material.

Typically, for a particular MOF material, porosity is enhanced up to a certain optimum level of GO content and then decreases with additional GO. Over such optimum level, the number of functionalities on the graphene layers likely exceeds the number of accessible sites in MOF with which they can react. Consequently, graphene layers remain as agglomerates resulting in a decrease in porosity. For example, for HKUST-1, enhancement in the porosity is seen for GO content up to about 30 wt % to about 40%, and then decreases.

Again, without wanting to be held to a mechanism, it is believed that the formation of the composite materials is governed by availability of the oxygen groups of GO and the way they are coordinated to the metallic sites. For example, in the case of MOF-5, all the oxygen atoms forming the zinc oxide tetrahedra are equivalent in terms of 2 5 spatial arrangement. Thus, structural changes with varying GO levels must be related to the oxygen groups of GO. GO contains oxygen groups on the basal planes (e.g., epoxy, hydroxyl, ketone) and on the edges of the layers (e.g., carboxylic and sulfonic groups). Depending on the type of groups interacting with MOF-5 metallic sites, the structure of the composite materials varies. For instance, a possible scenario for the formation of MOF-5 composite materials is the involvement of linkages between epoxy groups of distorted graphene layers of GO and zinc oxide building units of MOF-5. An increase in the content of GO leads to a greater distortion of the MOF-5 cubic structure and visible changes in the texture of nanocomposites.

Figure 5:
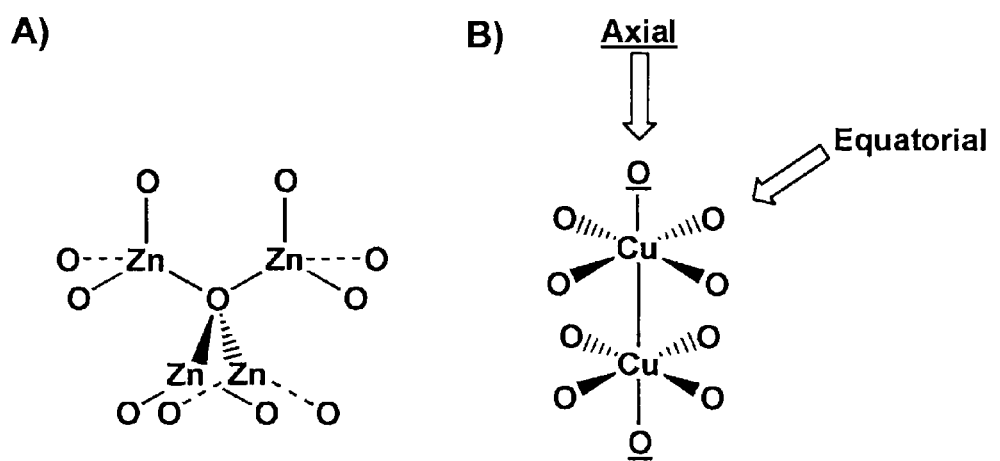
FIG. 5. Oxygen coordination sites available in A) MOF-5 and B) HKUST-1.
Figure 7A:
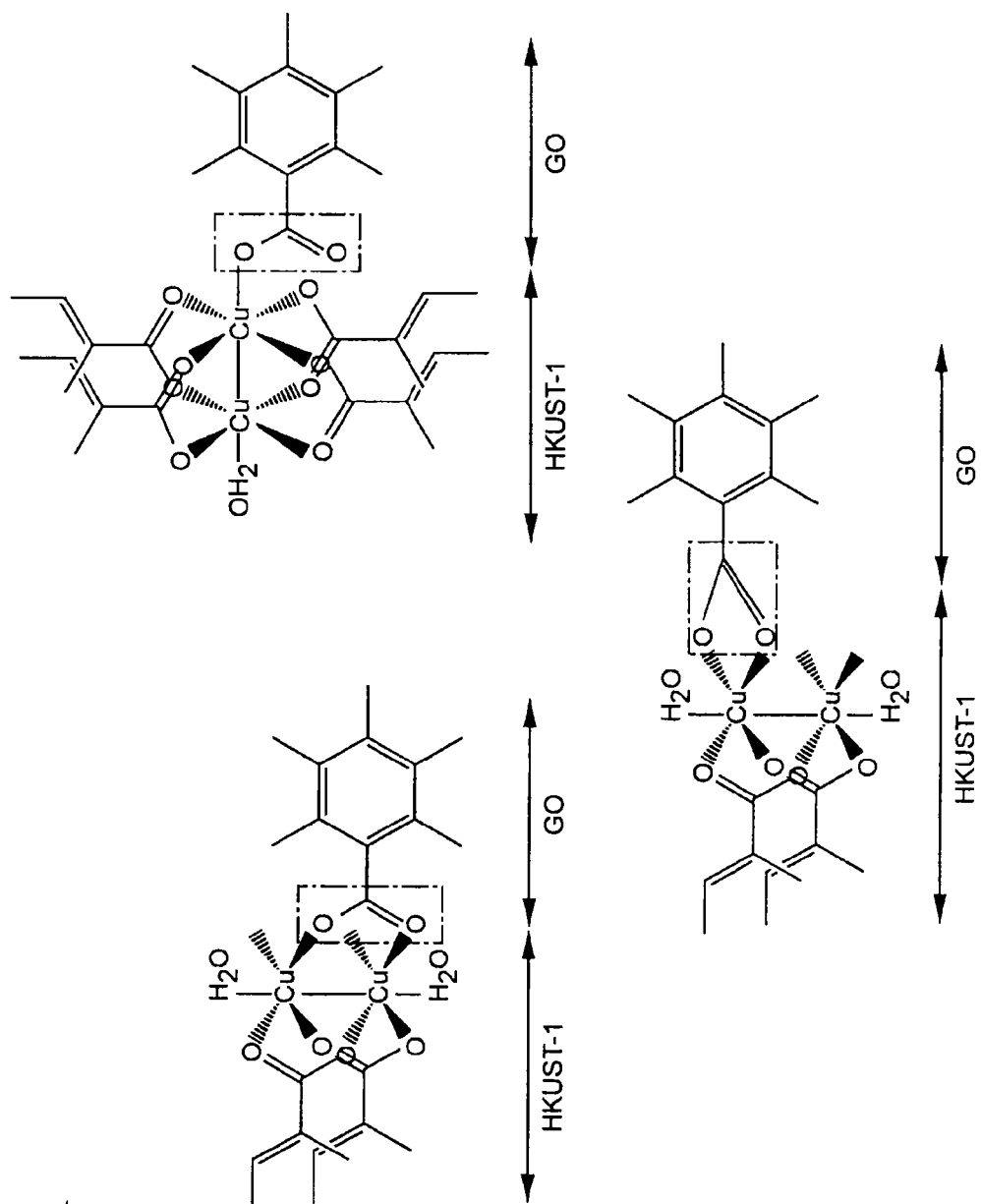
FIG. 7. Details of the possible interactions between the copper sites of HKUST-1 and the a) carboxylic, b) epoxy and c) hydroxyl groups of GO.
Figure 7B:
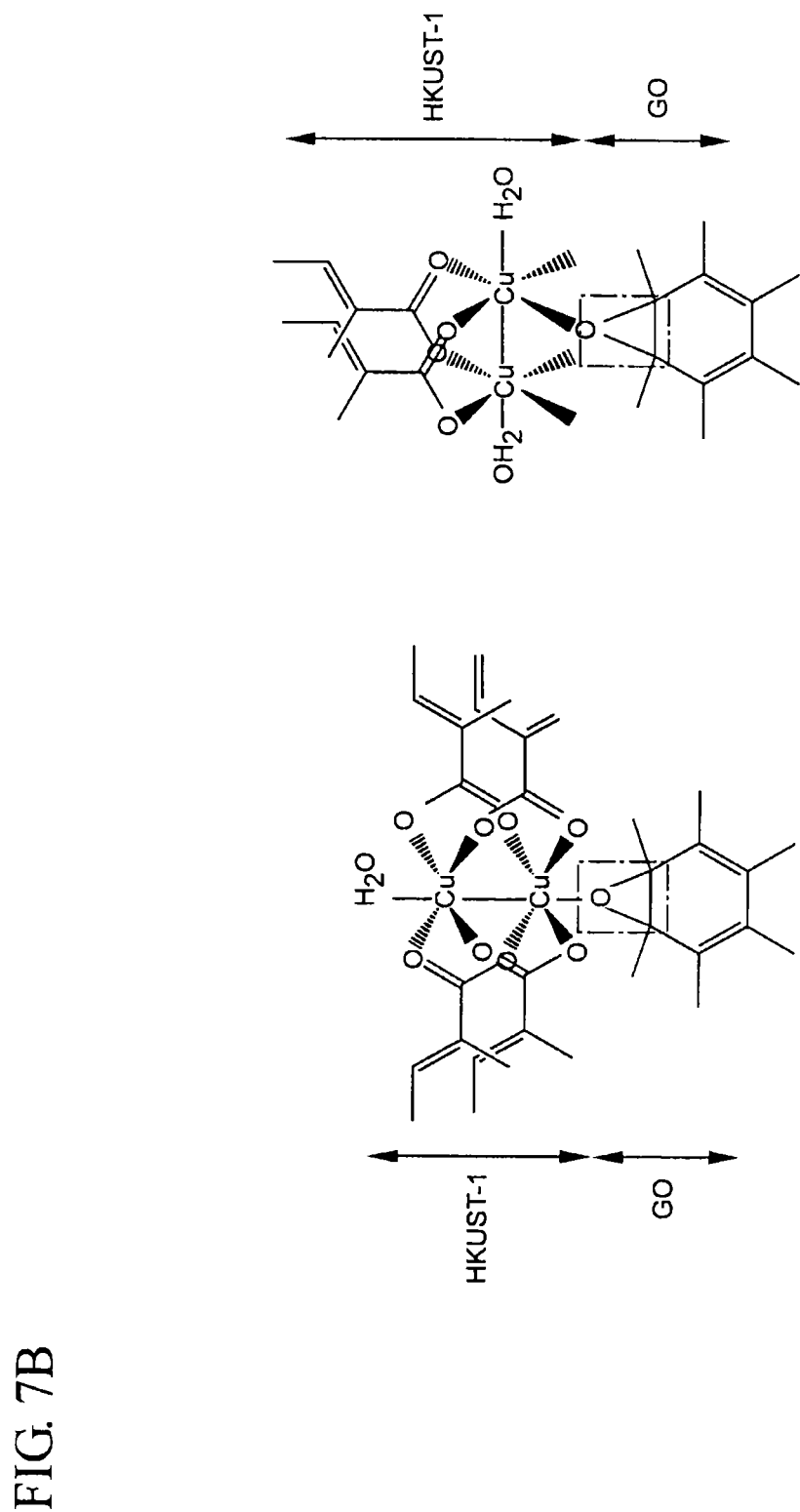
Figure 7C:
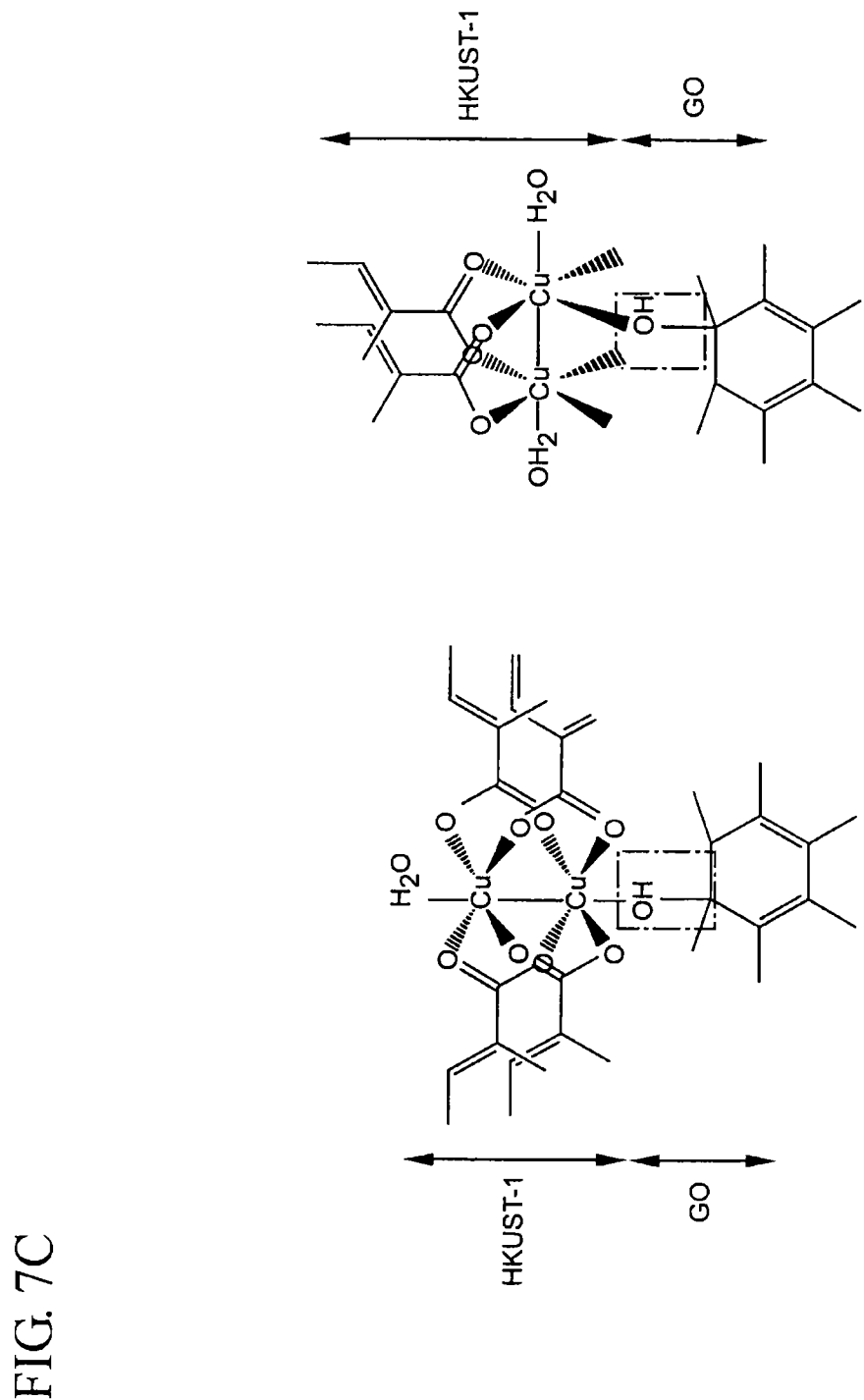
Figure 8:
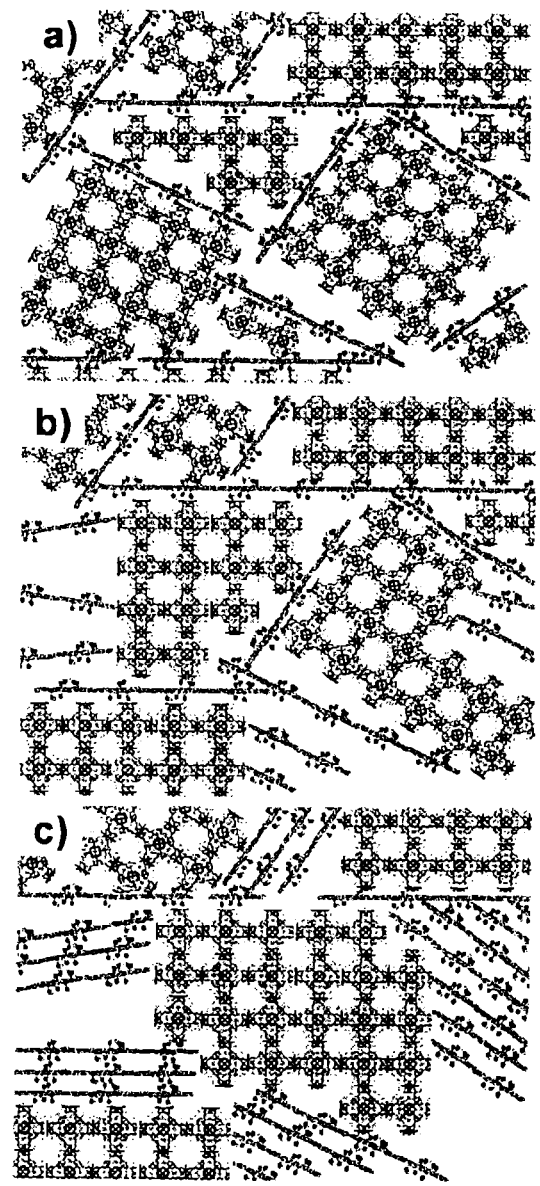
FIG. 8. Schematic representation of the composites with a) low, b) medium and c) high content of GO.

With respect to HKUST-1, the copper sites are not all equivalent. Thus, attachment of the oxygen groups of GO to copper can occur either in the axial position (replacement of water molecule) or in the equatorial position (replacement of benzenetricarboxylic groups) (see FIG. 5). Possible interactions are provided in FIG. 7. Axial and equatorial arrangements, along with the different types of oxygen groups from GO, can lead to the formation of a composite with the relatively disordered structure as shown in FIG. 8.

Because carboxylic groups (and sulfonic groups) of GO are located at the edges of the layers and not on the basal planes as the other functionalities, their interactions with the copper sites do not lead to the same type of arrangement as for epoxy, and hydroxylic present on the basal planes of GO. This can be seen in FIG. 8*b*. Higher content of GO leads to the formation of larger pores between the graphene flakes. This is the result of the interactions of more carboxylic groups (and sulfonic groups) on GO edges with copper sites. When even higher amounts of GO are present, the number of groups from GO can exceed the number of accessible MOF sites they can react with and the graphene layers remains as agglomerates. This is represented in FIG. 8*c*. This causes that smaller volumes of new small pores are formed.

Figure 6:
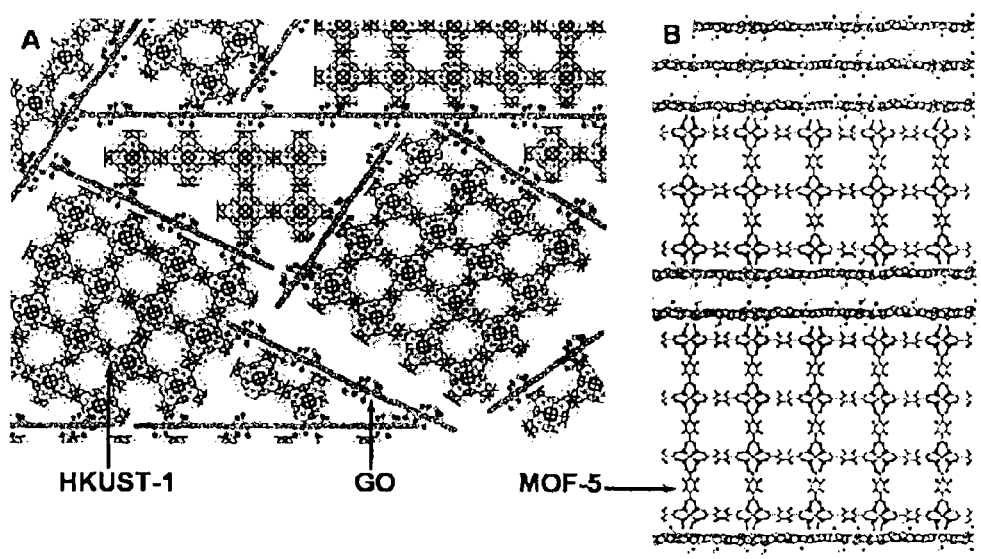
FIG. 6 Envisioned structures for the hybrid materials based on (A) MOF-5 and (B) HKUST-1.

Proposed structures for composite materials comprising MOF-5 or HKUST-1 are shown in FIG. 6. MOF-5 composite materials tend to have a more regular layered arrangement. HKUST-1 composite materials tend to exhibit a more disordered structure. In composite materials, a pore space is created between MOF blocks and GO units.

In the embodiment in which the graphite-based material is graphite/graphene, the functional groups/defects that bind graphite/graphene to a MOF unit can originate from the graphite/graphene or from the MOF unit itself. For example, HKUST-1 has two benzenetricarboxylic functional groups and MOF-5 has three benzenedicarboxylate functional groups. Graphite/graphene itself typically comprises impurities/defects which can provide functional groups.

In one embodiment, the nanocomposite material comprises HKUST-1 units, and the graphite-based material is present in the range of about 5 wt. % to about 50 wt. % of the composite material. In another embodiment, the nanocomposite material comprises MOF-5 units, and the graphite-based material is present in the range of about 5 wt. % to about 50 wt. % of the composite material.

Methods of Using the Nanocomposite Materials

In one embodiment of the present invention, a method of adsorbing gas is provided. The method comprises exposing a gas to a nanocomposite material of the present invention. The gas may be exposed to the nonocomposite material by methods known in the art. For example, the gas may be exposed to the nanocomposite material arranged in a bed or in a tube. Preferably, the gas is made to flow over or through the material in the bed or tube.

Adsorption of gas by the composites of the present invention is useful for various applications. For example, gas can be adsorbed in order to purify and/or filter air. Air purification can remove toxic gases (e.g., acidic toxic gas, basic toxic gas, or mixtures thereof) from the environment. Examples of toxic gases include $NH_3$, $NO_x$ (x=1 or 2) $H_2S$, $SO_2$, $AsH_3$, $H_2$, or combinations thereof. The nanocomposites can also separate different gases. In such case, adsorbed gases can be separated from other gases having less affinity. The nanocomposites can also be used as biosensors. In such case, the nanocomposites indicate that a particular type of gas was adsorbed, e.g., a color change upon adsorption. Also, since the presence of particular gases can change the conductivity of the nanocomposites, such nanocomposites can be used as sensors in the electronic industry. The nanocomposites can also be used as catalyst systems whereby adsorbed gas is converted to another gas via reaction with the material of the nanocomposite or reaction with a first gas initially adsorbed onto the nanocomposite.

Adsorption can take place under moist conditions or dry conditions, or conditions which range between the two conditions. Moist conditions are defined as at least 70% humidity in the challenge test and/or prehumidified bed, and environments that contain such levels of moisture. Dry conditions are defined as having substantially no moisture, in the challenge test and/or prehumidified bed, and environments that contain such levels of moisture. Examples of "substantially no moisture" is about 90% moisture free, about 95% moisture free, about 97% moisture free, and about 99% moisture free. Typically, adsorption takes place under ambient conditions and thus with a range of moisture present in air.

In one embodiment, the nanocomposite used to adsorb gas comprises HKUST-1 units and graphite-based material. The amount of the graphite-based material is in the range of about 5 wt. % to about 20 wt. % of the composite material. Gases that can be adsorbed include, for example, $H_2S_2$ and/or $NH_3$. In another embodiment, the nanocomposite is used to adsorb NO and/or $NO_2$. Preferably, in this embodiment, the adsorption is conducted under dry conditions.

In another embodiment, the nanocomposite used to adsorb gas comprises MOF-5 units and graphite-based material. The amount of the graphite-based material is in the range of about 5 wt. % to about 50 wt. % of the composite material. Gases that can be adsorbed include, for example, $NH_3$. Preferably, in this embodiment, the adsorption is conducted under dry conditions.

Without wanting to be held to a mechanism, toxic gases (e.g., ammonia) is likely adsorbed on the composites via three mechanisms: (i) intercalation between the graphene layers from GO, (ii) adsorption at the "interface" between the MOF segments and graphene layers where the dispersive forces are enhanced (the synergetic effect of the structure), (iii) hydrogen-bonding to the metal oxide clusters.

Methods of making the Nanocomposite Materials

In one embodiment, the invention relates to methods of making a nanocomposite material. The method comprises dispersing a graphite-based material in precursors of transition metal-organic framework (MOF) units. The nanocomposite material is formed by chemically linking the graphite-based material with the MOF units.

Examples of precursors of transition MOF units include precursors of HKUST-1. MOF-5 and MIL-100. Examples of precursors of MOF-5 include zinc hexahydrate and benzenedicarboxylate. Examples of precursors of HKUST-1 include copper nitrate hemipentashydrate and 1,3,5,-benzenetricarboxylatic acid.

The precursors of the transition MOF units are, for example, well-dissolved in a solvent along with graphite-based materials to form a mixture. The graphite-based materials can be in the form of graphite oxide (typically as a powder), graphite, and/or graphene. The relative amounts of the graphite-based materials and the MOF precursors depend on the desired functionality of the endproduct. The mixture is heated, and dried to form crystals.

EXAMPLES

Example 1

Enhanced Adsorption of Ammonia on MOF-5/GO Composites

In this example, MOF-5/GO nanocomposites were evaluated as ammonia removal media. Four composites with various GO contents (5, 10, 20 and 50 wt %) were synthesized and tested. The nanocomposites as well as the parent materials were analyzed before and after ammonia adsorption to characterize their surface and chemistry, and to understand the process of $NH_3$ adsorption/reactive adsorption.

Experimental

Materials

Graphite oxide was synthesized by oxidation of graphite (Sigma-Aldrich) using the Hummer's method. The details are described elsewhere in Panella et al. (*Adv. Mater.* 2005, 17, 538). MOF-5 was prepared by mixing zinc nitrate hexahydrate (10.4 g) and 1,4 benzenedicarboxylate (2 g) in N,N dimethylformamide (DMF, 140 mL) until complete dissolution of the solids. Then, the mixture was transferred into a round flask connected to a condenser and heated at 115-120° C. for 24 hours. After cooling, the supernate was removed and crystals deposited on the bottom of the flask were collected, washed with DMF, and immersed in fresh chloroform overnight. Chloroform was changed twice during two days. Finally, crystals were collected, placed inside a closed filtering flask connected to an aspirator used to create vacuum inside the flask, and heated at 130-135° C. for six hours. The resulting crystals were then kept in a dessicator.

The composite materials were prepared by dispersing GO powder in the well-dissolved zinc nitrate/BDC mixture. The resulting suspensions were subsequently stirred and subjected to the same synthesis procedure as for MOF-5. The added GO consists of 5 wt %, 10 wt %, 20 wt % and 55 wt % of the weight final material. The synthesized composites are referred to as MOF-5-GO1, MOF-5-GO2, MOF-5-GO3, and MOF-5-GO4, respectively.

$NH_3$ Breakthrough Dynamic Test

The laboratory designed dynamic test was used to evaluate $NH_3$ adsorption from gas streams (Leuch et al., *Carbon*, 2007, 45, 568). 1.5 $cm^3$ of the prepared samples (either the parent materials or the nanocomposites) was packed into a glass column and exposed to a flow of ammonia diluted in dry air. The concentration of ammonia was chosen equal to 1000 ppm and the total flow rate to 450 $mL.min^{-1}$. The breakthrough of $NH_3$ was monitored using an electrochemical sensor (Multi-Gas Monitor ITX system). The flow of ammonia was arbitrarily stopped at the breakthrough concentration of 100 ppm and the desorption process was then studied by purging the bed with the carrier air only (360 $mL.min^{-1}$). The adsorption capacity of each sorbent, in terms of mg of ammonia per g of adsorbent, was calculated by integration of the area above the breakthrough curve, considering the $NH_3$ concentration in the inlet gas, the flow rate, the breakthrough time, and the mass of sorbent used. A similar calculation was performed by integration of the area under the desorption curve to determine the amount of ammonia desorbed for each experiment. The letter E (E—Exhausted) is added to the name of the samples obtained after exposure to ammonia diluted in dry air.

pH

The pH of the samples before and after exposure to $NH_3$ was measured. The adsorbent powder (about 0.15 g) was stirred overnight with distilled water (7.5 mL) and then the pH of the suspension was recorded.

Sorption of Nitrogen

Nitrogen isotherms of the initial samples were measured at −196° C. using an ASAP 2010 (Micromeritics). Prior to each measurement, samples were outgassed at 120° C. Approximately 0.10 g of sample was used for these analyses. The surface area, $S_{BET}$, (BET method), the microporous volume, $V_{mic}$, (Dubinin-Radushkevitch method), the mesoporous volume, $V_{mes}$, the total pore volume, $V_t$, were calculated from the isotherms.

XRD

X-ray diffraction (XRD) measurements were conducted using standard powder diffraction procedures. Adsorbents were ground with DMF in a small agate mortar. The mixture was smear-mounted onto a glass slide and then analyzed by Cu $K_\alpha$ radiation generated in a Philips X'Pert X-ray diffractometer. A diffraction experiment was run on standard glass slide for the background correction.

Thermal Analysis

TG curves were obtained using a TA Instrument thermal analyzer. The samples (initial or exhausted) were exposed to an increase in temperature of 10° C.min$^{-1}$ from 30 to 1000° C. under a flow of nitrogen held at 100 mL.min$^{-1}$.

FT-IR Spectroscopy

Fourier transform infrared (FTIR) spectroscopy was carried out using a Nicolet Magna-IR 830 spectrometer using the attenuated total reflectance method (ATR). The spectrum was generated, collected 16 times and corrected for the background noise. The experiments were done on the powdered samples, without KBr addition.

Results

The ammonia breakthrough curves and desorption curves obtained on the materials were studied. An increase in the content of GO results in longer breakthrough times. Especially an enhancement is noticed when the amount of GO increased from 20 to 55%. Ammonia adsorption capacities calculated from those curves are listed in Table 1. The values are reported in mg per g of an adsorbent and in mg per cm$^3$ of an adsorbent. The former unit is important to understand and compare the process of adsorption for each material, while the second one is used for practical considerations since the size of the bed can be a limiting factor. Taking into account that one of the objectives is to identify the mechanism of ammonia adsorption on these new adsorbents, the amount adsorbed per unit mass of the materials is analyzed in detail. As seen from Table 1, GO exhibits good performance with an adsorption capacity of 55 mg.g$^{-1}$. This high capacity is linked to the acidic character of GO and the possibility of $NH_3$ intercalation between the graphene layers. On the contrary, adsorption on MOF-5 is very low and reaches only 6 mg.g$^{-1}$. This low efficiency is attributed to the absence of strong reactive sites able to retain ammonia, and a lack of strong dispersive forces due to the open porous network, and relatively large pore sizes present in MOF compounds. To give some prespective on the obtained capacity values, ammonia adsorption on common unmodified activated carbons and other carbonaceous materials usually falls in the range 1-20 mg.g$^{-1}$.

TABLE 1

Ammonia breakthrough capacities, amount desorbed, and surface pH for the parent and composite materials.

| sample | $NH_3$ breakthrough capacity [mg · g$^{-1}$ of material] | $NH_3$ breakthrough capacity [mg · cm$^{-3}$ of material] | "Hypothetical" $NH_3$ breakthrough capacity [mg · g$^{-1}$ of material] | $NH_3$ desorbed [mg · g$^{-1}$ of material] | pH initial | pH exhausted |
|---|---|---|---|---|---|---|
| GO-E | 56 | 37 | — | 0.9 | 2.47 | 5.53 |
| MOF-5-E | 6 | 3 | — | 0.5 | 5.64 | 5.80 |
| MOF-5-GO1-E | 7 | 3 | 8 | 0.5 | 6.09 | 6.10 |
| MOF-5-GO2-E | 22 | 12 | 12 | 1.6 | 5.62 | 5.72 |
| MOF-5-GO3-E | 38 | 21 | 16 | 1.4 | 6.13 | 6.92 |
| MOF-5-GO4-E | 82 | 43 | 33 | 1.5 | 5.89 | 7.26 |

The adsorption capacity of the composites increases by increasing the GO content and is always higher than the one of MOF-5 alone. It increases more than 10 times with an increase in the GO contents from 5 to 55%. For the MOF-5-GO4 sample, ammonia uptake is particularly high and even exceeds the one observed for GO. Table 1 also lists the hypothetical adsorption capacity of the composites assuming the physical mixture of GO and MOF-5 and taking into account the percentage of each component. The latter values are almost twice lower than the actual values. This is an indication of synergy between GO and MOF-5. The synergetic effect observed must result from the presence of a significant pore volume in the composites where dispersive forces are enhanced as hypothesized earlier. Ammonia molecules are thus retained via physisorption in the pore space located between the MOF-5 "segments" and the graphene layers.

The adsorption capacity increases almost linearly with an increase in the GO content. Nevertheless, an indication of the change in the slope with higher GO contents suggests that further increase in the amount of GO would not provide the beneficial effects. Analyzing the structure of the composites in details, it was found that an increase in the GO content results in a greater distortion of the MOF-5 structure.

Since the performance of materials as ammonia adsorbents is evaluated not only based on the amount of $NH_3$ adsorbed but also on the strength of the adsorption process, the amount of ammonia desorbed during purging with air is also analyzed. The progressive desorption of ammonia from the adsorbent surface is not a desired feature and efforts should be done to prevent it. The amount of ammonia desorbed by purging the bed with air is directly related to the area under the desorption curve. The calculated amounts of ammonia desorbed are listed in Table 1 for the parent and composite materials. For the composites, between 2 and 7 wt % of ammonia is desorbed (except for MOF-5-GO1: 11%). These values are in the range of the ones obtained with the parent materials, and indicate that most of the ammonia adsorbed is strongly retained on the surface. This performance is much better than that obtained for modified activated carbons.

To find the specific sites for ammonia adsorption and to analyze an effect of ammonia retention on the texture of the materials, the porosity of all samples before and after exposure to ammonia was studied. The parameters of porous structure calculated from nitrogen adsorption isotherms are listed in Table 2. Isotherms for most of the composite materials are reported here to allow an identification of the changes occurring after ammonia adsorption. GO is not shown because it is considered as a non-porous material. The $N_2$ isotherms before exposure to ammonia have a type-I shape indicative of their microporous structure. After exposure to ammonia, isotherms of MOF-5, MOF-5-GO1 and MOF-5-GO2 remain almost unchanged. For MOF-5-GO3, the shape of the isotherm is preserved but the amount of $N_2$ adsorbed is significantly decreased. Finally, for MOF-5-GO4, the shape of the isotherm is completely modified (type IV) and indicates the formation of mesopores in the material. The changes observed for MOF-5-GO3-E suggest that the structure of the MOF-5 component is preserved but with significant distortion. For MOF-5-GO4-E, the shape of the isotherm rather indicates the collapse of the MOF-5 structure.

TABLE 2

Parameters of porous structure calculated from nitrogen isotherms for the parent and composite materials before and after exposure to ammonia.

| Sample | $S_{BET}$ ($m^2 \cdot g^{-1}$) | $V_t$ ($cm^3 \cdot g^{-1}$) | $V_{meso}$ ($cm^3 \cdot g^{-1}$) | $V_{mic}$ ($cm^3 \cdot g^{-1}$) | $V_{mic}/V_t$ |
|---|---|---|---|---|---|
| MOF-5 | 793 | 0.408 | 0.023 | 0.385 | 0.94 |
| MOF-5-E | 739 | 0.399 | 0.010 | 0.389 | 0.97 |
| MOF-5-GO1 | 706 | 0.365 | 0.024 | 0.341 | 0.93 |
| MOF-5-GO1-E | 710 | 0.365 | 0.024 | 0.341 | 0.93 |
| MOF-5-GO2 | 806 | 0.416 | 0.028 | 0.388 | 0.93 |
| MOF-5-GO2-E | 807 | 0.415 | 0.027 | 0.388 | 0.93 |
| MOF-5-GO3 | 603 | 0.325 | 0.037 | 0.288 | 0.89 |
| MOF-5-GO3-E | 475 | 0.254 | 0.025 | 0.229 | 0.90 |
| MOF-5-GO4 | 742 | 0.399 | 0.002 | 0.397 | 0.99 |
| MOF-5-GO4-E | 93 | 0.211 | 0.168 | 0.043 | 0.20 |

As seen from Table 2, MOF-5 surface area is about 800 $m^2 \cdot g^{-1}$ which is small compared to the 2,000-3,500 $m^2 \cdot g^{-1}$ reported by others. Nevertheless, it has been shown that slight changes in the preparation method (temperature, precursor, solvent, pH . . . ) could have a significant impact on the morphology and porosity of the resulting materials. This can explain the rather small surface area of the samples and the ones found by other researchers. Pores are mainly in the microporous range (more than 90%) which can be a valuable asset for the retention of small molecules like ammonia. The parameters of porous structure for the composites are similar to the ones observed for MOF-5. The nanocomposites have a surface area between 600 and 800 $m^2 \cdot g^{-1}$ and show a predominance of micropores. A decrease in the surface area and volume of pores observed for some composites compared to MOF-5 must be related to an increase in the distortion of the MOF-5 structure owing to the presence of GO. The absence of correlation between the GO content and the extent of that decrease in porosity must be related to the way the composites are formed and the synergy between the components. After exposure to ammonia, no significant changes in the textural parameters are observed for MOF-5, MOF-5-GO1 and MOF-5-GO2. In the case of MOF-5-GO2, the result is surprising. The plausible explanation is that, a significant part of the ammonia adsorbed on this sample was removed during the degassing treatment performed by heating the samples at 120° C. before $N_2$ sorption analyses. For the composites with the higher GO contents, the porosity significantly decreased after exposure to ammonia. The surface areas measured are only 475 $m^2 \cdot g^{-1}$ and 93 $m^2 \cdot g^{-1}$ for MOF-5-GO3-E and MOF-5-GO4-E, respectively. This decrease can be explained by the effects of the high amount of ammonia retained on the surface. Due to the sensitivity of MOFs to $NH_3$, its presence in a large quantity likely leads to a distortion in the morphology of the MOF-5 component. This finally causes the collapse of the MOF-5 structure. The MOF-5 structure also collapsed when MOF-5 was analyzed by $N_2$ sorption after exposure to humid air. Indeed, results showed that the porosity of the material is completely lost as in the case of MOF-5-GO4-E.

It seems that $NH_3$ molecules have the same effect on the stability of MOF-5 as water molecules have by affecting the stability of the framework. Water leads to the destruction of MOF-5 via the "replacement" of oxygen atoms in $ZnO_4$ tetrahedron by oxygen atoms from water, and by hydrogen bonding between hydrogen atoms in water and oxygen atoms in $ZnO_4$ tetrahedron. The fact that at some point, ammonia causes the collapse of MOF-5 structure is not surprising considering the similarity between ammonia and water molecules in terms of chemistry. As water molecule, ammonia can induce the formation of hydrogen bonds between its hydrogen atoms and oxygen atoms in $ZnO_4$ tetrahedron. This phenomenon would represent another way in which ammonia can be retained on the composites.

To check the hypothesis about the effect of ammonia on the stability of the MOF-5 component in the composites and its similarity to the impact of water, the materials were analyzed by X-ray diffraction. The spectra of the parent and composite materials before and after exposure to ammonia are compared to the one of MOF-5 exposed to humid air. GO spectrum shows a peak at 2 Θ 9.3° indicating an interlayer distance of 9.5 Å. This distance is reduced to 8.5 Å after exposure to ammonia. Indeed, running adsorption in dry air causes the progressive removal of the water present in the interlayer space and thus the subsequent decrease of this interlayer distance. Moreover, purging the bed with dry air during the desorption likely leads to the removal of a part of the ammonia intercalated between the layers. MOF-5 diffraction pattern is in agreement with the ones found for well-defined MOF-5 crystals. The diffraction patterns for the composite materials are presented here for the sake of comparison with the structure of the materials after exposure to ammonia or water. The diffraction patterns of the composite materials are similar to the one observed for MOF-5, which indicates that the MOF-5 structure is preserved. Nevertheless, a splitting appears in the peak at 2 Θ about 9.7° and becomes more pronounced when the GO content increases. This splitting has been encountered by other authors who attributed it to a distortion in the cubic arrangement of MOF-5. All of this suggests that the GO component in the composites induces a distortion in the structure of the MOF-5 component. The latter feature can contribute to the synergetic effect and the trend observed in the ammonia adsorption capacity when the GO content increases. Indeed, when the MOF-5 component is in a predominant quantity, an increase in the GO content causes an increase in the dispersive forces required to retain NH$_3$ compared to MOF-5 alone. Moreover, GO layers provide additional sites for ammonia adsorption. Nevertheless, with high content of GO, more distortion in the structure of MOF-5 component is observed and it eventually leads to a decrease in the amount of ammonia adsorbed. After exposure to ammonia, the splitting of the peak at 2 Θ 9.7° becomes more pronounced. For MOF-5-GO3-E, this peak is even slightly shifted towards lower angles but the overall pattern is preserved. On the contrary, for MOF-5-GO4-E, the spectrum is completely modified and shows features similar to the ones from the spectrum of MOF-5 exposed to humid air. These observations indicate once again that ammonia retained on the composites leads to a distortion of the structure of the MOF-5 component. This distortion is the greatest for MOF-5-GO3-E and it evolves to a complete collapse of the structure for MOF-5-GO4-E as the one observed when MOF-5 is exposed to water.

Further confirmation of the effect of ammonia on the structure of MOF-5 component is provided by FT-IR spectra. The spectra of MOF-5 and the composites before exposure to ammonia look rather similar. The asymmetric stretching of carboxylic groups in BDC is detected at 1510 cm$^{-1}$ and 1580 cm$^{-1}$, and the symmetric stretching of carboxylic groups in BDC is observed at 1390 cm$^{-1}$. In the region 1300-700 cm$^{-1}$, several bands are observed and they are assigned to the out-of-plane vibrations of BDC. After adsorption of ammonia, the spectra of MOF-5 and MOF-5-GO1 and MOF-5-GO2 do not change. However, a slight modification is observed especially around 1600 cm$^{-1}$ for MOF-5-GO3. For MOF-5-GO4, the spectrum is completely changed and resembles the one of MOF-5 exposed to humid air. More precisely, the initially broad and overlapping bands around 1600 cm$^{-1}$ now appear as a single peak. Also a new band at 655 cm$^{-1}$ appears. All of this shows that ammonia tends to destroy the MOF-5 structure. However, a difference in the spectrum of MOF-5-GO4-E and the one of MOF-5 exposed to humid air is seen: a small band at 1680 cm$^{-1}$ present for MOF-5 exposed to humid air is not observed for MOF-5-GO4-E. This band is related to the presence of protonated carboxylic groups formed when water is present.

By testing the thermal stability of the materials before and after exposure to ammonia, further identification of change in chemistry caused by ammonia adsorption and thus the possible presence of complexes formed by reactive adsorption can be assessed. DTG curves for the parent and composite materials were plotted. The features of GO DTG curve can be summarized as follows: physically adsorbed water is removed at 100° C., followed by the decomposition of epoxy groups at ~200° C. Between 250 and 350° C. carboxylic groups are decomposed and then decomposition of phenolic/OH groups as well as ethers takes place. MOF-5 DTG curve shows a sharp peak at 460° C. indicative of the decomposition of MOF-5 and gradual transition to ZnO. This temperature is in agreement with the values reported in the literature and indicates the good stability of the material. The increase in the intensities of the peaks representing weight loss at temperatures higher than 800° C. is likely due to the reduction of ZnO by carbon. Even though the DTG curves for the composites exhibit similar peaks to the ones of MOF-5, a small peak around 200° C. is a new feature. It can either correspond to strongly bound water or it can be due to the decomposition of epoxy groups from the GO component. However, as the intensity of that peak does not change significantly with the content of GO, the first hypothesis seems to be more plausible. Moreover, it was proposed that epoxy groups of GO contribute to the formation of composites by involvement of their oxygen in the structure of ZnO$_4$. The absence of the intense peak related to epoxy groups decomposition supports this mechanism of composite formation. After exposure to ammonia, the shape of the DTG curves for MOF-5-GO1 and MOF-5-GO2 is not changed. On the contrary, for MOF-5-GO3 and especially for MOF-5-GO4, exposure to ammonia significantly alters the stability of the materials. The sharp peak initially located at 460° C. appears broader and at lower temperature. These observations suggest again that the MOF-5 structure has been significantly altered in those two samples after ammonia adsorption, which supports the results of porosity study and X-ray diffraction. For MOF-5-GO4-E, a small and broad peak is detected around 300° C. It might be related to a complex formed via the reactive adsorption of ammonia on the adsorbent surface. Nevertheless, data are not sufficient at this stage for a precise assignment for this peak.

Considering all the above findings, ammonia is likely adsorbed on the composites via three mechanisms: (i) intercalation between the graphene layers from GO as already observed in previous studies, (ii) adsorption at the "interface" between the MOF-5 segments and graphene layers where the dispersive forces are enhanced (the synergetic effect of the structure), (iii) hydrogen-bonding to the zinc oxide clusters as suggested by the distortion in the MOF-5 structure observed in the samples analyses. Based on this, as well as on the structure of the composites described elsewhere, a schematic view of these three mechanisms of reactive adsorption is proposed in FIG. 1 in which ammonia molecules are represented by yellow circles.

The results showed that the composites of MOF-5 and GO provide strong dispersive forces enhancing the retention of small molecules. These forces exist at the "interface" between the MOF-5 segments and the graphene layers and they account for a synergetic effect in the adsorption of ammonia compared to the parent materials. Owing to this synergy, the materials show good performance as ammonia adsorbents. Another hypothesized way in which ammonia is retained on the surface of the composites is via hydrogen bonding with the zinc oxide clusters from the MOF-5 component. However, due to these hydrogen-bonding interactions, when a large quantity of ammonia is adsorbed, a progressive destruction of the structure of MOF-5 in the composites occurs. This alteration is similar to the one detected when MOF-5 is exposed to water. These applications usually take place ambient conditions and thus with a range of moisture present in air.

Example 2

MOF5-GO Composites: Combining the Uniqueness of Graphene Layers and Framework of MOF Graphite oxide (GO)/metal-organic framework (MOF-5) nanocomposites were synthesized with various ratios of the two components. The composites have a unique layered sandwich-like structure where GO units divide the MOF-5 units. A possible scenario for the formation of such structures is the involvement of linkages between epoxy groups of distorted graphene layers of GO and zinc oxide building units of MOF-5. An increase in the content of GO leads to a greater distortion of the MOF-5 cubic structure and visible changes in the texture of nanocomposites. The materials are predominantly microporous with sizes of pores defined by the cavities of MOF-5 units. Moreover, specific combination and synergy between GO and MOF-5 units also result in the formation of a unique porosity characteristic of the nanocomposites.

Experimental

Materials

Graphite oxide was synthesized by oxidation of graphite (Sigma-Aldrich) using the Hummer's method. Briefly, graphite powder (10 g) was stirred with cool concentrated sulfuric acid (230 mL at 0° C.). Then, potassium permanganate (30 g) was added to the suspension slowly to prevent a rapid rise in temperature (less than 20° C.). The reaction mixture was then cooled to 2° C. After removal of the ice-bath, the mixture was stirred at room temperature for 30 min. Distilled water (230 mL) was slowly added to the reaction vessel to keep the temperature under 98° C. The diluted suspension was stirred for an additional 15 min and further diluted with distilled water (1.4 L), before adding hydrogen peroxide (100 mL). The mixture was left overnight. GO particles, settled at the bottom, were separated from the excess liquid by decantation followed by centrifugation. The remaining suspension was transferred to dialysis tubes (MW cutoff 6,000-9,000). Dialysis was carried out until no precipitate of $BaSO_4$ was detected by addition of $BaCl_2$. Then, the wet form of graphite oxide was centrifuged and freeze-dried. A fine brown powder of the initial graphite oxide was obtained. The resulting material is referred to as GO. MOF-5 was prepared as described in Example 1.

The composite materials were prepared by dispersing GO powder in the well-dissolved zinc nitrate/BDC mixture. The resulting suspensions were subsequently stirred and subjected to the same synthesis procedure as for MOF-5. The added GO consists of 5 wt %, 10 wt % or 20 wt % weight final material. The synthesized composites are referred to as MOF-5-GO1, MOF-5-GO2 and MOF-5-GO3, respectively.

Textural Characterization

Textural characterization was carried out by measuring the $N_2$ adsorption isotherms at −196° C. Before the experiments, the samples were outgassed under vacuum at 120° C. The isotherms were used to calculate the specific surface area, $S_{BET}$, total pore volume, $V_{tot}$ volume of micropores, $V_{mic}$, volume of mesopores, $V_{mes}$, and pore size distributions. The volume of pores, and surface in pores larger than 10 Å were obtained using density functional theory (DFT).

Electron Microscopy (SEM/EDAX)

Scanning electron microscopy was performed on a Zeiss Supra 55 instrument. The instrument has a resolution of 5 nm at 30 kV. Scanning was performed on a sample powder previously dried and sputter coated with a thin layer of carbon to avoid charging. EDAX analyses were done on the same instrument with samples previously dried and coated with gold and palladium (to avoid charging and allow carbon content determination more accurately). From EDAX analyses, the content of elements on the surface was calculated and the maps of the elements derived.

X-Ray Diffraction

X-ray diffraction (XRD) measurements were conducted as described in Example 1.

Results

Since in the nanocomposites materials, MOF-5 represents the major component, a predominance of MOF-5 structure features is seen on the X-ray diffraction patterns of the nanocomposites. Of course, it should only happen when MOF-5 synthesis in the presence of GO does not prevent the formation of linkages between the zinc oxide and BDC. The major diffraction pattern of MOF-5 is preserved in the composites and this pattern is in agreement with those previously reported for MOF-5. For GO, the peak at 2 Θ about 9.29° represents the interlayer distance of 9.5 Å. For MOF-5-GOn (n=1, 2 or 3) nanocomposites, the sharpness of the peak at 2 Θ about 9.7° is slightly reduced and the splitting of that peak is noticed. This splitting increases in its visibility with an increase in the content of GO. A similar feature was observed by Lillerud and coworkers on MOF-5. They attributed it to a distortion of the cubic symmetry. Finding it for the instant composites indicates that the presence of GO in the sample increases the distortion in the MOF-5 cubic arrangement. There are additional constraints in the degrees of freedom during synthesis caused by the presence of GO, and they increase with an increase in the content of GO. Other interesting features, quite unique for MOF-5-GO composites, are sharp peaks between 2 Θ 30 and 40°. They are much less sharp for MOF-5 and almost not present for MOF-5-GO2. Thus they must represent differences in the building units of MOF-5-GO2 and the two other composites.

Figure 2:
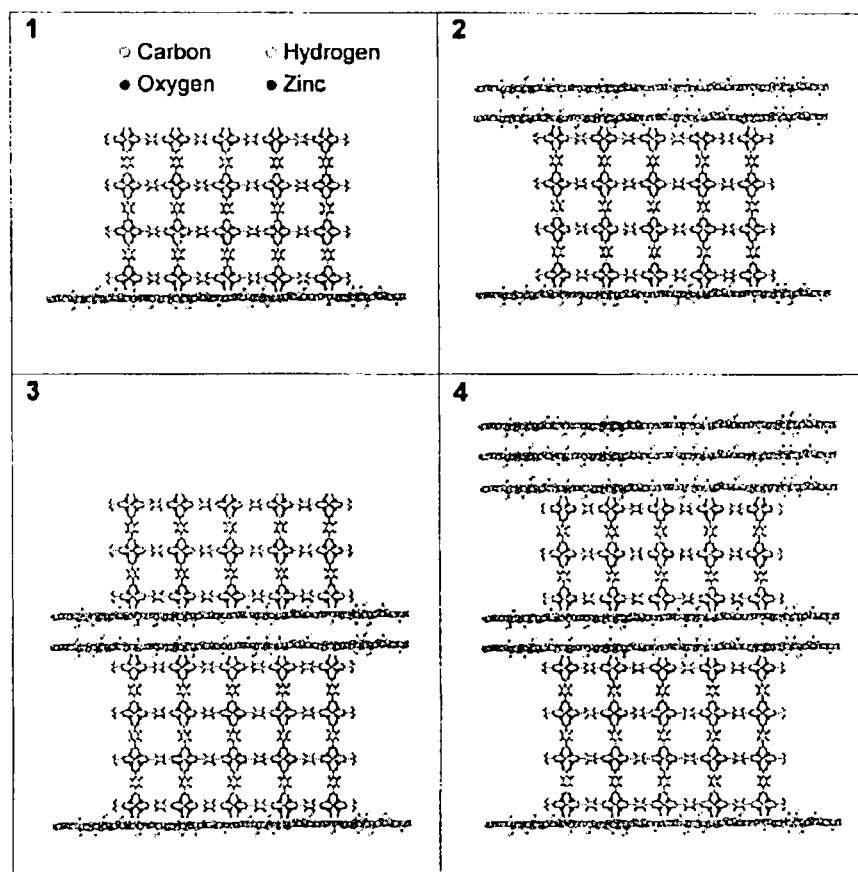
FIG. 2. Schematic view of the steps (1-4) of the nanocomposite (MOF-5-GO1) formation. In black: C atoms in MOF-5, in green: C atoms in GO, in blue: Zn atoms, in red: O atoms, in grey: H atoms.

The texture of the nanocomposites can be observed on SEM micrographs. For comparison, micrographs for GO and MOF-5 were also analyzed. In the latter sample, the cubic crystals of MOF-5 are clearly visible with some traces of amorphous phase. GO is seen as dense agglomerates/flakes of graphene sheets stacked together by dispersive forces. On the other hand, the agglomerates of MOF-5-GO1 nanocomposite look totally different. They consist of regular square-shaped thin platelets of about 500×50 nm stacked together in an organized way. Taking into account the differences in the texture between MOF-5-GO1, MOF-5 and GO, it is plausible to assume that thin agglomerates of graphene layers act as dividers located between the thin platelets of MOF-5. This leads to the formation of that sandwich-like structure. For MOF-5-GO2, although some indication of the layered structure can be seen, the edges of the platelets are much less sharp and more GO likely interferes with the MOF-5 crystallization pattern. Those changes are even more visible for MOF-5-GO3 where 20 wt % GO is present. Owing to the pronounced differences in the densities of both components in MOF-5-GO3, the physical contact of both phases must be extended and MOF-5 crystallizes as about 50 nm in diameter worm-like structures connected to the edges on graphene platelets. The EDAX element maps of the nanocomposites show that carbon, oxygen and zinc are well-dispersed on the surface, which suggests that for all composites, GO and MOF-5 interact to form new materials of homogenous structure and chemistry. Taking into account the chemistries of both components of nanocomposites, the building process of the ordered structure of MOF-5-GO1 is hypothesized. A schematic and simplified version of the mechanism is proposed in FIG. 2. In a first step, MOF-5 "blocks" attach to a graphene layer by reactions with epoxy groups on GO. This can happen based on the analysis of water interactions with MOF-5 presented by Greathouse and Allendorf. According to them, a replacement of an oxygen atom in $ZnO_4$ tetrahedron by oxygen atom from water is a very important step leading to the decomposition of MOF-5 by water. In the instant case, it is assumed that oxygen atoms in epoxy groups on GO play the same role as oxygen atoms in water. However, no collapse of MOF-5 structure occurs owing to the limitations in the number of epoxy groups and their restricted spatial location compared to free molecules of water. Hydrogen bonding between hydrogen atom from hydroxyl groups on GO and oxygen atoms in $ZnO_4$ tetrahedron might increase the degree of interaction between graphene layers and MOF-5 crystal. Hydrogen bonding between water molecules and $ZnO_4$ tetrahedron was also described by Greathouse and Allendorf. In the subsequent steps of the nanocomposite building process, an alternation between attachment of graphene layers and MOF-5 "blocks" happens. The mechanism of the structure formation might be different for MOF-5-GO3. In this sample, more GO is present than for the other two composites and consequently the amount of carboxylic groups on the edges of the layers is higher. Those groups must have a greater affinity for zinc oxide tetrahedron than epoxy groups have. Attachment of MOF-5 "blocks" on the edges of the GO layers might accompany the above described mechanism or be a preferred mechanism, leading to the formation of worm-like structures as seen in SEM images.

The textural homogeneity is reflected on nitrogen adsorption isotherms. They have well-defined Langmuir-type shape indicating microporosity and pores of uniform sizes, which is in agreement with the structural model of cavities in MOF-5 in which the passage of spheres of diameter up to 8.0 Å have been defined. From these isotherms, the parameters of porous structure were calculated. They are collected in Table 3. In this Table, also reported are the hypothetical values of the surface areas and pore volumes assuming the physical mixture of the components. The surface area is reported only for the sake of comparison since for such materials as MOFs, having an open framework, reporting the pore volume seems to be more appropriate because fewer assumptions are used for its calculation. GO is nonporous from the point of view of nitrogen used as a molecular probe. It is important to notice that the surface area of MOF-5 is smaller than 3000-3500 $m^2 \cdot g^{-1}$ reported elsewhere. Nevertheless, surfaces of similar magnitude were reported by Huang and coworkers, and Panella and coworkers. The difference in the surface area can be related to the way of outgassing during preparation and thus the completeness of solvent removal. Other factors such as the temperature at which crystals were formed were also indicated as potentially affecting the porosity.

materials is progressively modified and its porosity decreased when the amount of GO in the composite increases. It is hypothesized that the formation of such structure occurs via interactions between epoxy groups from graphene layers and zinc oxide clusters from MOF-5.

Example 3

MOF-5/GO Nanocomposites: Evaluation as Adsorbents of Ammonia

Metal-organic framework (MOF-5)/graphite oxide (GO) composite was synthesized using solvothermal synthesis route. The parent materials (MOF-5 and GO) and the nanocomposite were characterized using X-ray diffraction, SEM, TEM, FTIR and adsorption of nitrogen. They were also tested as adsorbents of ammonia in dynamic conditions. The composite material obtained had a unique layered texture with a preserved structure of MOF-5 and GO. When tested as ammonia adsorbent, the composite showed synergy enhancing the adsorption capacity in comparison with the hypothetical physical mixture of the components. Although the removal capacity was high in the presence of moisture, water had a detrimental effect on the chemistry of materials and destroyed their porous framework. This caused ammonia retained on the surface to be progressively desorbed from the materials when the samples were purged with air.

TABLE 3

Parameters of porous structure calculated from adsorption of nitrogen and hypothetical values (H) derived assuming the physical mixture of the nanocomposite components.

| Sample | $S_{BET}$ [$m^2 \cdot g^{-1}$] | $V_{tot}$ [$cm^3 \cdot g^{-1}$] | $V_{meso}$ [$cm^3 \cdot g^{-1}$] | $V_{mic}$ [$cm^3 \cdot g^{-1}$] | $S_{BET}H$ [$m^2 \cdot g^{-1}$] | $V_{tot}H$ [$cm^3 \cdot g^{-1}$] | $V_{mic}H$ [$cm^3 \cdot g^{-1}$] |
|---|---|---|---|---|---|---|---|
| GO | nil | nil | nil | nil | — | — | — |
| MOF-5 | 793 | 0.408 | 0.023 | 0.385 | — | — | — |
| MOF-5-GO1 | 706 | 0.365 | 0.024 | 0.341 | 753 | 0.388 | 0.366 |
| MOF-5-GO2 | 806 | 0.416 | 0.028 | 0.388 | 714 | 0.367 | 0.347 |
| MOF-5-GO3 | 603 | 0.325 | 0.037 | 0.288 | 634 | 0.327 | 0.308 |

The composites have a high volume of micropores and less than 10% total pore volume in mesopores. The latter increases with an increase in the content of GO. The most developed porosity is found for MOF-5-GO2 which is an interesting finding since its texture, as seen from SEM micrograph, is considered as "in between" the ones for the samples formed from 5 and 20 wt % of GO. Apparently 10 wt % GO results in the most porous materials with about 12% increase in the parameters of the porous structure compared to the porosity of the hypothetical physical mixture of the components. For the other two materials, especially for MOF-5-GO3, the measured volume of micropores is less than the hypothetical one. This can be related to the distortion in the MOF-5 cubic arrangement which was observed on X-ray diffraction. This was also reflected in the texture of the composite. The lack of the well-defined trend in the porosity of the composites can be the result of the small differences in the synthesis conditions.

Nanocomposites containing graphite oxide and metal-organic framework (MOF-5) have been prepared with various ratios of the two components. The structure of the precursors is preserved in the composites. The latter ones show a well-defined and porous structure where graphene layers from GO alternate with layers of MOF-5. The arrangement of these Experimental Synthesis of Materials Graphite oxide was synthesized as described in Example 2. MOF-5 was prepared as described in Example 1.

The composite material was prepared by dispersing GO powder in the well-dissolved zinc nitrate/BDC mixture. The resulting suspension was subsequently stirred and subjected to the same synthesis procedure as for MOF-5. The added GO consists of 5 wt % weight final material. The synthesized composite is referred to as MOF-5-GO.

Methods

Ammonia Adsorption

Adsorption capacity for removal of ammonia was assessed by carrying out dynamic tests at room temperature. In this process, a flow of ammonia diluted in air went through a fixed bed of an adsorbent sample. The total flow rate of the inlet gas was 450 mL/min with an ammonia concentration of 1000 ppm. The adsorbent's bed contained about 1.5 cc of the adsorbent powder (GO, MOF-5 or MOF-5-GO) packed into a glass column. The size of the bed was 20 mm (high)×10 mm (diameter). The conditions were chosen to accelerate the time of the test and limit the exposure of the sensor which lifetime is relatively short. The ammonia concentration in the outlet gas was measured using a Multi-Gas Monitor ITX system. The adsorption capacity of each sample was then calculated in mg per g of sorbent, as the difference between the inlet and outlet concentrations multiplied by the inlet flow rate, the breakthrough time and the ammonia molar mass in the experimental conditions. To evaluate the influence of water, the experiments for all carbon samples were performed with a flow of ammonia gas diluted either in dry air (ED) or in moist air (70% humidity) (EM). On all samples, the desorption of ammonia was evaluated when exposed to 360 mL/min of the carrier air.

Textural Characterization

Textural characterization was carried out by measuring the $N_2$ adsorption isotherms at $-196°$ C. Before the experiments, the samples were outgassed under vacuum at 120° C. The isotherms were used to calculate the specific surface area, $S_{BET}$, total pore volume, $V_t$, volume of micropores, $V_{mic}$, volume of mesopores, $V_{mes}$, and pore size distributions. The latter was calculated using the density functional theory (DFT).

Surface pH

The pH of a sample suspension provides information about the acidity and basicity of the surface. About 0.15 g of the initial and exhausted MOF-5, GO or MOF-5-GO powder was added to 7.5 mL of distilled water. The suspension was stirred overnight to reach equilibrium before recording the pH.

SEM/EDAX

Scanning electron microscopy was performed as described in Example 2.

TEM

Transmission electron microscopy (TEM) was performed on a Zeiss EM 902 instrument. The microscope has a line resolution of 0.34 nm and a point resolution of 0.5 nm and operates in normal diffraction and low dose modes at 50 or 80 kV. Analyses were performed after the samples were resuspended in ethanol.

XRD

X-ray diffraction (XRD) measurements were conducted as described in Example 1.

FTIR

Fourier transform infrared (FTIR) spectroscopy was carried out as described in Example 1.

Results

Metal-organic frameworks or graphite oxides have a distinct structure, which provides fingerprints of their textural and chemical nature. To ensure that the MOF-5-GO composite has the elements of both components, the X-ray diffraction patterns were analyzed. For GO, the well-defined peak at 2 Θ about 9.29° represents an interlayer distance of 9.50 Å. For MOF-5, various sharp diffraction peaks are seen which are characteristic of this material structure and are in agreement with the data published in the literature. The XRD pattern of the nanocomposite does not differ significantly from that for MOF-5. Only the sharpness of the peak at 2 Θ about 9.7° is slightly reduced and the splitting of that peak is noticed. This split was observed by Lillerud and coworkers on MOF-5 and attributed to a distortion of the cubic symmetry. Finding it for the composite suggests that presence of GO in the sample increases the distortion in the MOF-5 cubic arrangement, owing to additional constraints in the degrees of freedom during synthesis. Nevertheless, X-ray analyses indicate that the major structural and chemical features of MOF-5 are preserved in MOF-5-GO. The predominant features of MOF-5 are expected since it consists of 95 wt. % the nanocomposite content.

The texture of the materials was studied on SEM micrographs. For MOF-5, besides the well-defined cubic crystals, some remains of an amorphous phase were distinguished. The particles of GO looked very dense with the layers stacked together as a result of dispersive forces and strong specific interactions between the surface groups on the graphene-like layers. On the other hand, MOF-5-GO exhibited totally different surface features. The layers of sandwich-like structures were clearly seen and the regular structure of layers suggests that they might be layers of MOF-5 crystallites separated by the layers of GO. In spite of the fact that only 5% wt GO was added during the MOF-5 synthesis, its effect on the texture of materials was very pronounced. In the synthesis, crystallites of similar sizes were formed and then restacked into larger particles with GO layers acting as dividers. The differences in the texture between MOF-5-GO composite, MOF-5 and GO precursors were also visible on TEM micrographs. On MOF-5-GO, ordered layered units with random orientation could be distinguished. It is hypothesized, taking into account the chemistries of both components of nanocomposites, that the building process of the ordered structure of MOF-5-GO is based on attachments of MOF-5 "blocks" to a graphene layer by reactions with epoxy groups on GO. This follows the analysis of water interactions with MOF-5 presented by Greathouse and Allendorf where a replacement of an oxygen atom in $ZnO_4$ tetrahedron by oxygen atom from water is a very important step leading to the decomposition of MOF-5 by water. It is believed that oxygen atoms in epoxy groups on GO play the same role as oxygen atoms in water. In the subsequent steps of the nanocomposite building process, an alternation between attachment of graphene layers and MOF-5 "blocks" takes place.

The nitrogen adsorption isotherms measured on MOF-5 and MOF-5-GO exhibit a typical Langmuir-type shape suggesting the predominant microporosity. The surface of GO is inaccessible for the nitrogen molecule and thus this material is considered as nonporous. The parameters of porous structure calculated from these isotherms are presented in Table 4. Although the surface area of MOF-5 is smaller than 3,000-3,500 $m^2/g$ observed for some MOF-5, surfaces of similar magnitude to the instant material were reported by Huang and coworkers, and Panella and coworkers. This low surface area can be related to the way of outgassing during the preparation and thus the completeness of solvent removal. The solvent used to prepare the materials as well as the temperature at which crystals were formed might also have an influence on their resulting porosity. The materials obtained are predominantly microporous with pores between 5 and 10 Å, which is in agreement with the structural model of cavities in MOF-5 in which the passage of spheres of diameter up to 8.0 Å have been defined. Pores with sizes between 16.0 and 23.5 Å are also found for the instant materials and they might be due to a distortion in the structure of MOF-5. When the nanocomposite is formed, the structural parameters decrease of about 10%, and the pore size distribution is preserved. Results for pore size distributions (PSDs) must be considered with caution since the pore model used for DFT calculation reflects the slit-shaped pores of carbonaceous materials. Nevertheless, since the same model is used for the series of materials the trends in PSDs can be analyzed.

TABLE 4

Parameters of porous structure calculated from nitrogen adsorption isotherms.

| Sample | $S_{BET}$ [$m^2/g$] | $V_t$ [$cm^3/g$] | $V_{meso}$ [$cm^3/g$] | $V_{mic}$ [$cm^3/g$] | $V_{mic}/V_t$ |
|---|---|---|---|---|---|
| MOF | 793 | 0.408 | 0.023 | 0.385 | 0.94 |
| MOF-ED | 739 | 0.399 | 0.010 | 0.389 | 0.97 |
| MOF-EM | 10 | 0.057 | 0.052 | 0.005 | 0.09 |

TABLE 4-continued

Parameters of porous structure calculated from nitrogen adsorption isotherms.

| Sample | $S_{BET}$ [m$^2$/g] | $V_t$ [cm$^3$/g] | $V_{meso}$ [cm$^3$/g] | $V_{mic}$ [cm$^3$/g] | $V_{mic}/V_t$ |
|---|---|---|---|---|---|
| MOF-GO | 706 | 0.365 | 0.024 | 0.341 | 0.93 |
| MOF-GO-ED | 710 | 0.365 | 0.024 | 0.341 | 0.93 |
| MOF-GO-EM | 8 | 0.025 | 0.021 | 0.004 | 0.16 |

The ammonia adsorption capacities calculated from the breakthrough curves in mg per gram of the materials and in mg per unit volume of the adsorbent bed and the surface pH values for the initial and exhausted samples are summarized in Table 5. In this table, also are listed the capacities calculated assuming the physical mixture of the adsorbents (5 wt % GO and 95 wt % MOF-5). Even though the capacity in moist conditions on the MOF-5-GO is smaller than that on GO, the value obtained is about 12% greater than that expected when the structural synergy between the components of the nanocomposite does not exist. High adsorption on GO was explained by interactions of ammonia with acidic groups and its intercalation between the distorted graphitic layers. In dry air, the performance of MOF-5 is very poor and the capacity measured is consistent with the one reported by Yaghi et al. That low capacity is a result of the lack of strong chemical interactions between NH$_3$ and MOF compound and relatively large pores compared to the size of ammonia molecule (3 Å). The much higher capacity in wet conditions must be related to adsorption of large quantities of water on MOF-5 and dissolution of ammonia in the water present in the pore space. Another possible scenario is a change in the mechanism of adsorption caused by formation of ammonium ions simultaneously with changes in the chemistry of materials caused by water. The low capacity of the composite at dry conditions is governed by the behavior of the predominant phase of MOF-5. The presence of GO in the composite slightly increases the performance but the analysis is difficult owing to a very short breakthrough time.

TABLE 5

Measured ammonia breakthrough capacity, calculated hypothetical capacity and the surface pH for the initial and exhausted samples.

| | NH$_3$ Breakthrough capacity | | Calculated hypothetical capacity | pH | |
|---|---|---|---|---|---|
| sample | [mg/g of material] | [mg/cm$^3$ of material] | [mg/g of material] | initial | exhausted |
| GO-ED | 55.5 | 36.9 | — | 2.47 | 6.24 |
| GO-EM | 61.0 | 39.8 | — | 2.47 | 6.66 |
| MOF-ED | 5.9 | 2.9 | — | 5.64 | 5.80 |
| MOF-EM | 42.5 | 23.0 | — | 5.64 | 6.63 |
| MOF-GO-ED | 6.9 | 3.3 | 8.4 | 6.09 | 6.10 |
| MOF-GO-EM | 53.3 | 28.8 | 43.4 | 6.09 | 7.06 |

In spite of the lower NH$_3$ removal capacity in wet conditions on MOF-5 than that on GO, the performance is still better than that on unmodified activated carbons, comparable to those on carbons modified with metal chlorides, and slightly better than that measured on carbons modified with polyoxometalates, or metal oxides. Since the capacity is high even though the pH is much higher than that for GO, other mechanisms than simple acid-base interactions must be involved in the retention of ammonia on those materials. It is interesting that on the exhausted samples (for MOF-5 and MOF-5-GO), the pH increases by only one pH unit after exposure to ammonia in spite of the high capacity. For this, a neutralization reaction or removal of a significant amount of ammonia dissolved in water by purging with dry air after the adsorption process is the possible explanation Analysis of the shapes of the NH$_3$ breakthrough curves and the desorption curves indicates the differences in the performance of materials. The relatively small area under the desorption curve in the case of GO in moist and dry conditions indicates a significant quantity of strongly adsorbed ammonia. For MOF-5, initially a sharp decrease in the concentration is noticed on the desorption curve and then, ammonia concentration in the air stream stays on a more or less constant level during the duration of the desorption experiment. A similar pattern is noticed for the nanocomposite. This must be related to the removal of water with dissolved ammonia. That process is expected to last a long time when very small sizes pores are present. All of this is a sign of a weak retention of ammonia. Moreover, as the parameters of porous structure indicate, after ammonia adsorption in moist conditions, the materials (MOF-5 and MOF-5-GO) become practically nonporous (see Table 4). This lost of porosity is due to a collapsing of the structure, as a result of water exposure, as already observed by Long and coworkers. As mentioned above, Greathouse and Allendorf showed that water leads to the destruction of the MOF-5 structure owing to its specific interactions with the zinc oxide clusters. Oxygen atoms in water progressively replace oxygen atoms in ZnO$_4$ tetrahedron. Hydrogen bonding between hydrogen atoms in water and oxygen atoms in ZnO$_4$ tetrahedron represents another way of interactions leading to the collapse of MOF-5 structure. That destruction might affect the kinetic of water desorption (with dissolved ammonia). It is also possible that that destruction happens gradually when ammonia is present in the system. Indeed, ammonia might compete with water for reactions sites owing to some similarities in the chemistries of these two species. In particular, hydrogen bonding between hydrogen atom in NH$_3$ and oxygen atoms in ZnO$_4$ tetrahedron appear as a plausible scenario. Support for this might be that observed increase in the ammonia concentration at the end of the desorption experiment. It is interesting that the structure does not collapse when it is exposed only to ammonia.

Another interesting feature on the breakthrough curves of the composite tested in moist conditions is a well-pronounced change in the shape of the curve with the progress of adsorption starting at a concentration of 50 ppm. This behavior is real and is not seen for GO or MOF-5. This suggests changes in the mechanism of adsorption or appearance of additional adsorption centers with the duration of the experiment. The changes in the chemistry can be only caused by either water or ammonia, or ammonia and water.

How ammonia changes chemistry of the composite is seen on the FTIR spectra. The spectra for GO before and after adsorption of ammonia were analyzed. The spectrum for the nanocomposite MOF-5-GO resembles that for MOF-5. The bands at 1510 cm$^{-1}$ and 1580 cm$^{-1}$ are attributed to the asymmetric stretching of carboxylic groups in BDC; whereas the one at 1390 cm$^{-1}$ is due to the symmetric stretching of carboxylic groups in BDC. In the region 1300-700 cm$^{-1}$, several bands are observed and they are assigned to the out-of-plane vibrations of BDC. After adsorption of ammonia in dry air, the spectra of both MOF-5 and MOF-5-GO do not change. However, in moist conditions, new bands at 660 cm$^{-1}$, 1230 cm$^{-1}$, 1300 cm$^{-1}$, 3200 and 3610 cm$^{-1}$ appear for MOF-5 and MOF-5-GO. The latter changes observed in the range 600-

1600 cm$^{-1}$ must be due to the collapsing of the MOF-5 structure and change in the environment of the carboxylic groups and the zinc oxide. Indeed, taking into account the proposed mechanism of destruction of the MOF-5 framework by water, carboxylic groups are "released" during this collapsing which must induce modifications in the vibrations at about 1600 cm$^{-1}$. A well-defined band at 3610 cm$^{-1}$ indicates the presence of strongly bound water. A broad band at ~3200 cm$^{-1}$ must be due to overlapping bands from O—H and N—H vibrations in water and ammonia, respectively. Comparison of the spectra obtained for MOF-5-EM and MOF-5-GO-EM with the corresponding ones obtained after exposure to a flow of humid air shows as a main difference a band at 1685 cm$^{-1}$ for samples run in humid air only. This band suggests the presence of protonated carboxylic groups in BDC. The fact that it is not observed for MOF-5-EM and MOF-5-GO-EM even though water is present suggests that ammonia interacts with those carboxylic groups. Indeed, carboxylic groups formed in this process might anchor ammonia ions via acid-base reaction. This finding explains the small increase in pH after exposure to ammonia mentioned above. Changes in the structure and chemistry of the materials after exposure to ammonia are also observed on X-ray diffraction patterns. The spectra for MOF-5-ED and MOF-5-GO-ED do not change significantly compared to the ones for the initial samples. Only an increased splitting in the peak at 2 Θ about ~9.60° is detected and it indicates a distortion in the cubic symmetry of MOF-5. MOF-5-EM spectrum is similar to the one for MOF-5 exposed to humid air only and indicates once again the collapsing of MOF-5 structure. For MOF-5-GO-EM, however, the spectrum is different than the one observed when the composite is exposed to moist air only. Two peaks at 2 Θ about 9.65° and 8.90° are detected. A possible explanation would be that the first peak (9.65°) belongs to the initial MOF-5 structure while the second one (8.90°) comes from the decomposed compound. This supports the hypothesis about the differences in the mechanism of destruction when ammonia together with water are present in the challenge gas and suggests different stability of the MOF-5 when combined with graphite oxide.

The instant results describe the synthesis and properties of MOF-5/GO nanocomposite. The material obtained has a unique layered texture with a preserved structure of MOF-5 and GO. When tested as an ammonia adsorbent, the composite shows synergy enhancing the adsorption capacity in comparison with the hypothetical physical mixture of components. Although the removal capacity is high in the presence of moisture, water has a detrimental effect on the chemistry of MOF-5 based materials and destroys the porous frameworks. Carboxylic groups from MOF-5 structure are released during the material's collapse and are then able to interact with ammonia. These processes (collapse of the structure and ammonia interaction with MOF-5 carboxylic groups) can also occur simultaneously owing to the competition between water and ammonia for the most reactive centers. This destruction of MOF-5 within the composite structure causes slow desorption of ammonia when the samples are purged with air due to the progressive removal of water in which it is dissolved.

Example 4

Reactive Adsorption of $NO_2$ on Copper-Based MOF and Graphite Oxide-MOF Composites Composites of a copper-based metal-organic framework (MOF) and graphite oxide (GO) were tested for $NO_2$ adsorption and retention of NO in dry and moist conditions. The samples were analyzed before and after exposure to $NO_2$ by thermal analysis, FTIR, X-ray diffraction and adsorption of nitrogen at −196° C. In dry conditions, the composites exhibit an enhanced $NO_2$ breakthrough capacity compared to MOF and GO separately. This improvement is linked to the increased porosity and the reactive adsorption of $NO_2$ on copper, which leads to the formation of bidentate and monodentate nitrate. Even though less $NO_2$ is adsorbed in moist conditions than in dry ones, the materials are more stable and the NO retention is enhanced. Water in the challenge gas competes with $NO_2$ to bind to copper and thus the number of reactive adsorption sites on which $NO_2$ can be adsorbed/react decreases.

Experimental

Materials

The syntheses of the parent materials, HKUST-1 and GO, are described in Example 8 and Seredych et al. (*J. Phys. Chem. C* 2007, 11, 15596-15604), respectively. The syntheses were done following Millward and coworkers for HKSUT-1 and Hummers for GO. The composites were synthesized in situ from the solution used to obtain MOF with the presence of dispersed GO. The preparation of the composites whose GO content ranges from 5 to 18 wt % of the final material weight is addressed in Example 8. The composites are referred to as MG-n with n=1, 2 and 3 for the different GO contents (5, 9 and 18 wt %, respectively).

Methods $NO_2$ Breakthrough Capacity

Evaluation of $NO_2$ sorption capacity was conducted in a laboratory-scale, fixed-bed reactor system, at room temperature and in dynamic conditions. In a typical test, a flow of $NO_2$ diluted with dry or moist (70% humidity) air went through a fixed bed of adsorbent with a total inlet flow rate of 225 mL/min and a $NO_2$ concentration of 1000 ppm. The adsorbent's bed was packed into a glass column (length 370 mm, internal diameter 9 mm) and consisted of about 2 cm$^3$ of glass beads well mixed with the amount of adsorbent required to obtain a homogeneous bed (between 50 and 120 mg). The beads were used to avoid the pressure drop and thus to favor the kinetics of the breakthrough tests. The concentrations of $NO_2$ and NO in the outlet gas were measured using an electrochemical sensor (RAE Systems, MultiRAE Plus PGM-50/5P). The adsorption capacity of each adsorbent was calculated in mg per g of adsorbent by integration of the area above the breakthrough curve. The tests were conducted until the concentrations of $NO_2$ and NO reached the electrochemical sensors' upper limit values of 20 ppm and 200 ppm, respectively. Tests were implemented by diluting the $NO_2$ stream with either dry or moist air stream, respectively. After the breakthrough tests, all samples were exposed to a flow of carrier air only (180 mL/min) to evaluate the strength of $NO_2$ retention. The suffixes-ED and -EM are added to the name of the samples after exposure to ammonia in dry and moist conditions, respectively.

Thermal Analysis

Thermogravimetric (TG) curves and their derivatives (DTG) were obtained using a TA Instrument thermal analyzer. The samples (initial and exhausted) were previously dried in oven at 100° C. to remove moisture and then submitted to a regular increase of temperature, from 30° C. to 1000° C., with a heating rate 10° C/min under a nitrogen flow held at 100 mL/min.

FTIR

Fourier transform infrared (FT-IR) spectroscopy was carried out using a Nicolet Magna-IR 830 spectrometer using the smart diffuse reflectance method. The experiments were done on the powdered samples 2-3 wt % (initial and exhausted), with 97-98 wt % KBr addition. The spectrum was generated, collected 16 times and corrected for the background noise with pure KBr spectra.

XRD

X-ray diffraction (XRD) measurements were conducted using standard powder diffraction procedures. Adsorbents (initial and exhausted) were ground with DMF (methanol for GO) in a small agate mortar. The mixture was smear-mounted onto a glass slide and then analyzed by Cu $K_\alpha$ radiation generated in a Philips X'Pert X-ray diffractometer. A diffraction experiment was run on standard glass slide for the background correction.

Adsorption of Nitrogen

Nitrogen isotherms were measured at −196° C. using an ASAP 2010 (Micromeritics). Prior to each measurement, initial and exhausted samples were outgassed at 120° C. The surface area, $S_{BET}$, the total pore volume, $V_t$, the micropore volume, $V_{mic}$ (Dubinin-Radushkevitch method), and the mesopore volume, $V_{mes}$, were obtained from the isotherms.

Results

Figure 3:
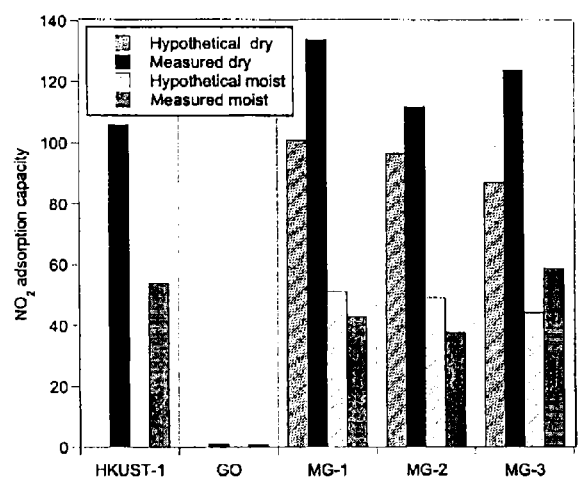
FIG. 3. Measured and hypothetical $NO_2$ adsorption capacity for the HKUST-1, GO, MG-1, MG-2 and MG-3 materials.

The $NO_2$ breakthrough curves of the materials were obtained. The calculated capacities (Q) in dry and moist conditions are summarized in Table 6. In dry conditions, the measured $NO_2$ adsorption capacities are more than twice higher than those in moist conditions. The amounts adsorbed range between 106 mg/g on HKUST-1 and 134 mg/g on MG-1 in dry conditions. In moist conditions values between 38 mg/g on MG-2 and 59 mg/g on MG-3 (Table 6) are reported. Moreover, different shapes of the breakthrough curves and different trends are observed depending on the conditions of the adsorption process. Generally, the addition of graphite oxide leads to an enhancement in the $NO_2$ capacity in dry conditions, since all the composite materials display a better performance than that of HKUST-1 (the following order is observed: MG-1>MG-3>MG-2>HKUST-1). In moist conditions, the amounts adsorbed changes following the trend: MG-3>HKUST-1>MG-1>MG-2. Based on the measured $NO_2$ adsorption capacities of the parent materials (HKUST-1 and GO) and the composition of adsorbents, the capacities for hypothetical physical mixtures for each composite sample were calculated. Comparison between the measured and hypothetical capacities is shown on FIG. 3. A very good performance of the composites in dry conditions indicates a beneficial synergy between the composite components. Such effect was found for $NH_3$ adsorption and it was attributed to the increased volume of small pores as a result of the interaction between GO and HKUST-1, which led to increased dispersive forces. On the other hand, in moist conditions, the experimentally measured amounts of $NO_2$ adsorbed are smaller than the hypothetical ones for all composites but MG-3. This suggests that water strongly modifies the adsorption mechanism of $NO_2$ on HKUST-1 and on the composite materials in comparison with the mechanism taking place in dry conditions. Taking into account the polar character of these two compounds, the competitive adsorption between water and $NO_2$ seems to be a plausible explanation. In dry conditions where all these metallic sites are available for binding to $NO_2$, the optimum capacity can be reached.

TABLE 6

$NO_2$ adsorption capacities (Q) and the percentage of NO released (R) for the HKUST-1, MG-1, MG-2, MG-3 and GO materials in dry and moist conditions.

| Sample | GO content [%] | Dry conditions | | Moist conditions | |
|---|---|---|---|---|---|
| | | $Q\,NO_2$ [mg/$g_{material}$] | $R\,(NO)^a$ [%] | $Q\,NO_2$ [mg/$g_{material}$] | $R\,(NO)^a$ [%] |
| HKUST-1 | 0 | 106 | 9 | 54 | 7 |
| MG-1 | 5 | 134 | 14 | 43 | 9 |
| MG-2 | 9 | 112 | 13 | 38 | 8 |
| MG-3 | 18 | 124 | >18[b] | 59 | 5 |
| GO | 100 | 1.2 | — | 0.8 | — |

[a]Amount of NO released during the adsorption process.
[b]Estimation based on a prospective of polynomial fitting from MG-3 NO curve.

Since a release of NO during $NO_2$ reactive adsorption can create an application problem, its concentration in the effluent was also monitored. The fraction of NO released (R) during $NO_2$ adsorption with respect to the amount of $NO_2$ adsorbed was calculated from the breakthrough curves and it is reported in Table 6. Since this fraction in dry conditions increases with an increase in the content of GO component (from 9% for HKUST-1 to around 18% for MG-3), this activity is linked to the capability of the carbonaceous component to reduce $NO_2$. In moist conditions for all materials less NO is released than in dry conditions. It is interesting that the amount of NO released decreases with an increase in the content of GO. This indicates that in moist conditions the reduction of $NO_2$ to NO is inhibited by the presence of graphene layers. Moisture also slightly improves the performance towards NO on HKUST-1 compared to the dry environment.

Considering the results, the presence of water in the challenge gas decreases the $NO_2$ adsorption capacity due to the competition between water and $NO_2$ to bind to copper. At the same time, it prevents NO formation/release from the surface. Since the reduction of $NO_2$ to NO by the carbonaceous component should not be visibly affected by the presence of water owing to the hydrophobicity of carbon materials, the formation of NO is likely caused by another mechanism/reaction than the reduction of $NO_2$ by the carbon matrix. This is supported by the fact that even in the absence of GO (see HKUST-1), NO is formed. A plausible explanation would be the adsorption of two $NO_2$ followed by a disproportionation reaction with formation of NO and nitrate. In the presence of water, the binding of $NO_2$ to the copper centers is limited so less NO is formed. Thus, besides the GO component, MOF also contributes to the release of NO as a $NO_2$ reactive adsorption by-product.

X-ray diffractograms of the fresh and exhausted samples were obtained. For all samples at all conditions, the structure of a parent material or composite can be considered as not significantly altered after the exposure to $NO_2$. Nevertheless, a general trend of a slight decrease in the intensity of the signals on the exhausted samples was observed, which indicates a partial destruction of the main framework. Among the materials studied, the MG-2 composite exhibits the most visible changes in structure after the $NO_2$ exposure in dry or moist conditions. This composite was also the least effective as a $NO_2$ adsorbent in both conditions. Surprisingly, the analysis of the $NO_2$ adsorption capacity in dry conditions and the analysis of the X-ray diffraction patterns after the exposure, indicate that the structure was more preserved on the materials that display high $NO_2$ adsorption capacities. This is in a contradiction with the study, where the $NH_3$ adsorption on the same materials was analyzed. (Example 7). In moist conditions, the observed behavior was more complex. As in dry conditions, MG-2, which is the least effective material for NO$_2$ adsorption seems to be the most damaged after the breakthrough test. For the other materials no clear indication of the changes in the structure after the exposure to NO$_2$ can be found. This relationship between the activity and stability of the structure clearly shows that the adsorption is accompanied by chemical reactions, which lead to a partial destruction of the composite framework. This destruction process results in a fast loss of NO$_2$ adsorption capacity, which is especially visible for MG-2 and HKUST-1 run in dry conditions.

Figure 4:
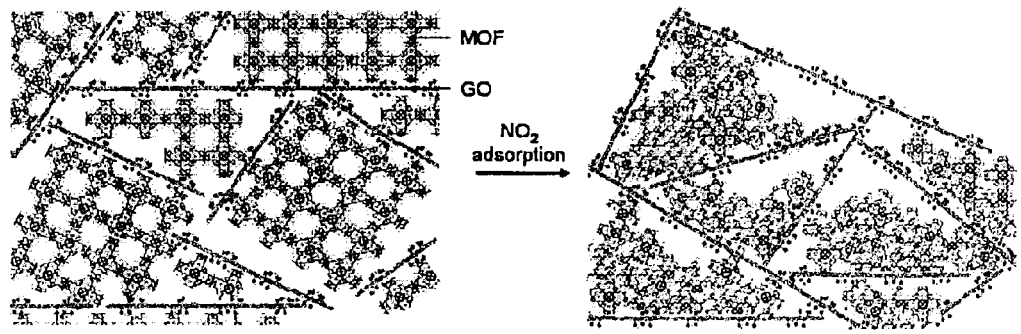
FIG. 4. Changes in the texture of the composite materials after exposure to $NO_2$.

The parameters of the porous structure calculated from the nitrogen adsorption isotherms are summarized in Table 7. As seen, a significant decrease in the surface area is found for the samples exposed to NO$_2$ in dry conditions. On HKUST-1 S$_{BET}$ decreases from 909 m$^2$/g to 63 m$^2$/g. This sample is the least effective adsorbent for NO$_2$. Concerning the composite materials, their specific surface area decreased 80% after the exposure to NO$_2$ in dry conditions. In moist conditions only 20% of the specific surface area has been lost after NO$_2$ adsorption on HKUST-1 and MG-2, while on MG-1 a 50% decrease was found. A similar trend is observed for the porosity. Surprisingly, a significant increase, even up to seven times in the volume of mesopores for the composite materials used in dry conditions was revealed. On HKUST-1, regardless the conditions of the breakthrough test, the volume of mesopores increases only slightly. The trend is similar to that one found for each composite in moist conditions. Those changes in the porosity of the composites in dry conditions suggest that the layers of GO somehow determine the structure of the materials and the mesoporosity is likely formed between the units of collapsed HKUST-1 attached the graphene layers. The changes in the texture are visualized in FIG. 4.

volume. However, due to the differences in the texture, the destruction of the micropores is manifested differently for HKUST-1 than for the composites. For the latter materials, the "densification/agglomeration" of the HKUST-1 component leads to the creation of mesopores, since the units of MOF are enclosed between GO layers (FIG. 4). Thus the addition of GO confers to the composite materials an apparent stability and the loss of micropores not necessarily leads to a dramatic decrease of the surface area as that found for HKUST-1.

To further analyze the mechanism of reactive adsorption, the hypothetical surface of the materials, S$_{th}$, was calculated using Equation (1) where D is the density of the material and assuming cubic particles of size d (listed in Table 7), which is the size of the particles evaluated from X-Ray diffraction data using the Scherrer equation (*Nach. Wiss. Gottingen, Math.-Phys. Kl.* 1918, 2, 98-100).

$$S_{th} = \frac{6 \cdot \sqrt{3}}{D \cdot d} \tag{1}$$

This value (S$_{th}$) represents the theoretical surface of the materials in the case where all the crystallites are separated from each others. The dependence of the NO$_2$ adsorption capacity on the ratio of these values to the specific surface areas (S$_{th}$/S$_{BET}$) was analyzed. That S$_{th}$/S$_{BET}$ ratio might be considered as an indication of the densification of the material particles. When this ratio is smaller and hypothetically reaching 1, the grains of materials are well separated from each other. Any increase of this value reflects a densification of the crystallites and the formation of particle boundary. The linear correlation (R$^2$=0.93) for the experiments run in moist conditions indicates that the adsorption of NO$_2$ is basically ruled

TABLE 7

The parameters of the porous structure for the HKUST-1, MG-1, MG-2 and MG-3 materials.

| Sample | S$_{BET}$ [m$^2$/g] | V$_t$ [cm$^3$/g] | V$_{mic}$ [cm$^3$/g] | V$_{meso}$ [cm$^3$/g] | V$_{mic}$/V$_t$ [%] | d$^c$ [nm] | S$_{th}$$^d$ [m$^2$/g] | S$_{th}$/S$_{BET}$ |
|---|---|---|---|---|---|---|---|---|
| HKUST-1 | 909 | 0.471 | 0.449 | 0.022 | 95 | 1000 | 6035 | 6.6 |
| HKUST-1-ED | 63 | 0.086 | 0.036 | 0.050 | 42 | — | — | — |
| HKUST-1-EM | 753 | 0.411 | 0.361 | 0.050 | 89 | — | — | — |
| MG-1 | 989 | 0.515 | 0.478 | 0.037 | 93 | 950 | 6819 | 6.9 |
| MG-1-ED | 273 | 0.333 | 0.099 | 0.234 | 30 | — | — | — |
| MG-1-EM | 418 | 0.271 | 0.194 | 0.077 | 72 | — | — | — |
| MG-2 | 1002 | 0.527 | 0.478 | 0.049 | 91 | 980 | 7562 | 7.5 |
| MG-2-ED | 159 | 0.251 | 0.062 | 0.189 | 25 | — | — | — |
| MG-2-EM | 811 | 0.434 | 0.392 | 0.042 | 90 | — | — | — |
| MG-3 | 996 | 0.566 | 0.522 | 0.044 | 92 | 1310 | 6216 | 6.1 |
| MG-3-ED | 146 | 0.208 | 0.064 | 0.144 | 31 | — | — | — |
| MG-3-EM | 738 | 0.356 | 0.307 | 0.049 | 86 | — | — | — |

$^c$Particles size calculated from X-ray line broadening and the Scherrer equation.
$^d$Specific surface area calculated assuming cubic particles of size d.

The decrease in the surface area in dry and moist conditions is in agreement with the partial damage of the structure after NO$_2$ exposure, observed on XRD diffractograms. It is hypothesized that binding between NO$_2$ and copper is responsible for the observed changes. Since this binding is limited in moist conditions, due to the competitive adsorption of water and NO$_2$ on copper, and thus "screening" of some copper centers from NO$_2$, the surface areas are less affected. Moreover, the results suggest that the organic network is also affected by the NO$_2$ adsorption on copper, since only broken bonds in the lattice can explain the loss of the microporous by the volume or the surface of grain boundary. Moreover, since NO$_2$ is known to be adsorbed in the micropores of carbonaceous materials, it is plausible to assume that micropores are formed between the particles and they enhance the physisorption of NO$_2$. As found based on the results of N$_2$ adsorption and XRD, this kind of adsorption is less destructive than the direct binding on copper (as observed in dry conditions). Water molecules act as a shield to prevent the destructive adsorption of NO$_2$ on Cu sites.

Thermal analyses were carried out on the initial and exhausted samples using DTG curves. Only the temperature range between 150° C. and 450° C. was included since at the temperatures lower than 150° C. only physically adsorbed species are removed and no visible changes are seen at the temperatures higher than 450° C. On the curves for the initial samples, a main peak, which is assigned to the decomposition of MOF, appears around 350° C. and a smaller signal, slightly before 300° C. (only on HKUST-1 and MG-1), is linked to the release of water from the structure. On the DTG curves for the exhausted samples the main peak at around 350° C. remains regardless the experimental conditions. However, a small shift to a lower temperature and a decrease in the intensity of this signal are observed for MG-2 and MG-3 in dry and moist conditions and only in moist conditions for HKUST-1. This shift might be the result of a partial destruction of the material framework during the adsorption process. The peak centered around 300° C. seen on DTG curves of the initial HKUST-1 and MG-1 samples is no longer visible for the exhausted materials. New peaks appear around 200° C. and 230° C. on each DTG curve for the samples run in dry and moist conditions. Based on the possible chemistry of the reactive adsorption process and the decomposition temperatures of the likely reaction products, these peaks are linked to the presence of nitrates ($Cu(NO_3)_2$) and/or hydroxide ($Cu(OH)_2$). For the samples exhausted in dry conditions, they should obviously represent the decomposition of copper-nitrate complex, since without water copper hydroxide would not be formed. In moist conditions, since it is considered that the competitive adsorption led to a preferable adsorption of water than $NO_2$ on the copper centers, copper hydroxide should be the complex rather formed.

FT-IR analysis brings additional details concerning complexes formed during the $NO_2$ reactive adsorption process. On the spectra for the materials exhausted in dry conditions, two new bands located at 1710 cm$^{-1}$ and around 1327 cm$^{-1}$ confirm the formation of nitrate bound to the copper. Moreover, the absence of this band on the spectra of the exhausted samples in moist conditions is further evidence that the presence of water prevents the interactions of $NO_2$ with the copper centers. The appearance of another new band at 1620 cm$^{-1}$ only on the exhausted samples after the dry runs indicates the bidentate nature of the nitrates formed.

Considering all the results addressed above, the following mechanism is proposed to describe the reactive adsorption of $NO_2$ in dry conditions on the HKUST-1 and its composites with GO.

As indicated above, the formation of a bidentate nitrate is supported by FT-IR analysis (band at 1710 cm$^{-1}$, 1620 cm$^{-1}$ and 1327 cm$^{-1}$). Such reaction requires the breaking of a Cu—O bond which consequently induces a loss of microporous volume (Table 7) and a partial collapse of the main structure (observed on XRD diffractograms) (Eq. 2). However, a second coordination may also occur since a small band at 1195 cm$^{-1}$ indicates that nitrate species can be bound with two different metallic centers. A second step in this mechanism may be considered since an increase in the intensity of the band at 1565 cm$^{-1}$ is linked to a change in the coordination of the carboxylate ligands from benzene tri-carboxylic. This step likely involves a second $NO_2$ molecule and leads to the formation of a monodentate nitrate bound to the copper (Eq. 3). This rearrangement may cause the appearance of carboxylic groups on benzene tri-carboxylic linkage and the formation of NO, which is observed to be released in each case during $NO_2$ adsorption process in dry conditions (Eq. 4).

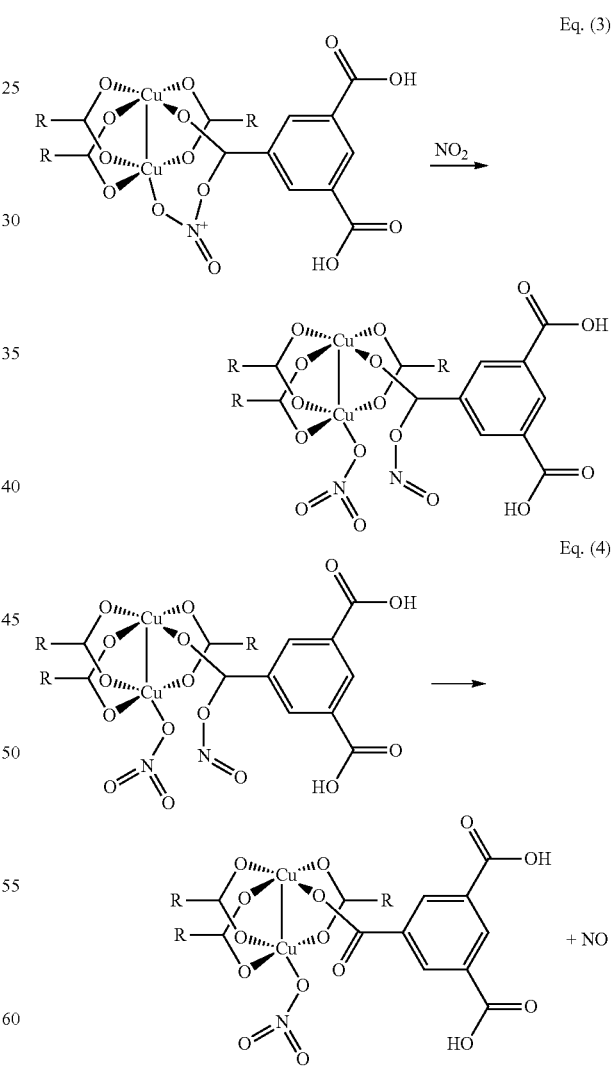

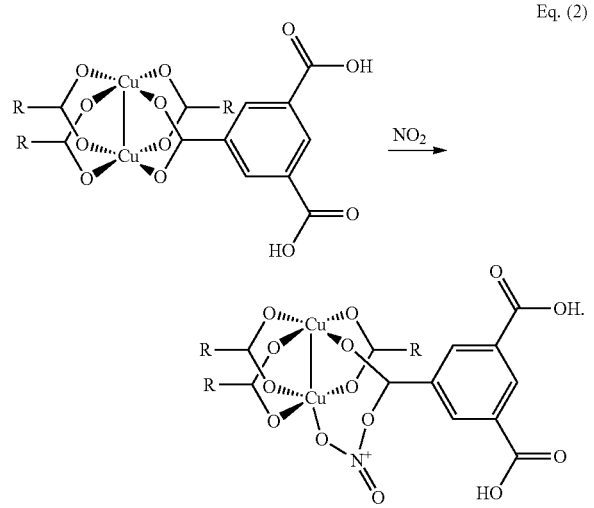

with R = benzene di-carboxylic

Concerning the FT-IR spectra of the exhausted samples after the exposure to $NO_2$ in moist conditions, no significant change was observed in comparison with the initial samples. This clearly indicates that the mechanism represented above mainly takes place in dry conditions. In moist conditions, the presence of water hinders the adsorption of $NO_2$ on the copper. Thus physical adsorption in small micropores is the main mechanism of the removal process.

The results show that the HKUST-1/GO composites exhibit significantly increased adsorption of $NO_2$ in dry conditions compared to the parent components. This is owing to an additional pore space formed between the HKUST-1 units and graphene units. The $NO_2$ adsorption mechanism on HKUST-1 and its composites with GO is very dependent on the presence of water. Taking into account the experimental results, two reaction pathways are proposed. In moist conditions, water is preferentially adsorbed on the copper centers and then reacts with them forming complexes. This reaction prevents the reactive adsorption of $NO_2$. By reducing the number of copper sites for $NO_2$ interactions, less NO is released. Lack of these interactions also results in a more stable structure. Nevertheless, since less copper sites are available for interactions with $NO_2$, the adsorption capacity of HKUST-1 and its composites is lowered in comparison with that in dry conditions. Experiments in moist conditions also indicate that $NO_2$ adsorption is enhanced when the particles are close to each other and thus small micropores are formed where that $NO_2$ can be adsorbed physically. In dry conditions the availability to the copper increases the density of active sites and thus more $NO_2$ is retained via reactive adsorption. Adsorption and disproportionation reaction of $NO_2$ accompanied by the release of NO result in a partial destruction of the porosity.

Example 5

Hydrogen Sulfide Adsorption on MOFs and MOF/GO Composites

Composites of a copper-based metal-organic framework (MOF) and graphite oxide (GO) were tested for hydrogen sulfide removal at ambient conditions. In order to understand the mechanisms of adsorption, the initial and exhausted samples were analyzed by various techniques including X-ray diffraction, Fourier Transform infrared spectroscopy, thermogravimetric analyses, and sorption of nitrogen. Compared to the parent materials, an enhancement in hydrogen sulfide adsorption was found. It was the result of physical adsorption of water and $H_2S$ in the pore space formed at the interface between the MOF units and the graphene layers where the dispersive forces are the strongest. Besides physisorption, reactive adsorption was found as the main mechanism of retention. $H_2S$ molecules bind to the copper centers of the MOF. They progressively react with the MOF units resulting in the formation of copper sulfide. This leads to the collapse of the MOF structure. Water is found to enhance adsorption in the composites as it allows the dissolution of hydrogen sulfide.

Experimental
Materials

The syntheses of the parent materials, referred to as HKUST-1 and GO, is described herein Example 8. The syntheses were done following Millward and coworkers for HKSUT-1 and Seredych and Bandosz for GO. The preparation of the composites whose GO content ranges from 5 to 46 wt % of the final material weight is addressed herein Example 8. They were prepared by in situ synthesis of MOF in the presence of dispersed GO. The composites are referred to as MG-n with n=1, 2 and 3 for the different GO contents (5, 9 and 18, 38 and 46 wt %, respectively).

Methods
$H_2S$ Breakthrough Dynamic Test

Fixed bed breakthrough tests were performed at room temperature and dynamic conditions to evaluate the hydrogen sulfide adsorption capacity of the materials. In a typical test, a flow of hydrogen sulfide diluted in moist air (1000 ppm, 250 mL/min) went through a fixed bed of an adsorbent sample. The adsorbent bed contained about 2 $cm^3$ of glass beads mixed with the adsorbent material (about 0.08 to 0.09 g) and prehumidified with moist air (200 mL/min) for two hours. The beads were used to facilitate the kinetics of adsorption and avoid pressure drop. Hydrogen sulfide concentration in the outlet stream was measured using a Multi-Gas Monitor MultiRAE Plus sensor. The possible formation of $SO_2$ during the adsorption was also monitored by MultiRAE Plus sensor. The experiment was carried out until the hydrogen sulfide concentration in the effluent gas reached 100 ppm (sensor limitation). The adsorption capacity of each sample was then calculated in mg per g of sorbent, as the area above the breakthrough curves. Desorption tests were conducted after the breakthrough by exposing the bed to a flow of moist air (200 mL/min). This was done to evaluate the strength of adsorption. The suffix -E is added to the name of the samples after exposure to hydrogen sulfide.

pH

The surface pH of the initial and exhausted samples was measured. About 0.02 g of the adsorbents powder was stirred overnight with 4 mL of deionized water and then the pH of the suspension was recorded.

XRD

X-ray diffraction (XRD) measurements were conducted as in Example 4.

FT-IR Spectroscopy

Fourier transform infrared (FT-IR) spectroscopy was carried out using a Nicolet Magna-IR 830 spectrometer using the attenuated total reflectance method (ATR). The spectrum was generated, collected 16 times and corrected for the background noise. The experiments were done on the powdered samples (initial and exhausted), without KBr addition.

Thermal Analysis

Thermogravimetric (TG) curves were obtained using a TA instrument thermal analyzer. The initial and exhausted samples were exposed to an increase in temperature of 10° C./min while the nitrogen flow rate was held constant at 100 mL/min. From the TG curves, differential TG (DTG) curves were derived.

Sorption of Nitrogen

Nitrogen isotherms were measured at −196 ° C. using an ASAP 2010 instrument (Micromeritics). Prior to each measurement, initial and exhausted samples were outgassed at 120° C. to vacuum 10 Torr. Approximately 0.05 g of sample was used for these analyses. The surface area, $S_{BET}$, (Brunauer-Emmet-Teller method), the micropore volume, $V_{mic}$, (Dubinin-Radushkevitch method), the mesopore volume, $V_{mes}$, the total pore volume, $V_t$, were calculated from the isotherms.

Results

The $H_2S$ breakthrough curves were obtained for all samples. The breakthrough time measured for GO was short and the breakthrough curve rather steep, indicating that the material is a poor adsorbent of $H_2S$. On the contrary, the breakthrough times of HKUST-1 and the composites were longer, especially that of MG-1 sample. This indicates the better retention of $H_2S$ on these materials compared to GO. The breakthrough capacities derived from the curves are summarized in Table 8. GO capacity is very low (9 mg/g) whereas HKUST-1 appears as a good adsorbent for $H_2S$ with a capacity of 92 mg/g. The performance of the MG-1, 2 and 3 samples exceeds that of HKUST-1. The order observed in terms of adsorption capacity for the composites is: MG-1>MG-2>MG-3>MG-4>MG-5. This trend differs from that observed for $NH_3$ adsorption on the same materials for which the capacity increased with the amount of GO up to 18 wt % and then decreased described in Example 4. Unlike in the case of $NO_2$ removal, the presence of moisture did not limit the retention of $H_2S$ on the MOF-based samples. For $NO_2$ adsorption, it was found that water bound the unsaturated copper centers of the MOF faster than $NO_2$ and thus led to a decreased capacity. In the case of the $H_2S$ adsorption, on the contrary, even though the samples were prehumidified before the breakthrough runs, $H_2S$ molecules are still able to replace $H_2O$ molecules to bind to the copper sites. To have some perspective on the performance of the samples, it is interesting to compare their capacities with the ones found in the literature for other types of adsorbents. For instance, the best performing samples reported so far are activated carbons with capacities up to 300 mg/g (T J Bandosz Colloid Interf. Sci. 246 (2002) 1-20). For zinc oxide, the values range between 1 and 25 mg/g whereas for sludge-based materials it is between 18 and 33 mg/g. Finally, clays can adsorb up to 50 mg/g hydrogen sulfide. Hamon and coworkers in their study of $H_2S$ adsorption on MOFs reported capacities from 170 mg/g to 340 mg/g depending on the material tested (Hamon et al., *J. Am. Chem. Soc.* 131 (2009) 8775-8777). However, unlike the values mentioned before, these ones were obtained at equilibrium under high pressure which usually leads to much higher capacities than those reported at dynamic conditions. It was observed that for all samples, almost no hydrogen sulfide was detected in the outlet stream upon air purging and the $H_2S$ concentration returns to 0 ppm after a few minute indicating strong retention. Moreover, for all tests the concentration of $SO_2$ in the outlet stream was oscillating between 0 and 0.1 ppm. The small amount of sulfur dioxide formed is the result of the oxidation of hydrogen sulfide by oxygen from the air. The possible catalytic action of the surface cannot be ruled out.

TABLE 8

Measured and hypothetical $H_2S$ breakthrough capacities, amount of water adsorbed during prehumidification and surface pH values.

| Sample | $H_2S$ breakthrough capacity [mg/g of sorbent] | Hypothetical $H_2S$ breakthrough capacity [mg/g of sorbent] | Water adsorbed [mg/g of sorbent] | pH Initial | pH Exhausted |
|---|---|---|---|---|---|
| GO-E | 9 | — | 84 | 2.47 | — |
| HKUST-1-E | 92 | — | 178 | 4.19 | 2.86 |
| MG-1-E | 199 | 88 | 438 | 4.22 | 2.80 |
| MG-2-E | 121 | 84 | 346 | 4.34 | 3.06 |
| MG-3-E | 109 | 77 | 328 | 4.45 | 3.06 |
| MG-4-E | 98 | 61 | 268 | 4.23 | 3.38 |
| MG-5-E | 80 | 54 | 252 | 4.32 | 3.84 |

To evaluate if a synergy occurs between GO and HKUST-1 for $H_2S$ adsorption on the composites, the measured capacities must be compared to the ones determined for the physical mixture of GO and HKUST-1. The capacity of the physical mixture or "hypothetical" capacity is calculated as described below in Equation (5):

$$A_{composite} = A_{GO} \times wt\%_{GO} + A_{HKUST-1} \times wt\%_{HKUST-1} \quad (5)$$

In the above equation, "$A_i$" refers to the adsorption capacity (in mg/g) of the compound "i". The obtained values are listed in Table 8. As one can see, the measured capacities exceed the hypothetical ones indicating a synergetic effect between HKUST-1 and GO. This effect was also observed for ammonia and nitrogen dioxide removals on the same composites. The characterization of the various samples is described in Example 8. More precisely, an increase in the porosity of the composites compared to that calculated for the physical mixture of HKUST-1 and GO was found. This enhancing trend was observed up to a GO content of 18 wt % and then, with higher contents of GO, the beneficial effect on porosity vanished. Considering this, it is believed that the increase in adsorption capacity compared to that of the physical mixture is related to the increased pore space present in the composites. Since this pore space is mainly in very small pores, the dispersive forces governing physical adsorption also increase. However, unlike $NH_3$ and $NO_2$ removal, the trend of the enhancement in the adsorption capacity does not follow the trend of the increased in porosity. This is an indication that not only physisorption but also reactive adsorption governs $H_2S$ removal process. Signs of this reactive adsorption were observed through the bed color changes that occurred during the breakthrough runs. The bed initially light blue in color (due to water binding to the copper) progressively turned black suggesting the formation of copper sulfide. Evidence for this is presented below.

To investigate in more details the reactive adsorption of $H_2S$ as well as its effects on the structure of the materials, the samples were analyzed before and after exposure to $H_2S$ by various techniques and the results are presented below. Data for GO are not presented since no significant changes were observed after adsorption due to the low performance of that sample. Moreover, the features of GO are not distinguished on the surface of the composites.

As seen in Table 8, the pH values of the samples measured after adsorption are low suggesting that compounds of higher acidity than $H_2S$ are formed. BTC acid which is discussed later, can contribute to this as one of the products of surface reactions/MOF destruction during $H_2S$ reactive adsorption. Other species that could induce this decrease in pH might be sulfurous acid or bisulfate ions formed when $SO_2$ is in contact with water. Even though $H_2S$ dissociation was probably limited on the materials owing to surface pH close or lower than the indicated treshold of 4.5 found for porous adsorbents, its dissolution in the water film formed inside the pores on the materials likely occurred and thus contributed to the adsorption of that gas. This is supported by the fact that a good correlation (linear trend, correlation factor of 0.96) exists between the amount of water preadsorbed and the adsorption capacity of the composites. However, this trend is not valid when the HKUST-1 sample is considered with the others. This suggests that the mechanism of adsorption on the latter material is different than that on the composites. As one can see, the amount of water preadsorbed on the composites decreased as the GO content increases. This can be related to the decrease in porosity, to the decrease in the surface hydrophilicity owing to the presence of carbonaceous component and also to the decrease in the number of copper sites available for binding. Surprisingly, on HKUST-1, the amount of preadsorbed water is even smaller than on the composites even though no GO is present. An explanation for this should be related to the structure of HKUST-1 as compared to that of the composites. The graphene layers "segment" the MOF component. This can lead to an increase in the number of edge sites on the MOF where water can be adsorbed.

X-ray diffraction patters of the various samples before and after $H_2S$ adsorption were obtained. The fresh materials exhibit similar to each other patterns indicative of a crystalline structure attributed to HKUST-1. After H₂S adsorption, this crystalline character is lost. From these data, it becomes clear that exposure to hydrogen sulfide causes the collapse of the MOF structure as observed with NH₃ removal and in a lesser extent with NO₂ adsorption. Since water and hydrogen sulfide were the two species present in the system and since HKUST-1 is known to be water stable, it is likely that the decomposition is due to reactions of H₂S with the MOF units.

Insight on the products resulting from this reactive adsorption was provided by FT-IR, i.e., the spectra for all the samples were obtained for the fresh and exhausted samples. For the initial HKUST-1 and the fresh composites, several bands in the range 1350-1750 cm⁻¹ were observed which correspond to the symmetric (1645 and 1590 cm⁻¹) and asymmetric (1450 and 1370 cm⁻¹) stretching vibrations of the carboxylate groups in BTC. In the lower wavenumber range (1300-700 cm⁻¹), out-of-plane vibrations were observed. After H₂S adsorption, significant changes in the vibration bands were observed. By comparison with the spectrum for BTC, the spectra of the exhausted samples was "in-between" those of the initial samples and BTC. All the new bands that appeared at 2850, 2550, 1710, 1610, 1405, 1275, 890 cm⁻¹ were observed on the spectrum of BTC and the vibrations became less pronounced as the GO content increased. All of this suggests that the adsorption of H₂S leads to a "release" of the BTC ligands (no more coordinated to copper), which may also contribute to the decrease in the pH after H₂S adsorption mentioned above. Moreover, the appearance of the band at ~1710 cm⁻¹ suggests the formation of the acidic form of BTC. The bands at 2550 cm⁻¹ observed on the spectra of the exhausted samples and present on the spectrum of BTC can also be attributed to S—H stretching vibrations in H₂S species.

DTG curves of the initial and exhausted samples were plotted. The curves of the fresh samples exhibit three major peaks corresponding to the removal of the solvent (100° C.), the release of the water of crystallization (300° C.) and the decomposition of the BTC (350° C.). After exposure to hydrogen sulfide, a major change was observed in the shape of the peak at 350° C. This is partly due to the fact that, as described above, the MOF units are decomposed during the adsorption process leading to the "release" of BTC. Since BTC (not coordinated to copper) does not have the same temperature of decomposition as BTC in HKUST-1, a shift in the peak can occur. The broad character of the peak after the exposure to H₂S can be linked to the different forms of BTC. For instance, in addition to BTC "alone," some "remains" of the original HKUST-1 structure can be present. They likely decompose at a slightly different temperature. Another broad peak between 150 and 250° C. was assigned to copper sulfide. It has to be noted that SO₂ strongly adsorbed can also appear in this range. This would explain the appearance of the black color observed during the breakthrough tests. It is also interesting to notice that even though experiments were conducted in the presence of moisture and after a prehumification, the amount of water released at ~80° C. during thermal analysis remains low. This confirms the previous hypothesis that H₂S molecules are better ligands that H₂O molecules for copper and progressively replace them during the breakthrough runs.

All the changes in the materials caused by H₂S adsorption have an impact on the porosity. The parameters of porous structure derived from the nitrogen isotherms at −196° C. of the exhausted samples are given in Table 9 and compared to those for the initial samples. As one can see, the porosity of the samples, although not completely lost, significantly decreases after exposure to H₂S. This could be due to a pore blocking effect caused by adsorbed H₂S and its reactive adsorption products. However, the decomposition of the MOF structure evidenced above is a more likely explanation. The latter phenomenon was also observed in the case of NH₃ and NO₂ removal on these materials. Excluding MG-3 sample, the trend in the decrease of surface area and volume of pores follows the one for the adsorption capacities. This represents another proof that H₂S reacted with HKUST-1. Indeed, the more H₂S reacts with the HKUST-1 units, the more the MOF structure is destroyed.

TABLE 9

Parameters of porous structure derived from the nitrogen isotherms at −196° C. for the samples studied before and after exposure to hydrogen sulfide.

| Sample | $S_{BET}$ [m²/g] | $V_{tot}$ [cm³/g] | $V_{meso}$ [cm³/g] | $V_{mic}$ [cm³/g] | $V_{mic}/V_{tot}$ |
|---|---|---|---|---|---|
| HKUST-1 | 859 | 0.454 | 0.039 | 0.415 | 0.91 |
| HKUST-1-E | 301 | 0.397 | 0.246 | 0.151 | 0.38 |
| MG-1 | 989 | 0.515 | 0.037 | 0.478 | 0.93 |
| MG-1-E | 141 | 0.116 | 0.042 | 0.074 | 0.64 |
| MG-2 | 1002 | 0.527 | 0.049 | 0.478 | 0.91 |
| MG-2-E | 406 | 0.264 | 0.069 | 0.195 | 0.72 |
| MG-3 | 996 | 0.566 | 0.044 | 0.522 | 0.92 |
| MG-3-E | 77 | 0.087 | 0.048 | 0.039 | 0.45 |
| MG-4 | 704 | 0.370 | 0.052 | 0.348 | 0.94 |
| MG-4-E | 157 | 0.117 | 0.045 | 0.072 | 0.62 |
| MG-5 | 620 | 0.345 | 0.051 | 0.294 | 0.85 |
| MG-5-E | 155 | 0.155 | 0.079 | 0.071 | 0.46 |

Considering the conclusions drawn from the above, proposed mechanisms leading to the products of adsorption observed as well as the decreased porosity is presented in Reaction (6):

(6)

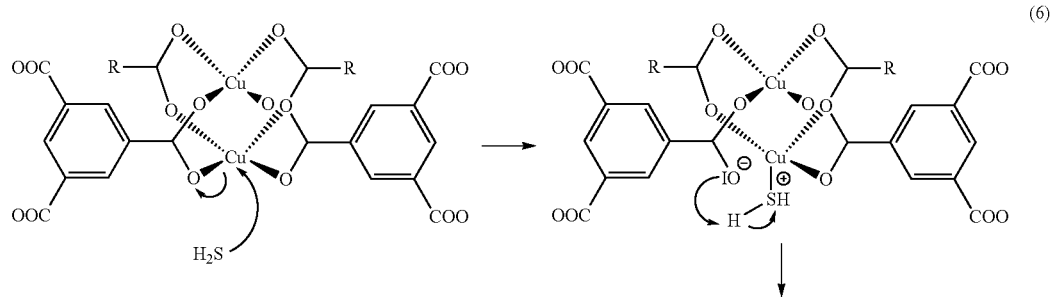

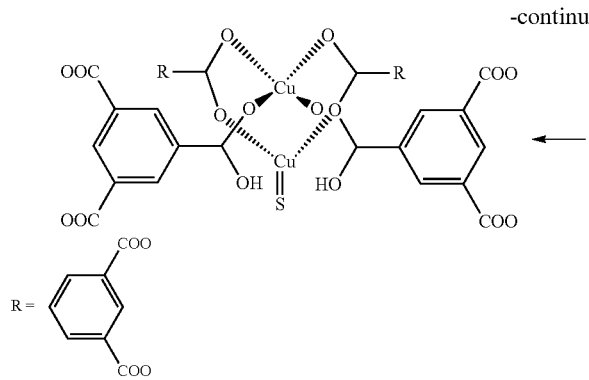
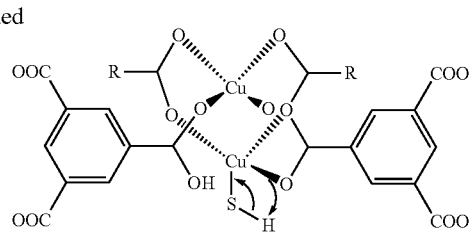

In a first step, hydrogen sulfide binds to the copper sites (likely replacing a molecule of water). This step is then followed by successive reactions that lead to the formation of carboxylic acid (FT-IR spectra and DTG curves) and copper sulfide (DTG curves) as well as a change in the coordination between copper and the oxygen of BTC (FT-IR spectra). The latter phenomenon induces a breaking of bonds that results in the decomposition of the HKUST-1 structure (XRD patterns, FT-IR spectra, DTG curves) and a decrease in the porosity (nitrogen adsorption). From these reactions, one can see that as the number of available copper sites increases, the potential for $H_2S$ to be adsorbed and form copper sulfide increases as well. This likely explains the trends in the adsorption capacity and porosity observed above. Considering this, one could argue that in HKUST-1, the concentration of copper sites is higher and consequently, its adsorption capacity should be higher as well. Nevertheless, one has to consider that in the composites, an additional pore space is present and the dispersive forces are stronger. Consequently, physisorption in the composites also takes place. Moreover, preadsorbed water likely favors the adsorption as well by enhancing the dissolution of $H_2S$ as described above. This can also explain the greater adsorption capacity of MG-1 sample compared to HKUST-1 or the other composites. A proper combination of the features enhancing physisorption and the ones enhancing the reactive adsorption seems to govern the removal process of hydrogen sulfide on the studied materials. Thus the highest adsorption of MG-1 can be explained by the fact that small amount of GO does not limit significantly the sizes of HKUST-1-units with active copper centers and at the same time creates some volume of small pores where water can be strongly retained. Addition of more GO, even though it results in an increase in the volume of micropores, causes less water adsorption owing to more hydrophobic character of GO than MOF (Table 8). As a consequence the amount of $H_2S$ adsorbed decreases. Since $H_2S$ reacts with the HKUST-1 units of the composites and induces a permanent decrease/change of the porosity, the adsorption process of $H_2S$ on HKUST-1 and the composites is irreversible. This has the advantage to prevent any release of the gas overtime. However, it may raise issues of regeneration of the adsorbents.

The results show high irreversible reactive adsorption of $H_2S$ on MOF/GO composites. During the exposure to the challenge gas, $H_2S$ molecules bind to the copper centers of the MOF and progressively react with the carboxylate ligands of the MOFs. This causes the formation of copper sulfide (observed via the color change of the adsorbent bed during the tests: form blue to black) and the permanent loss of porosity of the materials. It was also found that water, which is present in the system owing to bed prehumidification, does not prevent the adsorption of hydrogen sulfide. On the contrary, it favors its retention via dissolution in the water film inside the pores of the composites. Hydrogen sulfide, besides reactive adsorption is also physically adsorbed in the MOF and composites' pores. In the case of latter materials that pore space is located between the MOF units and the graphene layers where the dispersive forces are the strongest. The presence of that new pore space enhances the amount of hydrogen sulfide retained in the composites compared to the parent materials.

Example 6

HKUST-1/GO and MOF-5/GO $NH_3$ Adsorption in Wet Conditions

MOF-5 and HKUST-1 composites materials are characterized by X-ray diffraction, sorption of nitrogen, thermal analyses, Fourier Transform infrared spectroscopy (FT-IR) and scanning electron microscopy (SEM). The water stability and ammonia adsorption capacity of the hybrid materials were also evaluated. In most cases, composites materials' porosity increased compared to the one calculated considering the physical mixture of MOF and GO. This new porosity likely located between the two components of the hybrid materials is responsible for the enhanced ammonia adsorption capacity of the compounds. However, for both the zinc-based and the copper-based materials (MOFs and hybrid materials), a collapse of the framework was observed as a result of ammonia adsorption. This collapse is caused by the interactions of ammonia with the metallic centers of MOFs either by hydrogen bonding (zinc-based materials) or coordination and subsequent complexation (copper-based materials). Whereas the MOF-5 based compounds collapse in presence of humidity, the copper-based materials are stable.

Experimental

Initial Materials

Graphite oxide was synthesized as described in Example 2.
MOF-5 was prepared as described in Example 1.
HKUST-1 was prepared by mixing copper nitrate hemipentahydrate (10 g) and 1,3,5 benzenetricarboxylic acid (5 g) in DMF (85 mL) followed by stirring and sonication for 5 minutes. Ethanol (85 mL) was then added to the mixture, which was then stirred and sonicated for 5 minutes. Finally, deionized water (85 mL) was added to the mixture and then stirring and sonication for 30 minutes were carried out. All crystals were dissolved at this point. The mixture was then transferred to a round bottom flask (500 mL) and heated at 85° C. in an oil bath. The mixture was kept in the oil bath for 21 hours under shaking (intensely for the first four hours, and then the shaking was reduced and then stopped after 20 hours). After cooling, the crystals were filtered using a Buchner funnel, washed and immersed in dichloromethane. Dichloromethane was changed twice during three days. The crystals were collected after filtration and washing with dichloromethane. Drying was then performed in vacuum using the same process as described for MOF-5. The resulting product was kept in a dessicator and is referred to as HKUST-1.

Hybrid materials

The hybrid materials based on MOF-5 were prepared by dispersing GO powder in the well-dissolved zinc nitrate/BDC mixture. The resulting suspensions were subsequently stirred and subjected to the same synthesis procedure as for MOF-5. The added GO consists of 5 or 20 wt % of the final material weight. The synthesized compounds are referred to as ZnMG-n with n=1 and 2 depending on the GO content (5 and 20 wt %, respectively).

Similarly, to prepare the hybrid materials based on HKUST-1, GO powder was added to the well-dissolved precursors and solvents mixture used to synthesize HKUST-1. The resulting mixture was sonicated for 5 minutes, stirred for another 30 minutes and then the same synthesis procedure as that for HKUST-1 was carried out. The added GO consisted of 5 and 18 wt % of the final material weight. The compounds are referred to as CuMG-n with n=1 and 2 depending on the GO content (5 and 18 wt %, respectively).

Methods

XRD

X-ray diffraction (XRD) measurements were conducted as described in Example 1.

Sorption of Nitrogen

Nitrogen isotherms of the samples were measured at 77 K using an ASAP 2010 (Micromeritics). Prior to each measurement, samples were outgassed at 120° C. Approximately 0.10 g of sample was used for these analyses. The surface area, $S_{BET}$, (BET method), the micropore volume, $V_{mic}$, (Dubinin-Radushkevitch method (Dubinin 1966)), the mesopore volume, $V_{mes}$, the total pore volume, $V_t$, were calculated from the isotherms.

Thermal Analysis

Thermogravimetric (TG) curves and their derivatives (DTG) were obtained using a TA Instrument thermal analyzer. The samples were heated up to 1000° C. with the heating rate 10 deg/min under a flow of nitrogen of 100 mL/min.

FT-IR Spectroscopy

Fourier transform infrared (FTIR) spectroscopy was carried out as described in Example 1.

SEM

Scanning electron microscopy was performed on a Zeiss Supra 55 instrument. The instrument has a resolution of 5 nm at 30 kV. Scanning was performed on a sample powder previously dried and sputter coated with a thin layer of gold to avoid charging.

TEM

Transmission electron microscopy (TEM) was performed as described in Example 3.

$NH_3$ Breakthrough Dynamic Test

In order to determine the ammonia breakthrough capacity, dynamic breakthrough tests were performed at room temperature. In a typical test, a flow of ammonia diluted with air went through a fixed bed of adsorbent with a total inlet flow rate of 450 mL/min (225 mL/min for HKUST-1 and CuMG-n samples) and an ammonia concentration of 1000 ppm. For MOF-5 and the ZnMG-n samples, the adsorbent's bed contained about 2 cm³ of adsorbent. In the case of HKUST-1 and the CuMG-n samples, a 2 cm³ bed was prepared by mixing glass beads with the amount of adsorbent required to obtain a homogeneous bed (between 50 and 120 mg). This was done to avoid the pressure drop and thus to favor the kinetics of the breakthrough tests. In both cases, the mixture was packed into a glass column. The concentration of ammonia in the outlet gas was measured using an electrochemical sensor (Multi-Gas Monitor ITX system). The adsorption capacity of each adsorbent was calculated in mg per g of sorbent by integration of the area above the breakthrough curve. Tests were performed in wet conditions by diluting the ammonia stream with moist air stream, respectively. This was done to analyze the effects of water on the adsorption capacity. After the breakthrough tests, all samples were exposed to a flow of carrier air only (180 mL/min) to impose the desorption of ammonia and thus to evaluate the strength of its retention. The suffix -E is added to the name of the samples after exposure to ammonia.

Results

X-ray diffraction patterns of the parent and the hybrid materials provide information on their structure. The various peaks below 2 Θ~7.5° and seen for all samples originate from the glass slide used to run the analyses. They should not be considered in the analysis of the patterns. The two MOFs samples exhibit the expected pattern for MOF-5 and HKUST-1, respectively (Biemmi 2009; Kaye 2007). A single peak at about 2 Θ9.3° is seen in the case of GO and is related to an interlayer distance of 9.5 Å. The patterns of the hybrid materials are rather similar to the ones of the parent MOFs for both the ZnMG-n and CuMG-n series of samples. This suggests that the presence of GO did not prevent the formation of the crystalline frameworks. Moreover, it is interesting to notice that no peak corresponding to GO is present on the diffraction patterns of the hybrid materials. This is likely due to the fact that in the preparation of these materials, DMF was used. This polar solvent is known to cause the dispersion/exfoliation of GO which results in the absence of peak on the XRD patterns (Park 2009). Even though the structure of each MOF is preserved in both types of hybrid materials, one can see that a splitting of the peak at about 9.7° is observed for the ZnMG-n samples and becomes more pronounced as the GO content increases. This splitting has already been described in the literature and is assigned to a distortion of the cubic symmetry in MOF-5 (Hafizovic 2007) which, in the instant case, is likely caused by the presence of GO. The frameworks of HKUST-1 does not seem affected by GO.

Porosity is a paramount feature of adsorbents. The parameters of the porous structure are listed in Table 1 and the nitrogen isotherms were plotted for all materials. In Table 10, both the structural parameters measured and the hypothetical ones calculated assuming the physical mixture of MOF and GO are listed. Both the MOFs and the hybrid materials of each series of samples exhibit type I isotherms typical of microporous materials. The MOF-5 and HKUST-1 networks are made of 8 and 9A square channels, respectively (Chui 1999; Li 1999). From a general point of view, the ZnMG-n series of samples is less porous than the CuMG-n one. This must be related to the lower porosity of MOF-5 compared to HKUST-1. It is interesting that CuMG-1 and CuMG-2 have a higher surface area and volume of pores than HKUST-1. Moreover, for the CuMG-n samples, the measured porosity is always higher than the hypothetical one. This enhanced porosity is likely due to the creation of new pores at the interface between the MOF component and the GO component. On the contrary, the porosity of the ZnMG-n samples is smaller than that of MOF-5 and than that one calculated for the physical mixture of MOF and GO. That smaller volume of pores does not contradict the existence of enhanced dispersive forces.

TABLE 10

Parameters of porous structure derived form nitrogen isotherms and the hypothetical values (H) calculated assuming the physical mixture between the hybrid materials components.

| Sample | $S_{BET}$ [m²·g⁻¹] | $V_{tot}$ [cm³·g⁻¹] | $V_{meso}$ [cm³·g⁻¹] | $V_{mic}$ [cm³·g⁻¹] | $V_{mic}/V_{tot}$ | $S_{BET}$H [m²·g⁻¹] | $V_{tot}$H [cm³·g⁻¹] | $V_{mic}$H [cm³·g⁻¹] |
|---|---|---|---|---|---|---|---|---|
| GO | 5 | na | na | na | — | — | — | — |
| MOF-5 | 793 | 0.41 | 0.02 | 0.39 | 0.94 | — | — | — |
| ZnMG-1 | 706 | 0.37 | 0.03 | 0.34 | 0.93 | 753 | 0.39 | 0.37 |
| ZnMG-2 | 603 | 0.33 | 0.04 | 0.29 | 0.89 | 634 | 0.33 | 0.31 |
| HKUST-1 | 909 | 0.47 | 0.02 | 0.45 | 0.95 | — | — | — |
| CuMG-1 | 989 | 0.52 | 0.04 | 0.48 | 0.93 | 864 | 0.45 | 0.43 |
| CuMG-2 | 996 | 0.57 | 0.05 | 0.52 | 0.92 | 746 | 0.39 | 0.37 |

Thermal analyses results provide some indications on the formation of the new hybrid materials. The DTG curve for GO reveals a major peak at ~200° C. related to the decomposition of epoxy groups (Lerf 1998). The smaller peak below this temperature is due to the removal of physically adsorbed water whereas the one above 250° C. represents the decomposition of carboxylic and sulfonic groups (Szymanski 2002). Similar as in the cases of X-ray diffraction and nitrogen adsorption analyses, the features of the hybrid materials resemble the ones of the parent MOFs for both the ZnMG-n and the CuMG-n series of samples. In the case of MOF-5 and ZnMG-n samples, the small peak at ~200° C. is attributed to the removal of solvent (Huang 2003). For the HKUST-1 and CuMG-n samples, water is released at ~100° C. Decomposition of the organic ligand (BDC or BDC) with release of $CO_2$ and collapse of the MOF structure is observed at ~540° C. for the MOF-5 and ZnMG-n samples and 350° C. for the HKSUT-1 and CuMG-n samples. This indicates the greater thermal stability of the zinc-based materials than that of copper-based ones. The peak at ~300° C. for the latter materials is assigned to the release of water of crystallization (Seo 2009). The decrease of that peak in the hybrid materials when GO is present can be due to a decrease in surface hydrophilicity. An explanation for that could be in the involvement of the oxygen groups in GO in linkages with the MOF component. Indeed, if these linkages are formed, then MOFs units are surrounded by carbon layers (from GO) creating a hydrophobic environment around the MOF units and thus resulting in a decrease of hydrophilicity. In fact, an interesting feature of the hybrid materials is the absence of the intense peak of GO related to epoxy groups. This suggests that these functionalities are involved in the building process of the new materials. To verify that the absence of this peak was not due to the reaction of the epoxy groups with compounds other than HKUST-1 during the synthesis of the hybrid materials, GO alone was subjected to the same synthesis process as for the hybrid materials and run thermal analyses on the resulting sample. The above hypothesis was supported by the presence of the peak at 200° C. on the DTG curves for these materials. In fact, the formation of MOF occurs via the coordination of carboxylates groups (and thus oxygen groups) and metallic centers. Among the functionalities of GO capable of binding the metals sites, one can mention epoxy, carboxylic, hydroxylic and sulfonic groups.

SEM pictures show small differences in the texture of the hybrid materials compared to that of the parent materials. In the case of GO, a dense packing of carbon layers is observed; whereas both MOF-5 and HKUST-1 exhibit crystalline structures with some defects (and remains of an amorphous phase for MOF-5). The ZnMG-1 sample appears as a layered compound. These layers likely correspond to an alternation between layers of GO and MOF-5 blocks. The overall texture of the CuMG-n samples differs from the other type of hybrid materials.

TEM images of GO show well-defined carbon layers. For ZnMG-2 sample, carbon layers with embedded MOF-5 units were observed. TEM images show that the MOF and GO component are well-mixed within the hybrid materials. This supports the results of thermal analyses and the hypothesis that chemical interactions are involved in the formation of the composites. Similar observations can be made for the copper-based samples.

Considering the differences between the two series of hybrid materials and taking into account the data from thermal analyses, it is believed that the formation of the materials is governed by availability of the oxygen groups of GO and the way they are coordinated to the metallic sites. In the case of MOF-5, all the oxygen atoms forming the zinc oxide tetrahedra are equivalent in terms of "spatial arrangement." Consequently, any change of structure between the ZnMG-n samples must be related to the oxygen groups of GO. GO contains oxygen groups on the basal planes (epoxy, hydroxyl, ketone . . . ) and on the edges of the layers (carboxylic and sulfonic groups). Depending on the type of groups interacting with MOF-5 metallic sites, the structure of the hybrid materials can change. For instance with a high GO content, more carboxylic groups are present and their interaction with zinc must be preferred compared to the epoxy groups. This is because, besides the numbers of groups, one can also consider the probability for the MOF units/precursors to "encounter" the GO functional groups in the synthesis medium. As the content of GO increases, this probability increases for both carboxylic and epoxy groups. Given the preferred affinity of copper for carboxylic groups (compared to epoxy), it is believed that, at some point (for a specific GO content), the binding copper/carboxylic groups can be dominant. This overall mechanism of hybrid materials formation is also applicable to the CuMG-n samples. However, in this case an additional "degree of modification" must be taken into account since the coordination to the copper sites are not all equivalent. Indeed, attachment of the oxygen groups of GO to copper can occur either in the axial position (replacement of water molecule) or in the equatorial position (replacement of BTC) (see FIG. 5). Because of this, there is a more disordered structure in the case of CuMG-n samples compared to the ZnMG-n materials. One has to remember that this ordered/disordered character refers to the molecular structure of the materials and is not necessarily apparent on the SEM pictures.

Considering all the above, proposed structures for the ZnMG-n and CuMG-n samples are proposed in FIG. 6. The more regular arrangement of the MOF-5-based compounds and their layered structure is visualized. On the contrary, the copper-based hybrid materials exhibit a more disordered structure. These two representations are therefore in agreement with the SEM images and the interactions between MOF metallic centers and the oxygen groups of GO. Moreover, in both series of samples, a new pore space is created between the MOF blocks and the GO units.

The hybrid materials were tested for the ammonia removal in moist conditions. The breakthrough and desorption curves were obtained for all samples. As was seen from the shape of the breakthrough curves, the kinetics of interactions between ammonia and the hybrid materials are faster for the HKUST-1 based materials than for the zinc-containing compounds. Moreover, for both types of hybrid materials and MOFs, the retention of ammonia is rather weak as was seen from the shape of the desorption curves. The weakly adsorbed ammonia released during air pugging must be the one dissolved in the water film formed in the adsorbents pore space (Petit 2009). An interesting plateau is noticed on the breakthrough curves on the ZnMG-n samples. The concentration at which this plateau appears decreases with the increase in the GO content. This feature has already been observed for another MOF tested for ammonia removal but no explanation was proposed (Britt 2008). It can be related to the appearance of new centers able to interact with ammonia. The adsorption capacities determined from the breakthrough curves are listed in Table 11 for all the samples together with the hypothetical adsorption capacities. The latter correspond to the adsorption capacities of the physical mixture of MOF and GO. It is worth noticing that in the case of ZnMG-n samples, the component showing the best ammonia adsorption capacity is GO whereas it is the MOF material in the case of HKUST-1 (Table 11). The difference in the breakthrough capacities between MOF-5 and HKUST-1 and consequently, the ones of the corresponding hybrid materials, can be partially attributed to the fact that in MOF-5, contrary to HKUST-1, the metallic sites are saturated. As a result of this, ammonia is able to bind directly to the copper sites of HKUST-1, which enhances the adsorption. As seen from Table 11, the measured adsorption capacities of the hybrid materials are always higher than the ones calculated for the physical mixture, thus indicating a synergetic effect between the MOF component and GO. This synergetic effect is the result of the presence of the new pore space developed in the hybrid materials where the dispersive forces are enhanced compared to MOF due to the presence of GO.

TABLE 11

Ammonia breakthrough capacities (measured and hypothetical) for the parent materials and the hybrid materials.

| Sample | NH$_3$ breakthrough capacity [mg/g of adsorbent] | |
|---|---|---|
| | Measured | Hypothtical |
| GO | 61 | — |
| MOF-5 | 43 | — |
| ZnMG-1 | 53 | 43 |
| ZnMG-2 | 80 | 46 |
| GO | 33 | — |
| HKUST-1 | 172 | — |
| CuMG-1 | 200 | 165 |
| CuMG-2 | 182 | 147 |

To analyze the mechanism(s) of adsorption and their effect(s) on the adsorbents structure, the exhausted samples were analyzed by various techniques and the data obtained are compared to the ones found for the initial samples. The new features observed with the MOF samples and the hybrid materials are stressed herein vis-à-vis the GO sample. This does not imply that the GO is not involved in the adsorption process. On the contrary, ammonia retention on GO is present and has already been described in the literature (Petit et al. 2009). Consequently, only the main features of this adsorption are reintroduced here. X-ray diffraction spectra of the samples before and after exposure to ammonia were analyzed. Ammonia adsorption causes changes in the structure of the materials. For GO sample, a decrease in the interlayer (shift of the peak at higher $\Theta$ values) is observed. This decrease is related to the fact that ammonia reacts with the functional groups of GO present on basal planes (epoxy groups) and at their edges (sulfonic) (Petit et al. 2009). These reactions result in bond cleavages which lead to a more efficient staking of the graphene layers and thus a decrease of the interlayer distance (Petit et al. 2009). For all exhausted zinc-based samples, a complete modification of the XRD pattern is observed indicating the collapse of the MOF structure. The resulting spectra look like the one of MOF-69c (Rosi et al. 2005). In the latter study, the destruction of MOF-5 was related to the hydrogen bonds between water and the zinc oxide tetrahedra. Due to the similar chemistry of the water and ammonia molecules, it can be hypothesized that the partial collapse of the MOF structure is due to the hydrogen bonding of ammonia and/or water and the zinc oxide tetrahedra. A decomposition of the MOF network is observed for the copper-based samples as well. Indeed as seen from the X-ray diffraction patterns of HKSUT-1 and the hybrid materials exposed to ammonia, the intensity of the peaks significantly decreased. Unlike in the case of zinc-based materials, for the copper-based samples, this decomposition is likely caused by the formation of complexes between ammonia and the components of HKUST-1. This complexation is evidenced by variations of color of the adsorbents bed during the breakthrough tests. At the beginning of the tests, the bed color changes from dark blue to sky blue. This has already been observed and linked to the binding of ammonia to the copper sites (in axial position) (Britt et al. 2008). Progressively, a new color appears (Maya blue) which indicates the formation of a different copper-based compound. The latter species is hypothesized to be $Cu(OH)_2$ since on the X-ray diffraction pattern of HKUST-1-E and CuMG-2-E, a new peak appears at ~18° (Liu et al. 2008; Wu et al. 2005).

Information on the water stability of the MOFs can also be derived from the X-ray diffraction patterns. When MOF-5 is exposed to water, the diffraction pattern is completely altered indicating a collapse of the MOF structure. On the contrary, for HKUST-1, the diffraction pattern is preserved suggesting the water stability. These observations are in agreement with the ones reported in the literature (Kaye et al. 2007; Küsgens et al. 2009). Similar trends as for the parent MOFs are observed for each type of hybrid materials.

Further details and support on the mechanisms of adsorption for both series of samples are provided by FTIR spectroscopy. The spectrum of the initial GO sample exhibit several bands which can be attributed to the various oxygen and sulfur functionalities present on that material (Petit et al. 2009). New features, although not well-defined due to the graph's scale, can be observed after exposure to ammonia. A new band at ~1430 cm$^{-1}$ is seen and assigned to N—H vibration in $NH_4^+$ (Petit et al. 2009). The broad overlapping bands between 3100 and 3700 cm$^{-1}$ are attributed to the vibrations of O—H and N—H (Petit et al. 2009). Other changes in the spectra of GO after exposure to ammonia are related to the modifications in the functional groups of GO after reacting with $NH_3$ (Petit et al. 2009). New bands are observed for all exhausted MOFs and hybrid samples. In the case of MOF-5 and the corresponding hybrid materials, new bands appear at 1295, 1220 and 655 $cm^{-1}$. This is accompanied by more intense bands at 1500 and 1385 $cm^{-1}$ while the initial broad band around 1600 $cm^{-1}$ "is replaced" by a thinner one at 1585 $cm^{-1}$. The latter changes in the region 1350-1600 $cm^{-1}$ can be attributed to modifications in the coordination of the carboxylate groups from BDC and the zinc centers (Nakamoto 2009). These modifications are likely related to the decomposition of the MOF-5 structure described previously and are similar to the ones observed when MOF-5 is exposed to water. Moreover, N—H vibrations appear at ~3325 $cm^{-1}$ on MOF-5-E and ZnMG-2-E. Whereas a small band at ~1700 $cm^{-1}$ is observed on the spectrum of MOF-5 exposed to moist air, this feature is not seen for MOF-5-E and ZnMG-2-E. Since this band is related to the acidic form of BDC, its absence on the latter two samples suggests that ammonia might be interacting with the carboxylate groups of BDC (released by decomposition of the structure) to form $(NH_4)_2BDC$. A similar analysis can be made for HKUST-1 and the corresponding hybrid material. New bands are observed at ~1620, 1260 and 1210 $cm^{-1}$ and a broadening of the bands at 1450, 1370 and 730 $cm^{-1}$ is seen with and an increase in the intensity of the band at ·1560 $cm^{-1}$. The latter feature is assigned to a change in the coordination of the carboxylate ligands from BTC (Nakamoto 2009). Moreover, the appearance of the thin band at ~1620 $cm^{-1}$ and the ones at ~1260 and 1210 $cm^{-1}$, as well as the broadening of the bands at 1370 and 1450 $cm^{-1}$, suggest the presence of BTC "alone" (not coordinated to copper) (Shi et al. 2008). Once again, the absence of the band at ~1720 $cm^{-1}$ excludes the presence of the acidic form of BTC (Seo et al. 2009). N—H vibrations are observed at ~3350 $cm^{-1}$ on HKUST-1-E and CuMG-2-E spectra. Considering all of this, as for the zinc-based materials, the formation of $(NH_4)_3BTC$ is hypothesized.

All of this is supported by the results of thermal analyses. Decomposition of the MOF structure upon ammonia adsorption is observed for almost all samples via the shift, broadening and decrease of the peak related to the decomposition of BDC (400-550° C. for zinc-based compounds) or BTC (300-400° C. for copper-based compounds). Moreover, for the exhausted zinc-based materials, only one broad peak is observed between 400 and 550° C. suggesting the decomposition of only one type of species (likely $(NH_4)_2BDC$. On the contrary, for the exhausted copper-based materials, the broad peak between 300-400° C. exhibits several shoulders indicating that BTC must be present in different compounds. These compounds can be HKUST-1, $Cu(NH_3)_2BTC_{2/3}$ and $(NH_4)_3BTC$. New peaks are also seen between 150 and 350° C. on MOF-5-E. This is also observed to a lesser extent for the hybrid materials. Similarly, a broad peak is observed between 150 and 270° C. on HKUST-1-E and on the hybrid materials too. These peaks are likely related to the removal of ammonia and/or the decomposition of $Zn(OH)_2$ for the zinc-based materials and, $Cu(OH)_2$ for the copper-based materials (Lu and Yeh 2000).

It is found that the features of the MOF component are dominant in the hybrid materials. Their formation occur via the coordination of the oxygen groups of GO with the metallic centers of the MOF. The arrangement of GO and the MOF depends on the type of oxygen group involved (from the basal planes or the edges of GO) as well as the geometry of the metallic center. This building process leads to the creation of a new pore space between the MOF blocks and GO with increased dispersive forces. This is likely responsible for their enhanced adsorption capacities. Overall, better performances are obtained on the copper-based materials than that on the zinc-based materials, which must be related to the presence of unsaturated metallic sites in HKUST-1. Ammonia adsorption causes the collapse of the materials. While in the case of MOF-5 based materials, it is initiated by the hydrogen-bonding of ammonia with the zinc oxide tetrahedra of the MOF, for the copper-based samples, ammonia progressively reacts with the adsorbents via formation of the complexes and leads to their decomposition.

Example 7

Reactive Adsorption of Ammonia on Cu-Based MOF and Graphene Composites

Composites based on HKUST-1 and graphene layers are tested for ammonia adsorption at room temperature in both dry and moist conditions. The materials are characterized by X-ray diffraction, FT-IR spectroscopy, adsorption of nitrogen and thermal analyses. These materials are water stable. Ammonia adsorption capacities on the composites are higher than the ones calculated for the physical mixture of components, suggesting the presence of a synergetic effect between the MOF and graphene layers. The increased porosity and dispersive forces being the consequence of the presence of graphene layers are responsible for the enhanced adsorption. In addition to its retention via physical forces, ammonia is also adsorbed via binding to the copper sites in HKUST-1 and then, progressively, via reaction with the MOF component. This reactive adsorption is visible through two successive changes of the adsorbents' color during the breakthrough tests. More ammonia is adsorbed in moist conditions than in dry conditions owing to its dissolution in a water film present in the pore system.

Experimental

Materials

The synthesis of the parent materials, referred to as HKUST-1 and GO, was done following the syntheses described by Millward and coworkers (Millward et al., *J. Am. Chem. Soc.* 2005, 127, 17998-17999) for HKSUT-1 and Seredych and Bandosz (Seredych et al., *J. Phys. Chem. C* 2007, 111, 15596-15604) for GO. The preparation of the composites whose GO content ranges from 5 to 46 wt % of the final material weight (5, 9, 18, 38, and 46 wt %) is described in the present specification. The composites are referred to as MG-n with n=1, 2, 3, 4 and 5, for the different GO contents (5, 9, 18, 38, and 46 wt %, respectively).

$NH_3$ Breakthrough Dynamic Test

In order to determine the ammonia breakthrough capacity, dynamic breakthrough tests were performed at room temperature. In a typical test, a flow of ammonia diluted with air went through a fixed bed of adsorbent with a total inlet flow rate of 225 mL/min and an ammonia concentration of 1000 ppm. The adsorbent's bed contained about 2 $cm^3$ of glass beads well mixed with the amount of adsorbent required to obtain a homogeneous bed (between 50 and 120 mg). The mixture was packed into a glass column. The beads were used to avoid the pressure drop and thus to favor the kinetics of the breakthrough tests. The concentration of ammonia in the outlet gas was measured using an electrochemical sensor (Multi-Gas Monitor ITX system). The adsorption capacity of each adsorbent was calculated in mg per g of sorbent by integration of the area above the breakthrough curve. Tests in dry and wet conditions were implemented by diluting the ammonia stream with either dry or moist air stream, respectively. This was done to analyze the effects of water on the adsorption capacity. In another series of test, the adsorbents were subjected to a flow of moist air only for 30 minutes. This prehumidifcation step was followed by a breakthrough test in dry conditions. After the breakthrough tests, all samples were exposed to a flow of carrier air only (180 mL/min) to impose the desorption of ammonia and thus to evaluate the strength of its retention. The suffixes -ED and -EM are added to the name of the samples after exposure to ammonia in dry and moist conditions, respectively.

XRD

X-ray diffraction (XRD) measurements were conducted using standard powder diffraction procedures. Adsorbents (initial and exhausted) were ground with DMF (methanol for GO) in a small agate mortar. The mixture was smear-mounted onto a glass slide and then analyzed by $Cu_{K\alpha}$ radiation generated in a Philips X'Pert X-ray diffractometer. A diffraction experiment was run on standard glass slide for the background correction.

Thermal Analysis

Thermogravimetric (TG) curves and their derivatives (DTG) were obtained using a TA Instrument thermal analyzer. The samples (initial and exhausted) were heated from 30 to 1000° C. with a heating rate of 10 deg/min under a flow of nitrogen held at 100 mL/min.

FT-IR Spectroscopy

Fourier transform infrared (FT-IR) spectroscopy was carried out as described in Example 1.

pH

The pH of the samples before exposure to $NH_3$ was measured. The adsorbent powder (about 0.1 g) was stirred overnight with distilled water (5 mL) and then the pH of the suspension was recorded.

Sorption of Nitrogen

Nitrogen isotherms of the samples were measured as described in Example 6.

Results

Measured ammonia breakthrough and desorption curves in both dry and moist conditions were calculated. Table 12 lists the adsorption capacities calculated from the breakthrough curves. When analyzing the breakthrough curves, one has to remember that the mass of adsorbent taken to prepare the bed varies from one material to another. Consequently, a comparison of the breakthrough time might not be relevant to assess the efficiency of the materials. However, it is interesting to study the shape of the curves. In dry conditions, steep breakthrough and desorption curves are observed for all materials suggesting the fast kinetics of adsorption and the strong retention of ammonia on the adsorbents, respectively. When tests are performed in the presence of water, a first increase in ammonia concentration is observed which then levels off at about 5 ppm for HKUST-1 and for the composites (especially MG-1-EM and MG-2-EM samples). Then ammonia concentration increases more rapidly. The variations in the features of the breakthrough curves between moist and dry conditions suggest different mechanisms of adsorption. The first increase in the ammonia concentration on the breakthrough curves in moist conditions might be due to a competition for adsorption between water and ammonia molecules since both are known to bind the copper sites of HKUST-1. Indeed, at the beginning, if water molecules tend to bind preferentially to the metallic centers, some ammonia molecules might not find any available sites to coordinate to and are thus released in the outlet stream. Then some quasi-equilibrium is reached and it allows the adsorption of ammonia which explains the "slow-down" in the increase in the ammonia concentration. Moreover, based on the shape of the desorption curves in moist conditions, it seems that ammonia interactions with the adsorbents are weaker than in dry conditions. Finally, in both dry and moist conditions it is observed that GO has breakthrough and desorption curves steeper than the ones of HKUST-1 and the composites. This indicates faster kinetics of interactions between ammonia and the adsorbent as well as a stronger retention of the molecules on the adsorbent's surface.

TABLE 12

Ammonia breakthrough capacities (measured and recalculated) and initial surface pH values for the parent and composites materials.

| Sample | $NH_3$ breakthrough capacity [mg/g of carbon] | Hypothetical $NH_3$ breakthrough capacity [mg/g of carbon] | pH initial |
| --- | --- | --- | --- |
| GO-ED | 45 | — | 2.47 |
| GO-EM | 33 | — | 2.47 |
| HKUST-1-ED | 115 | — | 4.19 |
| HKUST-1-EM | 172 | — | 4.19 |
| MG-1-ED | 128 | 111 | 4.22 |
| MG-1-EM | 200 | 165 | 4.22 |
| MG-2-ED | 131 | 108 | 4.34 |
| MG-2-EM | 231 | 159 | 4.34 |
| MG-3-ED | 149 | 102 | 4.45 |
| MG-3-EM | 182 | 147 | 4.45 |
| MG-4-ED | 87 | 88 | 4.23 |
| MG-4-EM | 147 | 119 | 4.23 |
| MG-5-ED | 70 | 81 | 4.32 |
| MG-5-EM | 123 | 108 | 4.32 |

Based on the breakthrough capacities listed in Table 12, HKUST-1 appears as a good adsorbent of ammonia and exhibits a better performance in moist conditions. The values found are in the range of the ones reported by Peterson et al. (*J. Phys. Chem. C* 2009, 113, 13906-13917) (112 mg/g in dry conditions and 151 mg/g in moist conditions). Nevertheless, it has to be mentioned that the exact experimental conditions and structure of the adsorbent were likely different.

Unlike HKUST-1, GO shows a better capacity in dry conditions. The capacities of the composites MG-1, MG-2 and MG-3, in dry conditions, are higher than those for the parent materials. For these three samples, the adsorption capacity increases with the content of GO from 128 mg/g to 149 mg/g. On the contrary, MG-4 and MG-5 exhibit a lower adsorption capacity than HKUST-1 and a decrease in their performance is noticed as the amount of GO increases. It is interesting to compare all these values to the adsorption capacities calculated assuming the physical mixture between the two components of the composites. As seen from Table 12, the measured breakthrough capacities are always higher than the "hypothetical" ones except for MG-4 and MG-5 run in dry conditions. This suggests that except for the two latter materials, a synergetic effect occurs between the components of the composites. Two phenomena can explain this effect. The first one is the presence of increased dispersive forces in the composites owing to the presence of graphene layers. The second one is linked to the increased porosity of the composites compared to the parent materials. Overall, the improvement is better pronounced in the moist conditions than in the dry conditions. The surface area of MG-1, MG-2 and MG-3 was about 10% higher than the one of HKUST-1 (between 8 and 15% increase for the volume of micropores). Owing to this enhanced porosity, more space is available in the composites for water to be adsorbed when tests are performed in the presence of humidity. An increase in the amount of water adsorbed causes that the composites can adsorb more ammonia via its dissolution in the water film than can the parent materials. Obviously, this effect cannot be observed in dry conditions since water is absent in the system. In this case, only the effect of the increased dispersive forces and additional porosity can be considered. In both experimental conditions (dry and moist), the improvement follows a "Gaussian" curve pattern: it first increases with an increase in the amount of GO and then decreases when this content is more than 36 wt % (MG-4) for the dry conditions and 18 wt % (MG-3) for the moist conditions. This trend is in agreement with the one reported for the parameters of the porous structure for the materials studied. This supports the hypothesis that the increased porosity and dispersive forces of the composites are responsible for the enhancement in the ammonia retention.

Unlike in the studies reported in the literature on the adsorption of ammonia on HKUST-1, two changes of color of the bed, and not only one, were noticed during the breakthrough tests on HKUST-1 and on the composites. The first color change (from dark blue to deep sky blue) appeared much faster in the moist conditions than in the dry conditions. For both conditions, the second color change (from deep sky blue to Maya blue) was slower than the first change of color. The tints observed were slightly greener (teal) with the composites compared to HKUST-1 alone. Intuitively, the first change of color could be attributed to the binding of ammonia (dry conditions) or water/ammonia (moist conditions) to the copper sites. The second change of color could then originate from the formation of a new complex resulting from ammonia adsorption. A first thought is the formation of the well-known "Schweizer's reagent." This complex, whose formula is $Cu(NH_3)_4(H_2O)_2^{2+}$, has been evidenced by Peterson and coworkers as the final product of ammonia adsorption on HKUST-1 in moist conditions. In the instant case, the presence of this complex seems unlikely since its color (deep blue) does not correspond to the one we observed. Even when the exhausted samples were immersed in water, no deep blue color was noticed.

To understand the mechanisms of retention, the exhausted materials run in both conditions must be analyzed. In order to distinguish between the effect of ammonia retention on the structure of the materials and the influence of water adsorption (for experiments run in moist air), HKUST-1 and the composites were exposed to a flow of humid air only for the same period of time as for the breakthrough/desorption tests. The samples were then analyzed in the same way as the ones exposed to ammonia. Comparison of the results can throw some light on the adsorption process(es).

Changes in the X-ray diffraction patterns of the materials exposed to ammonia were studied. Ammonia adsorption leads to a decrease in the interlayer distance of GO in both dry and moist conditions, as shown by the shift of the single peak towards higher 2 Θ values. This phenomenon is caused by the reaction of ammonia with the functional groups present in the interlayer space of GO. Indeed, the ring opening caused by the reaction of epoxy groups with ammonia and the cleavage of the C—S bond (in sulfonic groups attached to the graphene layers) due to the action of the superoxide ions were shown to lead to a more ordered staking of the graphene layers and thus a decrease of the interlayer distance. Almost all the peaks on the diffraction patterns of HKUST-1 and the composites disappear after ammonia adsorption in dry conditions. This indicates that the HKUST-1 component has lost, at least partially, its crystalline structure to form one or more amorphous compounds. This is in agreement with the findings of Peterson and coworkers. Unlike on the diffraction patterns for the samples run in dry conditions, in moist conditions, most peaks remain after ammonia adsorption but their intensities significantly decreased. It seems that despite the larger amount of ammonia adsorbed in moist conditions, some part of the HKUST-1 structure remains preserved. This can be explained by the fact that a significant part of the ammonia adsorbed was retained by dissolution in the water film and consequently did not react with the MOF structure. This hypothesis is supported by the shape of the desorption curves described above indicating that a significant part of $NH_3$ was only weakly retained on the materials (HKUST-1 and composites). In the X-ray diffraction patterns of HKUST-1-EM and MG-3-EM, is the appearance of a new peak at 2 Θ~18.3° after exposure to ammonia. This suggests the formation of a new compound. Even though additional data would be required for the precise identification of this species, the assignment of this peak to $Cu(OH)_2$ seems plausible. The location of the peak is in agreement with the one reported in the literature. The presence of this compound during ammonia adsorption on HKUST-1 was evidenced previously. When the materials are exposed to humidity only, the diffraction patterns are mostly preserved with a decrease in the intensity of the peaks. This suggests that water, even though it is not supposed to lead to the decomposition of HKUST-1 structure in ambient conditions, caused some distortion in the materials at high humidity levels.

The FT-IR spectra of the materials before and after ammonia adsorption were analyzed.

Several new features are observed for the exhausted samples. In the case of GO-ED and GO-EM, a new band at $\sim$1430 cm$^{-1}$ is seen and assigned to N—H vibration in $NH_4^+$. The broad overlapping bands between 3100 and 3700 cm$^{-1}$ are attributed to the vibrations of O—H (from phenol) and N—H (from $NH_4^+$, $NH_3$ and $NH_2$). The other changes in the spectra of GO after exposure to ammonia are related to the modifications in the surface groups of GO due to their reaction with $NH_3$. Briefly, a decrease in the intensity of the band at 1230 cm$^{-1}$ is due to the reaction of ammonia with the epoxy groups and/or the oxidation of the sulfonic groups into sulfates. The broadening of the band at 1630 cm$^{-1}$ can be assigned to O—H vibration formed by reaction of the epoxy groups with ammonia and/or N—H vibrations in ammonia or amine. For HKUST-1 and the composites, new bands are observed at $\sim$1620, 1260 and 1210 cm$^{-1}$. This is accompanied by a broadening of the bands at 1450, 1370 and 730 cm$^{-1}$ and an increase in the intensity of the band at $\sim$1560 cm$^{-1}$. Moreover, the thin band at $\sim$1620 cm$^{-1}$ "replaces" the larger one at 1645 cm$^{-1}$. All these features are even more pronounced for samples run in moist conditions. For the latter materials (except MG-5-EM), two bands at $\sim$3350 and 3190 cm$^{-1}$ appear and are attributed to ammonia and water vibrations. The absence of these bands in dry conditions is in agreement with the lower adsorption capacities in those cases as well as with the absence (or at least the lower content) of water in the system. An increase in the intensity of the band at $\sim$1560 cm$^{-1}$ must be related to a change in the coordination of the carboxylate ligands from BTC. Moreover, based on the appearance of the thin band at 1620 cm$^{-1}$ and the ones at $\sim$1260 and 1210 cm$^{-1}$, as well as the broadening of the bands at 1370 and 1450 cm$^{-1}$, the spectra tend to look as the one reported for BTC alone. Besides, the absence of the band at 1720 cm$^{-1}$ excludes the presence of the acidic form of BTC. Based on all these observations, it is thus hypothesized that, during ammonia adsorption, the carboxylate groups from BTC react with ammonia to form $(NH_4)_3BTC$. When the samples are exposed to moist air only, no significant changes are observed except in the range related to the carboxylate groups (1650-1300 cm$^{-1}$). This indicates variations in the coordination of the ligands to the copper sites. This is linked to the distortion caused by water in the copper-BTC bridging. This is in agreement with the X-ray diffraction data for which a decrease in the intensity of the peaks of the HKUST-1 component was observed for all samples exposed to humid air only.

DTG curves obtained from the thermal analyses were analyzed for all the materials tested. In dry conditions, two broad peaks can be seen before the decomposition of the HKUST-1 structure: a first one between 30 and 110° C. (centered at ~70° C.) and a second one at ~110-270° C. (highest intensity between 180 and 230° C.). The latter peak can be related to the removal of strongly adsorbed ammonia (on the copper sites, via hydrogen bonding to the oxygen atoms of the carboxylate ligands or from $(NH_4)_3BTC$) and/or to the release of water from $Cu(OH)_2$. The first peak is linked to the removal of ammonia physically adsorbed in small pores. A broad peak revealed between 270 and 400° C. is likely related to the decomposition of BTC. However, the different shoulders present at this temperature range (at 320, 340 and 360° C.) on MG-1, MG-2 and MG-3 samples suggest that more than one compound containing BTC is present. These compounds might include: HKUST-1, $Cu(NH_3)_2BTC_{2/3}$ and $(NH_4)_3BTC$. In moist conditions, a first peak at about 90° C. is observed and assigned to the removal of physically adsorbed water. The latter peak comes with a small shoulder at ~115° C. which is better seen for HKUST-1 and MG-1 samples. That peak represents the removal of weakly adsorbed ammonia/ammonia dissolved in water. As for dry conditions, the continuous weight loss between ~110 and 270° C. is related to the removal of strongly adsorbed ammonia and/or the release of water from $Cu(OH)_2$. A broad peak at ~325° C. is also observed. Unlike the curves in dry conditions, the shoulders of the latter peak are less visible. A great part of the HKUST-1 component has probably already decomposed to form $(NH_4)_3BTC$. A peak at ~40° C. is observed on the DTG curve of MG-2-EM only. When the materials are exposed to moist air only, the DTG curves are not significantly modified. However, the shape of the peak related to the decomposition of the HKUST-1 structure is changed suggesting some changes/distortion in the structure caused by water adsorption. This is in agreement with the X-ray diffraction and FT-IR data. A broad peak is observed at ~100° C. and assigned to the removal of water. Similar conditions in terms of humidity levels and duration of the tests were used to run the ammonia adsorption in moist conditions and to expose the materials to moist air only. Despite this, the amount of water desorbed at ~100° C. is greater in the latter case. This suggests the preferred adsorption of ammonia on the materials compared to the one of water when the two molecules are present in the system. This is supported by the fact that when samples were subjected to a step of prehumidification before the breakthrough test (see Experimental section for description of the tests), the breakthrough capacities obtained were similar to the ones found in dry conditions. Moreover, the results of the analyses of the exhausted samples after the prehumidification (X-ray, FT-IR, thermal analyses) lead to results similar to the ones obtained in dry conditions.

After exposure to ammonia in dry conditions, selected samples (HKUST-1, MG-1 and MG-3) were analyzed by nitrogen adsorption to assess the effect of ammonia retention on the porosity of the samples. The exhausted samples were found non porous. This supports the collapse of the MOF structure and the complexation processes described above.

Thus, the MOF/graphene composites exhibit much better ammonia adsorption capacities than the ones calculated for the physical mixture of HKUST-1 and GO. This indicates the presence of a synergetic effect between the two components. This is linked to the increase in porosity and the enhanced dispersive forces in the composites compared to the parent materials. In addition to its physical adsorption, ammonia is adsorbed via binding to the copper sites in HKUST-1 (formation if $Cu(NH_3)_2BTC_{2/3}$) and then progressively via reaction with the MOF component. It is suggested that this reaction leads to the formation of $Cu(OH)_2$ and $(NH_4)_3BTC$. These two steps of adsorption (binding and reaction) are visible through two successive changes of color of the adsorbents during the breakthrough tests. The amount of ammonia adsorbed is higher in moist conditions than in dry conditions owing to its dissolution in the water film present in materials' pores. These are water stable and are thus better adapted to environmental applications than the MOF-5/GO composites which collapsed in presence of moisture.

EXAMPLE 8

The Synthesis and Characterization of Copper-Based MOF/Graphene Composites

Composites of a copper-based metal-organic framework and graphene were synthesized with different ratios of HKUST-1 and graphite oxide. These compounds, as well as the parent materials, were characterized by X-ray diffraction, sorption of nitrogen, FT-IR spectroscopy, thermal analyses, scanning electron microscopy, and sorption of hydrogen. The composites exhibit features similar to HKUST-1 as well as an increased porosity compared to the parent materials. The formation of new small pores is demonstrated by an increase in the hydrogen uptake. The results suggest that the building process of the composites occurs via the reaction/binding of the copper dimers from the HKUST-1 with/to the functional groups in graphite oxide (epoxy, carboxylic, hydroxylic, sulfonic).

Experimental

Materials

Graphite oxide was synthesized by oxidation of graphite (Sigma-Aldrich) using the Hummers' method. The details are described in Petit et al. (*J Mater Chem* 2009;19, 6521-28). HKUST-1 was prepared as described in Example 6.

The preparation of the composites was done by adding GO powder to well-dissolved MOF precursors and solvent mixture obtained in the same procedure as in the preparation of HKUST-1. The resulting mixture was sonicated for 5 minutes, stirred for another 30 minutes and then the same synthesis procedure as that for HKUST-1 was carried out. The added GO consisted of 5, 9, 18, 38, and 46 wt % of the final material weight. The composites are referred to as MG-n with n=1, 2, 3, 4 and 5, for the different GO contents (5, 9, 18, 38, and 46 wt %, respectively). In the case of MG-5, unlike for the other composites, two different batches of GO were used in the synthesis.

Methods

XRD

X-ray diffraction (XRD) measurements were conducted as described in Example 6. A diffraction experiment was run on standard glass slide for the background correction.

Sorption of Nitrogen; Determination of Porosity

Nitrogen isotherms of the samples were measured as described in Example 6.

Adsorption of Hydrogen

Hydrogen isotherms were measured on the samples at 77 K and less than 1 bar. The analysis was performed on an Autosorb 1-C instrument (Quantachrome). Approximately 0.10 g of composites and HKUST-1 was outgassed up to 150° C. before the analysis, with care taken to slowly ramp up the temperature to avoid damaging the pores. The GO was outgassed at room temperature so that the surface oxidation would not be lost. The sample cells were kept sealed and ultra-high purity hydrogen was used to prevent moisture contamination of the samples.

Thermal Analysis

Thermogravimetric (TG) curves and their derivatives (DTG) were obtained using a TA Instrument thermal analyzer. The samples were heated up to 1000° C. with the heating rate 10 deg/min under a flow of nitrogen of 100 mL/min.

FT-IR Spectroscopy

Fourier transform infrared (FT-IR) spectroscopy was carried out as described in Example 6.

HRTEM

Transmission electron microscopy was performed on a JEOL 2100F instrument with an accelerating voltage of 200 kV. The analyses were conducted on samples previously suspended in methanol.

SEM

Scanning electron microscopy (SEM) was performed as described in Example 6.

Results

In the X-ray diffraction patterns of GO, a single peak around 2Theta 9.3° is revealed. It indicates a distance between the graphene layers of 9.5 Å as determined by Bragg's law. For HKUST-1, the pattern obtained is in accordance with the one reported in the literature for this specific network. This proves the successful synthesis procedure. The similar diffraction patterns of the composites to HKUST-1 indicate the existence of the well-defined MOF units in the synthesized materials. Thus, one can assume that GO did not prevent the formation of linkages between the copper dimers and the organic bridges. On the other hand, it is interesting to notice that the rather broad $d_{002}$ peak observed for GO is not seen for the composites. A reason for this might be the exfoliation/high dispersion of GO during the preparation of the composites. Indeed, the composites' synthesis involved polar solvents (in particular DMF) that are known to disperse GO very well. The intensity of the peaks in MG-3 and MG-4 is lower than the other composites.

An important parameter in gas adsorption is the porosity of the adsorbent. In the instant case, this feature has been evaluated using nitrogen isotherms. The data for GO are not reported here since its porosity is negligible. All the materials exhibit a type I isotherm with a small hysteresis loop. This indicates the predominant microporous character of these compounds. The hysteresis loops suggest the presence of mesopores, which might be those between the small crystals of MOF or composite particles.

composites with the lowest GO contents (MG-1 to MG-3) are higher than the ones of HKUST-1 while the opposite trend is observed for the composites with the highest GO contents (MG-4 and MG-5). From a theoretical point of view, it is interesting to compare the measured values of the composites' structural parameters with "hypothetical" ones. The latter parameters correspond to the values that would be obtained if no chemical interactions were involved in the formation of the composites. In other words, they represent the parameters of porous structure of the physical mixture of GO and HKUST-1. These "hypothetical" surface areas and pore volumes reported for the composites were calculated taking into account the percentage of each component in the composites and the structural parameters of GO and HKUST-1 alone. Equation (7) provides the details of the calculations.

$$X_n = X_{GO} \times \text{wt}\%_{GO} + X_{HKUST-1} \times \text{wt}\%_{HKUST-1} \quad (7)$$

with "$X_n$" being the parameter of composite MG-n to determine (surface area or volume of pores), "$X_{GO}$" and "$X_{HKSUT-1}$" being the parameters of GO and HKUST-1 separately, and "wt $\%_{Go}$" and "wt $\%_{HKSUT-}1$" being the weight percentages of GO and HKUST-1 in MG-n. Details on these values are presented in Table 13. The measured values (surface area, micropore volume or total volume of pores) are always higher than those calculated for the physical mixture. This reveals the presence of a synergy between the two components, which leads to the formation of a compound with a higher porosity than that formed when the two phases are only a physical mixture. That degree of improvement between measured and "hypothetical" values first increases with the GO content for composites MG-1, 2 and 3 and then decreases when the GO content is equal or higher than 38 wt %. The best porous structure is found for MG-3. This trend is likely due to the presence of increased amounts of GO causing too much distortion in the structure of the materials. Another explanation could be that when a high amount of GO is present, the number of groups on GO exceeds the numbers of accessible sites on MOF with which they can react. Part of the graphene layers will thus act as if there was no other species in the system apart from the solvents. Consequently, upon drying these layers will be restacked together in a more or less ordered way as they usually do. This excess causes an agglomeration of graphene layers and thus in a decrease in the porosity.

TABLE 13

Parameters of porous structure derived from nitrogen isotherms and the hypothetical values (H) calculated, and the amount (measured and hypothetical (H)) of $H_2$ adsorbed derived from hydrogen isotherms.

| Sample | $S_{BET}$ [m²/g] | $V_t$ [cm³/g] | $V_{meso}$ [cm³/g] | $V_{mic}$ [cm³/g] | $V_{mic}/V_t$ | $S_{BET}$ (H) [m²/g] | $V_t(H)$ [cm³/g] | $V_{mic}(H)$ [cm³/g] | $H_2$ adsorbed [g/kg] | $H_2$ adsorbed (H) [g/kg] |
|---|---|---|---|---|---|---|---|---|---|---|
| HKUST-1 | 909 | 0.471 | 0.022 | 0.449 | 0.95 | — | — | — | 22.3 | — |
| MG-1 | 989 | 0.515 | 0.037 | 0.478 | 0.93 | 864 | 0.447 | 0.426 | 23.6 | 21.2 |
| MG-2 | 1002 | 0.527 | 0.049 | 0.478 | 0.91 | 827 | 0.428 | 0.409 | 21.7 | 20.3 |
| MG-3 | 996 | 0.566 | 0.044 | 0.522 | 0.92 | 746 | 0.386 | 0.368 | 20.3 | 18.3 |
| MG-4 | 704 | 0.370 | 0.052 | 0.348 | 0.94 | 565 | 0.292 | 0.278 | — | — |
| MG-5 | 620 | 0.345 | 0.051 | 0.294 | 0.85 | 492 | 0.263 | 0.251 | — | — |

HKUST-1 has a BET surface area of about 900 m².g⁻¹ which is in the range of the values reported in the literature. Details on the values of the parameters of porous structure is in Table 13. The surface area and volume of pores of the Thermogravimetric analyses provide information about the thermal stability of the materials, which can be also linked to their chemistry. The DTG curves for the parent materials and the composites were obtained. No significant weight loss was measured above 450° C. Analyses were performed up to 1000° C. In the case of GO, three major peaks were observed. The first one up to 100° C. corresponds to the removal of physically adsorbed water. The second peak around 200° C. represents the decomposition of epoxy groups and a broad hump between 250° C. and 400° C. indicates the decomposition of carboxylic and sulfonic groups. The DTG curve of HKUST-1 exhibits a small peak at about 100° C., which corresponds to a dehydration step. Additional molecules of water are released at ~300° C. The complete collapse of the HKUST-1 structure is then observed with the intense peak at ~350° C. This is accompanied by the release of $CO_2$ and leads to the formation of copper oxide. This temperature range for the decomposition of HKUST-1 is in accordance with literature. The DTG curves for the composites look rather similar to the one of HKUST-1 except that the peak at ~300° C. in the case of MG-1 has a lower intensity than that for HKUST-1 and is absent for the composites with higher graphite content. The absence of that additional step of dehydration compared to HKUST-1 suggests that some copper centers in the composites are engaged into a more hydrophobic environment. They are probably located in the vicinity of graphene layers. The interesting feature here is the absence of the intense peak related to the decomposition of GO epoxy groups for the composites. An explanation for this would be the involvement of these groups in the formation of the composites and more precisely the coordination of the cupric ions to the oxygen atoms of the epoxy groups. This scenario is consistent with the observed lack of dehydration step at 300° C. This does not exclude the fact that the carboxylic, hydroxylic and sulfonic functionalities of GO have also likely reacted with the copper dimers. These interactions between the metallic species and GO, leading to the new spatial arrangement of the components, might be the source of the increased porosity of the composites. It is important to note that even though the MOF units can be attached to the functional groups of GO, this should not modify the structure of the MOF. The graphene layers via the oxygen groups should only act as a "termination" unit in the process of MOF formation. This is supported by X-ray diffraction, nitrogen adsorption analysis, thermal analyses and FT-IR spectroscopy since the pattern of HKUST-1 can be recognized in each composite.

The FT-IR spectra of the parent materials and the composites were obtained. Since the range above 2300 $cm^{-1}$ does not present features relevant to this analysis, only the range between 500-2300 $cm^{-1}$ is reported. The IR spectrum of GO has been described in detail in literature. Vibration of C—O appears at 1060 $cm^{-1}$ and the vibration of O—H bond in water and/or oxygen surface groups is observed at 1630 $cm^{-1}$. C=O vibration from carboxyl and/or carbonyl groups is detected at 1735 $cm^{-1}$. Two other bands are observed at 990 and 1228 $cm^{-1}$. The first band can be assigned to epoxy/peroxide groups and the second to S=O asymmetric stretching vibration in sulfonic groups and/or vibration of C–O in epoxides. The spectrum of HKUST-1 is very similar to those found in literature for the same network. This spectrum can be divided into two zones. The first zone, below 1300 $cm^{-1}$, shows various bands assigned to the vibrations of the BTC ligand. The zone between 1300 and 1700 $cm^{-1}$ is related to the carboxylate ligands and is thus indicative of the coordination of BTC to the copper sites. More precisely, the bands at 1645 and 1590 $cm^{-1}$ and at 1450 and 1370 $cm^{-1}$ corresponds to the asymmetric and symmetric stretching vibrations of the carboxylate groups in BTC, respectively. In agreement with the data of X-ray diffraction and thermal analyses, the FT-IR spectra of the composites exhibit features similar to the HKUST-1 spectrum. The variations in the ratios of the bands at 1645/1590 $cm^{-1}$ and 1450/1370 $cm^{-1}$ must be related to changes in the environment of the carboxylate ligands. A plausible explanation would be the interactions of these ligands with the functional groups from GO as well as the distortion in the structure of HKUST-1 caused by the introduction of GO. The progressive decrease in the intensity of the bands can be noticed as the content in GO increases. This decrease might be related to the lower amount of MOF in the samples.

Addition of GO to HKUST-1 causes visible changes in the materials. The composites with the highest GO content appear much darker than the ones with low GO content for which the color resembles more the one of HKUST-1 alone. The gradation in the color through the range of samples is more visible when the materials are immersed in DMF and then dried in air. The greenish tint of the compounds is due to the adsorption of DMF. This color is converted to a darker green tint as the GO content increases.

Crystals of different sizes are observed in the case of HKUST-1 and their surface appears relatively smooth despite the presence of some defects. Some crystals exhibit an octahedral shape characteristic of that specific MOF. Dense packing of graphene layers aggregated into flakes can be distinguished for GO. The structure of the composites show some variations compared to the ones of the parent materials. In the case of MG-2, a quite complex texture is observed with the presence of layers quite similar to the ones encountered in MOF-5/GO composites in Examples 1 and 2. It is possible that as for the latter materials, these layers correspond to alternation between blocks of HKUST-1 and blocks of graphene layers. This alternation process can be explained considering that, in the synthesis medium, GO is present along with the MOF precursors. Consequently, in this system, copper ions can either react with the oxygen groups of the BTC ligands to form HKUST-1 crystals or with the oxygen groups of GO. Depending on the amount of GO, one process might be favored over another. A few meso/macropores are also observed on the surface of MG-2. The porous character becomes more pronounced in MG-3. This is in agreement with the increase in porosity observed before. For MG-4, although some remains of the porous structure seen on MG-3 are present, these features tend to disappear. Separate agglomerates of GO are also observed for this composite. This part of the GO which does not interact with the MOF units can be responsible for the decrease in porosity observed when high content of GO are present.

The synergy between the components of the composites was also tested by evaluation of the hydrogen adsorption capacity at 77 K. Isotherms show the excess adsorption as a function of the pressure. Gibb's excess or excess adsorbed mass is defined as the mass of adsorbate film minus the mass of an equal volume of adsorptive. This amount of gas is in excess of what would be in the pores if there were no adsorbent-adsorbate interaction. At the low pressures (<1 bar) used, excess adsorption can be used to approximate the absolute amount of gas adsorbed. Details on the values of the excess adsorption for the materials studied are presented in Table 13. Only MG-1, MG-2 and MG-3 were chosen owing to the observed increase in the porosity noticed based on adsorption of nitrogen. Even though the differences in the isotherms seem to be insignificant, one has to take into account the composition of the composites. It is noticeable that GO does not adsorb any hydrogen. In spite of the small size of $H_2$ molecule (~3 Å), it is not able to enter the interlayer space. This can be explained by the presence in that space of epoxy and hydroxy groups blocking the entrance of a non-polar molecule of hydrogen. The hydrogen uptake of HKUST-1 and the composites are in the range of uptakes reported in the literature for the MOF alone. The similarity in amount of hydrogen adsorbed between all the samples studied, with an increase in the GO content up to 20 wt %, indicates the presence of a new porosity in the composites resulting from a synergy between GO and MOF. The measured amount of hydrogen adsorbed were compared to the "hypothetical" amount calculated assuming the physical mixture of the components. These "hypothetical" values were calculated following the same method as described in Equation (1). Details on the "hypothetical" values of the excess adsorption are presented in Table 13. The positive effect of the composites porosity/synergy between the two components is demonstrated in about 10% increase compared to the "hypothetical" physical mixture of GO and HKUST-1. This confirms the results obtained from nitrogen adsorption and can be linked to the measured increase in the porosity. Indeed, the total volume of micropores increased by 6% for MG-1 and MG-2 and 15% MG-3 compared to HKUST-1 alone. Even though the total volume of pores increased more (9% for MG-1, 11% for MG-2 and 18% for MG-3), they seem to not be significant for hydrogen adsorption owing to their large sizes. For hydrogen adsorption at supercritical temperature, the volume of pores on the order of magnitude of the diameter of a hydrogen molecule should be the most important factor affecting the amount adsorbed. Moreover, hydrogen can access pores much smaller than those detected by nitrogen molecules. There is an agreement between an increase in the "hypothetical" surface area and an increase in the hydrogen adsorption. This implies that the composites have similar pore size distributions with narrow pores and surface areas to HKUST-1 but are superior to the graphene oxide alone.

Considering the observations, the overall structure of the composites can be envisioned. The formation of the composites is hypothesized to occur via the reaction between the copper sites of HKUST-1 and the functional groups of GO and especially the epoxy, hydroxylic, sulfonic and carboxylic functionalities. The reaction of the epoxy groups with the HKUST-1 units have been identified via thermal analyses as described above. To further confirm this observation, GO was subjected to the same synthesis conditions as for the composites but in the absence of HKUST-1 precursors. Thermal analysis of the resulting material was then performed. The peak related to epoxy groups was still present on the DTG curve confirming that its absence on the DTG curves of the composites was the consequence of their reaction/interaction with the HKUST-1 units. Moreover, the reactions of the carboxylic groups with the copper sites of HKUST-1 can occur since the BTC component already presents such functionalities. Regarding the hydroxylic groups, their interactions with the copper sites can be compared to interactions with water. Given the octahedral molecular geometry of copper complexes, the oxygen groups of GO can either act as equatorial (replacing a BTC molecule) or axial ligands (replacing a molecule of water). Detailed scenarios of the possible interactions are provide in FIG. 7. These two possibilities of arrangement (axial and equatorial), along with the different types of oxygen groups from GO, lead to the formation of a composite with the relatively disordered structure proposed in FIG. 8. Although very schematic, this representation can help to visualize the texture of the materials prepared. This disordered arrangement is responsible for the creation of the new porosity detected by nitrogen and hydrogen adsorption. Nevertheless, because carboxylic groups (and sulfonic groups) of GO are located at the edges of the layers and not on the basal planes as the other functionalities, their interactions with the copper sites do not lead to the same type of arrangement as for epoxy, and hydroxylic present on the basal planes of GO. This can be seen in FIG. 8b. Higher content of GO leads to the formation of larger pores between the graphene flakes. This is the result of the interactions of more carboxylic groups (and sulfonic groups) on GO edges with copper sites. This is supported by $N_2$ sorption analyses which showed that the volumes of mesopores increased with the GO content (Table 12). When even higher amounts of GO are present, the number of groups from GO can exceed the number of accessible MOF sites they can react with and the graphene layers remains as agglomerates. This is represented in FIG. 8c. This causes that smaller volumes of new small pores are formed. This is in agreement with the SEM pictures of the composites with high GO content for which agglomerates of GO were observed.

The features of HKUST-1 in the composites are dominant but their porosity is higher than the parent materials. It is hypothesized that the reaction of the HKUST-1 units with the functionalities of GO (epoxy, hydroxylic, carboxylic and sulfonic groups) lead to the creation of new pores. This enhancement in the porosity is well-seen for GO content up to 30 wt % and then decreases. Indeed, when high amounts of GO are present, the number of groups on the graphene layers likely exceeds the number of accessible sites in MOF with which they can react. Consequently, the graphene layers remain as agglomerates resulting in a decrease in porosity. The additional porosity is responsible for the enhancement in the hydrogen uptake of the composites compared to the ones calculated for the physical mixture of HKUST-1 and GO.

Example 9

Preparation of the MOF-199/Graphite Composite

The MOF-199/Graphite composite was prepared by mixing copper nitrate hemipenta-hydrate (10 g) and 1,3,5 benzenetricarboxylic acid (5 g) in N,N dimethylformamide (DMF, 85 mL) in a 500 mL beaker. The mixture was stirred and then sonicated for 5 min. Ethanol (85 mL) was added to the above mixture, followed by stirring and sonication for 5 min. Deionized water (85 mL) was added to the mixture, followed by stirring and sonication for 5 min. Graphite (Sigma Aldrich) was then added (1.4 g) followed by stirring and sonication for 30 min.

The mixture was transferred into a round-bottom flask and heated at 85° C., in an oil bath, for 21 hours, under shaking (except the last hour). After cooling, the crystals were filtrated using a Buchner funnel, washed with dichoromethane and immersed in dichloromethane. The "unreacted" graphite left at the bottom of the flask was discarded. Dichloromethane was changed twice during two days. Finally, crystals were collected by filtration and placed inside a closed filtering flask connected to an aspirator used to create vacuum inside the flask, and heated at 170° C. for 28 hours. The resulting crystals (about 8 g) were then kept in a dessicator. The synthesized composite is referred to as MOF-199/Graphite.

The amount of graphite contained in the composite was estimated by thermogravimetric analysis in air as the weight loss between 400 and 700° C. This corresponds to about 10 wt % of graphite.

TABLE 14

Parameters of porous structure derived from nitrogen isotherms and the hypothetical values (H) calculated for the physical mixture.

| Sample | $S_{BET}$ [m²/g] | $V_t$ [cm³/g] | $V_{meso}$ [cm³/g] | $V_{mic}$ [cm³/g] | $V_{mic}/V_t$ | $S_{BET}(H)$ [m²/g] | $V_t(H)$ [cm³/g] | $V_{mic}(H)$ [cm³/g] |
|---|---|---|---|---|---|---|---|---|
| MOF-199 | 909 | 0.471 | 0.022 | 0.449 | 0.95 | — | — | — |
| MG-1 | 989 | 0.515 | 0.037 | 0.478 | 0.93 | 864 | 0.447 | 0.426 |
| MG-2 | 1002 | 0.527 | 0.049 | 0.478 | 0.91 | 827 | 0.428 | 0.409 |
| MG-3 | 996 | 0.566 | 0.044 | 0.522 | 0.92 | 746 | 0.386 | 0.368 |
| MG-4 | 704 | 0.370 | 0.052 | 0.348 | 0.94 | 565 | 0.292 | 0.278 |
| MG-5 | 620 | 0.345 | 0.051 | 0.294 | 0.85 | 492 | 0.263 | 0.251 |
| MOF-199/Graphite | 917 | 0.478 | 0.031 | 0.447 | 0.94 | 818 | 0.424 | 0.404 |

TABLE 15

Ammonia adsorption capacity measured and calculated for the physical mixture and composition of the composite materials.

| Sample | $NH_3$ breakthrough capacity [mg/g of carbon] | Breakthrough capacity of the physical mixture [mg/g of carbon] | GO content[1] [wt %] | Graphite content[2] [wt %] |
|---|---|---|---|---|
| GO-ED | 27 | — | 100 | 0 |
| GO-EM | 31.1 | — | 100 | 0 |
| MOF-199-ED | 115 | — | 0 | 0 |
| MOF-199-EM | 172 | — | 0 | 0 |
| MG-1-ED | 128 | 111 | 4.7 | 0 |
| MG-1-EM | 200 | 165 | 4.7 | 0 |
| MG-2-ED | 131 | 108 | 9.2 | 0 |
| MG-2-EM | 231 | 159 | 9.2 | 0 |
| MG-3-ED | 149 | 102 | 18.0 | 0 |
| MG-3-EM | 182 | 147 | 18.0 | 0 |
| MG-4-ED | 87 | 88 | 38.0 | 0 |
| MG-4-EM | 147 | 119 | 38.0 | 0 |
| MG-5-ED | 70 | 81 | 46.0 | 0 |
| MG-5-EM | 123 | 108 | 46.0 | 0 |
| MOF-199/Graphite-ED | 127 | 104[3] | 0 | 10 |
| MOF-199/Graphite-EM | 198 | 155[c] | 0 | 10 |

[1]Determined from the amount of GO used for the synthesis.
[2]Determined from thermal analysis in air.
[3]Calculated considering that graphite does not adsorb ammonia.

The invention claimed is:

1. A nanocomposite material comprising:
graphite-based material dispersed among transition metal-organic framework (MOF) units, wherein the graphite-based material is chemically linked to MOF units; wherein the graphite-based material is present in the range of about 5 wt. % to about 60 wt. % of the nanocomposite material.

2. The nanocomposite material of claim 1 wherein the graphite-based material is graphene, graphite, graphite oxide, or mixtures thereof 3. The nanocomposite material of claim 1 wherein the MOF units are copper-based MOF units, zinc-based MOF units, iron-based MOF units, cobalt-based MOF units, nickel-based MOF units, or chromium-based MOF units.

4. The nanocomposite material of claim 1 wherein the MOF units are $Cu_3$(benzenetricarboxylic)$_2$ units.

5. The nanocomposite material of claim 1 wherein the MOF units are $Zn_4O$(H-1,4-benzenedicarboxylate)$_3$ units.

6. The nanocomposite material of claim 1 wherein the MOF units are MIL-100 units comprising iron.

7. The nanocomposite material of claim 1 wherein the MOF units are $Cu_3$(benzenetricarboxylic)$_2$ units, and wherein the graphite-based material is present in the range of about 5 wt. % to about 50 wt. % of the nanocomposite material.

8. The nanocomposite material of claim 1 wherein the MOF units are $Zn_4O$(H-1,4-benzenedicarboxylate)$_3$ units, and wherein the graphite-based material is present in the range of about 5 wt. % to about 50 wt. % of the composite material.

9. A nanocomposite material comprising graphite-based material dispersed among transition metal-organic framework (MOF) units,
wherein the graphite-based material is chemically linked to the MOF units, wherein the nanocomposite material is formed by contacting the graphite-based material with precursors of the MOF units, and wherein the graphite-based material is present in the range of about 5 wt. % to about 60 wt. % of the nanocomposite material.

10. A method of making a nanocomposite material, the method comprising:
dispersing graphite-based material in precursors of transition metal-organic framework (MOF) units, wherein the nanocomposite material is formed by chemical linking of the graphite-based material with the MOF units, wherein the graphite-based material is present in the range of about 5 wt. % to about 60 wt. % of the nanocomposite material.

11. A method of adsorbing gas, the method comprising exposing the gas to a nanocomposite material, wherein the nanocomposite material comprises:
graphite-based material dispersed among transition metal-organic framework (MOF) units, wherein graphite-based material is chemically linked to MOF units, wherein the graphite-based material is present in the range of about 5 wt. % to about 60 wt. % of the nanocomposite material.

12. The method of claim 11 wherein the gas is acidic toxic gas, basic toxic gas, or mixtures thereof.

13. The method of claim 12 wherein the gas is selected from the group consisting of $NH_3$, $NO_x$, $H_2S$, $SO_2$, $AsH_3$, or combinations thereof.

14. The method of claim 12 wherein the gas is NO and/or $NO_2$, and wherein the MOF units are $Cu_3$(benzenetricarboxylic)$_2$ units, and wherein the graphite-based material is present in the range of about 5 wt. % to about 20 wt. % of the composite material, and wherein the adsorption is conducted under dry conditions.

15. The method of claim 12 wherein the gas is $H_2S$, and wherein the MOF units are $Cu_3$(benzenetricarboxylic)$_2$ units, and wherein the graphite-based material is present in the range of about 5 wt. % to about 50 wt. % of the composite material.

16. The method of claim 12 wherein the gas is $NH_3$, and wherein the MOF units are $Cu_3$(benzenetricarboxylic)$_2$ units, and wherein the graphite-based material is present in the range of about 5 wt. % to about 20 wt. % of the composite material.

17. The method of claim 12 wherein the gas is $NH_3$, and wherein the MOF units are $Zn_4O$(H-1,4-benzenedicarboxylate)$_3$ units, and wherein the graphite-based material is present in the range of about 5 wt. % to about 50 wt. % of the composite material, and wherein the adsorption is conducted under dry conditions.

* * * * *

UNITED STATES PATENT AND TRADEMARK OFFICE
CERTIFICATE OF CORRECTION

PATENT NO. : 8,633,331 B2  
APPLICATION NO. : 12/879701  
DATED : January 21, 2014  
INVENTOR(S) : Bandosz et al.

Page 1 of 1

It is certified that error appears in the above-identified patent and that said Letters Patent is hereby corrected as shown below:

On the title page, item (54) and in the specification, column 1, line 1, title

Now reads: "Nanocomposite Materials Comprising Metal-Organic-Framework Units and Methods of Using Same";

Should read: -- Nanocomposite Materials Comprising Metal-Organic-Framework Units and Graphite-Based Materials, and Methods of Using Same --.

In the Specification

Column 2, line 61

Now reads: "and one water molecule";

Should read: -- and one water molecule. --.

Column 3, line 8

Now reads: "with imidazolate-type links";

Should read: -- with imidazolate-type links. --.

Column 3, line 58

Now reads: "30 wt% to about 40 %, and then decreases";

Should read: -- 30 wt% to about 40 wt%, and then decreases. --.

Column 3, line 64

Now reads: "in terms of 25 spatial arrangement.";

Should read: -- in terms of spatial arrangement. --.

Column 5, line 58

Now reads: "precursors of HKUST-1. MOF-5 and MIL-100.";

Should read: -- precursors of HKUST-1, MOF-5 and MIL-100. --.

Signed and Sealed this  
Eleventh Day of November, 2014

Michelle K. Lee  
*Deputy Director of the United States Patent and Trademark Office*